United States Patent [19]
Eckhouse

[11] Patent Number: 5,626,631
[45] Date of Patent: May 6, 1997

[54] METHOD AND APPARATUS FOR THERAPEUTIC ELECTROMAGNETIC TREATMENT

[75] Inventor: Shimon Eckhouse, Haifa, Israel

[73] Assignee: ESC Medical Systems Ltd., Yokneam, Israel

[21] Appl. No.: 383,509

[22] Filed: Feb. 3, 1995

Related U.S. Application Data

[63] Continuation-in-part of Ser. No. 964,210, Oct. 20, 1992, Pat. No. 5,405,368.

[51] Int. Cl.⁶ .................................................. A61N 5/06
[52] U.S. Cl. .................................................. 607/88; 606/9
[58] Field of Search ........................... 507/88, 89, 90, 507/91, 92, 93, 94; 606/2, 3, 9, 10, 11, 12, 13, 17, 18, 19

[56] References Cited

U.S. PATENT DOCUMENTS

| | | |
|---|---|---|
| 4,022,534 | 5/1977 | Kishner . |
| 4,298,005 | 11/1981 | Mutzhas . |
| 4,608,978 | 9/1986 | Rohr .................................. 606/11 |
| 4,686,986 | 8/1987 | Fenyö et al. ........................ 607/90 |
| 4,757,431 | 7/1988 | Cross et al. . |
| 4,784,135 | 11/1988 | Blum et al. . |
| 4,829,262 | 5/1989 | Furumoto . |
| 4,930,504 | 6/1990 | Diamantopoulos et al. . |
| 4,950,880 | 8/1990 | Hayner . |
| 5,161,526 | 11/1992 | Hellwing et al. . |
| 5,207,671 | 5/1993 | Franken et al. . |
| 5,217,455 | 6/1993 | Tan . |
| 5,259,380 | 11/1993 | Mendes et al. . |
| 5,320,618 | 6/1994 | Gustafsson . |
| 5,344,418 | 9/1994 | Ghaffari . |

FOREIGN PATENT DOCUMENTS

3906860A1  9/1989  Germany .

*Primary Examiner*—Angela D. Sykes
*Assistant Examiner*—Eric F. Winakur
*Attorney, Agent, or Firm*—Foley & Lardner

[57] ABSTRACT

A therapeutic treatment device for coagulating blood in blood vessels underlying an epidermal layer is disclosed having an incoherent light source operable to provide a pulsed light output for treatment and a driver circuit, including a switch capable of being electrically turned on and being electrically turned off to thereby provide a first interval of light, connected to the light source to control the pulse width and delay between pulses.

10 Claims, 8 Drawing Sheets

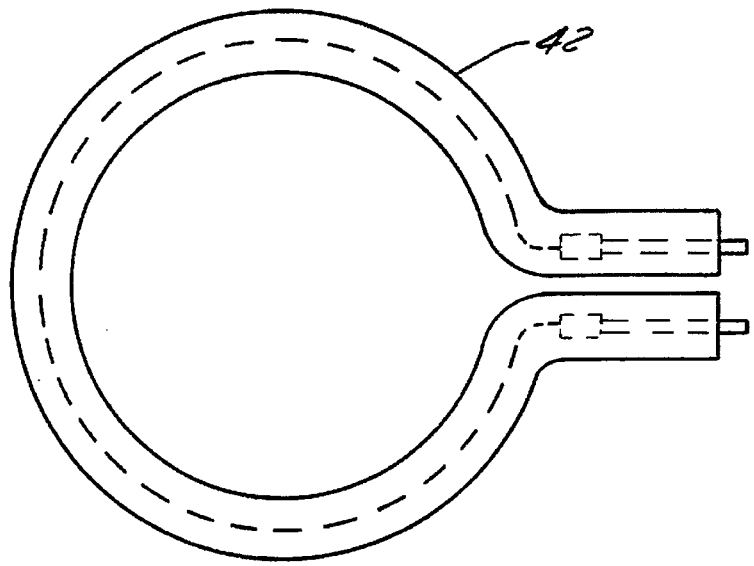
FIG. 5
FIG. 6
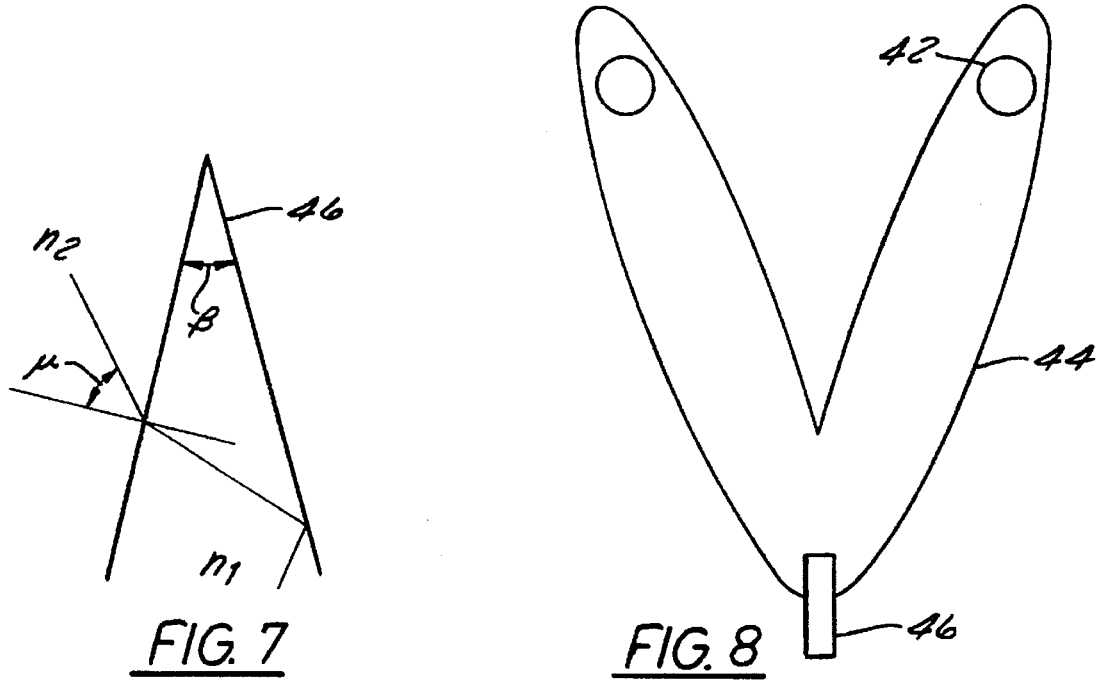
FIG. 7
FIG. 8

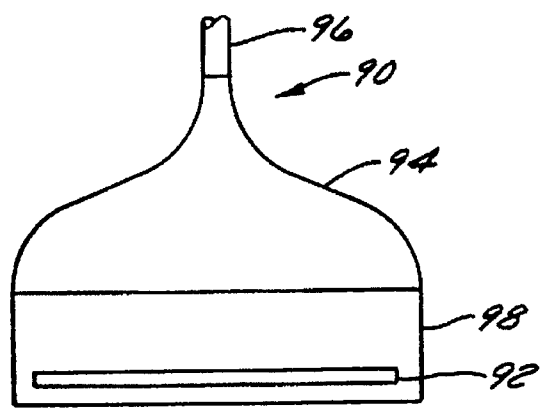
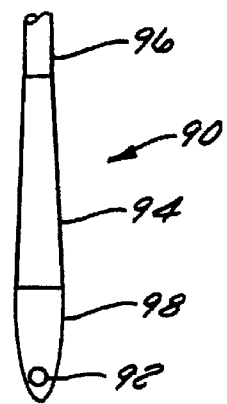
FIG. 9   FIG. 10
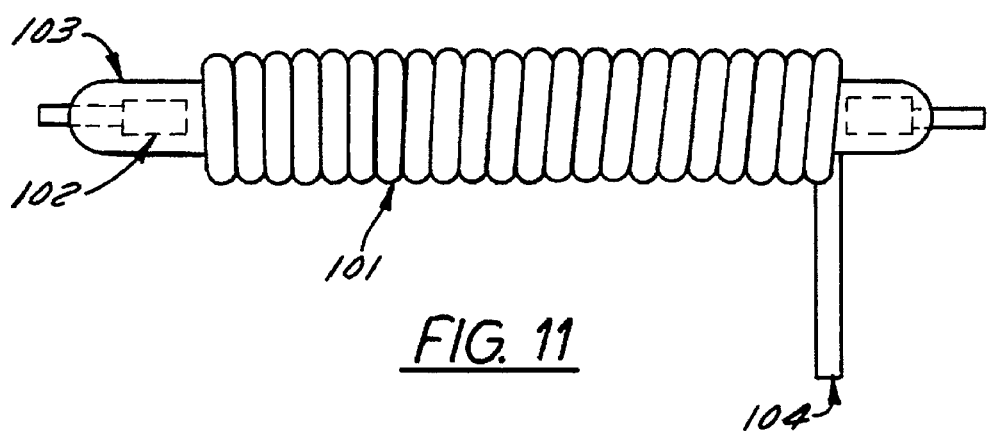
FIG. 11
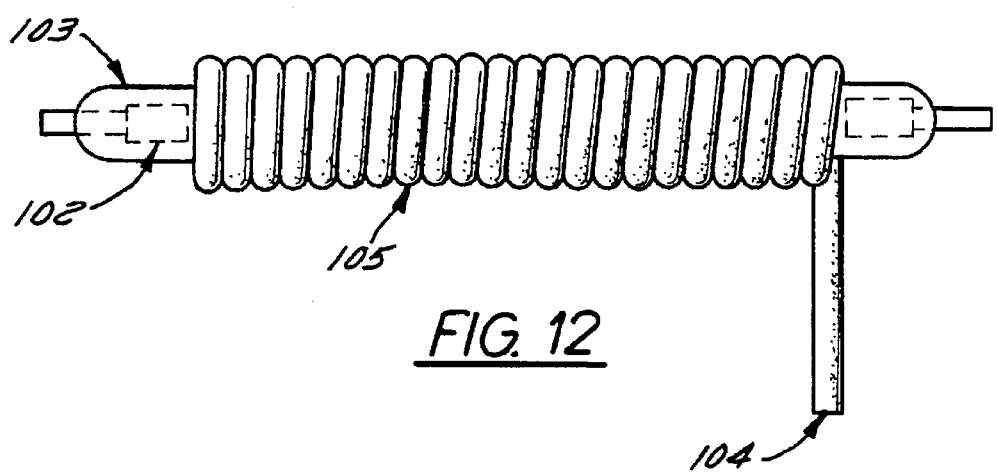
FIG. 12

METHOD AND APPARATUS FOR THERAPEUTIC ELECTROMAGNETIC TREATMENT

RELATED APPLICATION

This application is a continuation-in-part of prior U.S. application Ser. No. 07/964,210, filed Oct. 20, 1992, now U.S. Pat. No. 5,405,368, entitled "Method And Apparatus For Therapeutic Electromagnetic Treatment."

FIELD OF THE INVENTION

The present invention relates generally to the art of therapeutic electromagnetic treatment and more specifically to a method and apparatus for utilizing a spatially extended pulsed light source such as a flashlamp (flash tube) for such a treatment or, efficiently focusing light from the flashlamp into optical fibers for therapeutic treatment or other applications.

BACKGROUND OF THE INVENTION

It is known in the prior art to use electromagnetic radiation in medical application for therapeutic uses such as treatment of skin disorders. For example, U.S. Pat. No. 4,298,005 to Mutzhas describes a continuous ultraviolet lamp with cosmetic, photobiological, and photochemical applications. A treatment based on using the UV portion of the spectrum and its photochemical interaction with the skin is described. The power delivered to the skin using Mutzhas' lamp is described as 150 W/m$^2$, which does not have a significant effect on skin temperature.

In addition to prior art treatment involving UV light, lasers have been used for dermatological procedures, including Argon lasers, $CO_2$ lasers, Nd(Yag) lasers, Copper vapor lasers, ruby lasers and dye lasers. For example, U.S. Pat. No. 4,829,262 to Furumoto, describes a method of constructing a dye laser used in dermatology applications. Two skin conditions which may be treated by laser radiation are external skin irregularities such as local differences in the pigmentation or structure of the skin, and vascular disorders lying deeper under the skin which cause a variety of skin abnormalities including port wine stains, telangiectasias, leg veins and cherry and spider angiomas. Laser treatment of these skin disorders generally includes localized heating of the treatment area by absorption of laser radiation. Heating the skin changes or corrects the skin disorder and causes the full or partial disappearance of the skin abnormality.

Certain external disorders such as pigmented lesions can also be treated by heating the skin very fast to a high enough temperature to evaporate parts of the skin. Deeper-lying vascular disorders are more typically treated by heating the blood to a high enough temperature to cause it to coagulate. The disorder will then eventually disappear. To control the treatment depth a pulsed radiation source is often used. The depth the heat penetrates in the blood vessel is controlled by controlling the pulse width of the radiation source. The absorption and scattering coefficients of the skin also affect the heat penetration. These coefficients are a function of the constituents of skin and the wavelength of the radiation. Specifically, the absorption coefficient of light in the epidermis and dermis tends to be a slowly varying, monotonically decreasing function of wavelength. Thus, the wavelength of the light should be chosen so that the absorption coefficient is optimized for the particular skin condition and vessel size being treated.

The effectiveness of lasers for applications such as tattoo removal and removal of birth and age marks is diminished because lasers are monochromatic. A laser of a given wavelength may be effectively used to treat a first type of skin pigmentation disorder, but, if the specific wavelength of the laser is not absorbed efficiently by skin having a second type of disorder, it will be ineffective for the second type of skin disorder. Also, lasers are usually complicated, expensive to manufacture, large for the amount of power delivered, unreliable and difficult to maintain.

The wavelength of the light also affects vascular disorder treatment because blood content in the vicinity of the vascular disorders varies, and blood content affects the absorption coefficient of the treatment area. Oxyhemoglobin is the main chromophore which controls the optical properties of blood and has strong absorption bands in the visible region. More particularly, the strongest absorption peak of oxyhemoglobin occurs at 418 nm and has a band-width of 60 nm. Two additional absorption peaks with lower absorption coefficients occur at 542 and 577 nm. The total band-width of these two peaks is on the order of 100 nm. Additionally, light in the wavelength range of 500 to 600 nm is desirable for the treatment of blood vessel disorders of the skin since it is absorbed by the blood and penetrates through the skin. Longer wavelengths up to 1000 nm are also effective since they can penetrate deeper into the skin, heat the surrounding tissue and, if the pulse-width is long enough, contribute to heating the blood vessel by thermal conductivity. Also, longer wavelengths are effective for treatment of larger diameter vessels because the lower absorption coefficient is compensated for by the longer path of light in the vessel.

Accordingly, a wide band electromagnetic radiation source that covers the near UV and the visible portion of the spectrum would be desirable for treatment of external skin and vascular disorders. The overall range of wavelengths of the light source should be sufficient to optimize treatment for any of a number of applications. Such a therapeutic electromagnetic radiation device should also be capable of providing an optimal wavelength range within the overall range for the specific disorder being treated. The intensity of the light should be sufficient to cause the required thermal effect by raising the temperature of the treatment area to the required temperature. Also, the pulse-width should be variable over a wide enough range so as to achieve the optimal penetration depth for each application. Therefore, it is desirable to provide a light source having a wide range of wavelengths, which can be selected according to the required skin treatment, with a controlled pulse-width and a high enough energy density for application to the affected area.

Pulsed non-laser type light sources such as linear flashlamps provide these benefits. The intensity of the emitted light can be made high enough to achieve the required thermal effects. The pulse-width can be varied over a wide range so that control of thermal depth penetration can be accomplished. The typical spectrum covers the visible and ultraviolet range and the optical bands most effective for specific applications can be selected, or enhanced using fluorescent materials. Moreover, non-laser type light sources such as flashlamps are much simpler and easier to manufacture than lasers, are significantly less expensive for the same output power and have the potential of being more efficient and more reliable. They have a wide spectral range that can be optimized for a variety of specific skin treatment applications. These sources also have a pulse length that can be varied over a wide range which is critical for the different types of skin treatments.

In addition to being used for treating skin disorders, lasers have been used for invasive medical procedures such as lithotripsy and removal of blood vessel blockage. In such invasive procedures laser light is coupled to optical fibers and delivered through the fiber to the treatment area. In lithotripsy the fiber delivers light from a pulsed laser to a kidney or gallstone and the light interaction with the stone creates a shock wave which pulverizes the stone. To remove blood vessel blockage the light is coupled to the blockage by the fiber and disintegrates the blockage. In either case the shortcomings of lasers discussed above with respect to laser skin treatment are present. Accordingly, a treatment device for lithotripsy and blockage removal utilizing a flashlamp would be desirable.

To effectively treat an area the light from the source must be focussed on the treatment area. Coupling pulsed laser light into optical fibers in medicine is quite common. The prior art describes coupling isotropic incoherent point sources such as CW lamps into small optical fibers. For example, U.S. Pat. No. 4,757,431, issued Jul. 12, 1988, to Cross, et al. discloses a method for focusing incoherent point sources with small filaments or an arc lamp with an electrode separation of 2 mm into a small area. Point (or small) sources are relatively easy to focus without large losses in energy because of the small size of the source. Also, U.S. Pat. No. 4,022,534, issued May 10, 1977, to Kishner discloses light produced by a flash tube and the collection of only a small portion of the light emitted by the tube into an optical fiber.

However, the large dimension of an extended source such as a flashlamp makes it difficult to focus large fractions of its energy into small areas. Coupling into optical fibers is even more difficult since not only must a high energy density be achieved, but the angular distribution of the light has to be such that trapping in the optical fiber can be accomplished. Thus, it is desirable to have a system for coupling the output of a high intensity, extended, pulsed light source into an optical fiber.

SUMMARY OF THE PRESENT INVENTION

According to a first embodiment of the invention a therapeutic treatment device comprises a housing and an incoherent light source, suitably a flashlamp, operable to provide a pulsed light output for treatment, disposed in the housing. The housing has an opening and is suitable for being disposed adjacent a skin treatment area. A reflector is mounted within the housing proximate the light source, and at least one optical filter is mounted proximate the opening in the housing. An iris is mounted coextensively with the opening. Power to the lamp is provided by a variable pulse width pulse forming circuit. Thus, the treatment device provides controlled density, filtered, pulsed light output through an opening in the housing to a skin area for treatment.

According to a second embodiment of the invention a method of treatment with light energy comprises the steps of providing a high power, pulsed light output from a non-laser, incoherent light source and directing the pulsed light output to a treatment area. The pulse width of the light output is controlled and focussed so that the power density of the light is controlled. Also, the light is filtered to control the spectrum of the light.

According to a third embodiment of the invention a coupler comprises an incoherent light source such as a toroidal flashlamp. A reflector is disposed around the incoherent light source and at least one optical fiber or light guide. The fiber has an end disposed within the reflector. This end collects the light from the circular lamp. In a similar coupling configuration fibers may be provided, along with a linear to circular fiber transfer unit disposed to receive light from the light source and provide light to the optical fibers. The reflector has an elliptical cross-section in a plane parallel to the axis of the linear flash tube, and the linear flash tube is located at one focus of the ellipse while the linear to circular transfer unit is located at the other focus of the ellipse.

BRIEF DESCRIPTION OF THE DRAWINGS

For a better understanding of the invention, reference is made to the accompanying drawings, in which like numerals designate corresponding elements or sections throughout, and in which:

FIG. 5 is a side view of a toroidal flash tube;

FIG. 6 is a top view of a toroidal flash tube;

FIG. 7 shows the geometry for coupling into a conical section;

FIG. 8 is a cross-sectional view of a coupler for coupling light from a toroidal flash tube into an optical fiber with a flat edge;

FIG. 9 is a front sectional view of a coupler for coupling light from a linear flash tube into a circular fiber bundle;

FIG. 10 is a side sectional view of the coupler of FIG. 9;

FIG. 11 is a front view of a coupler for coupling light from a linear flash tube into an optical fiber;

FIG. 12 is a front view of a coupler for coupling light from a linear flash tube into a doped optical fiber;

In the various figures, like reference numerals are used to describe like components.

DETAILED DESCRIPTION OF THE PREFERRED EMBODIMENTS

Figure 1:
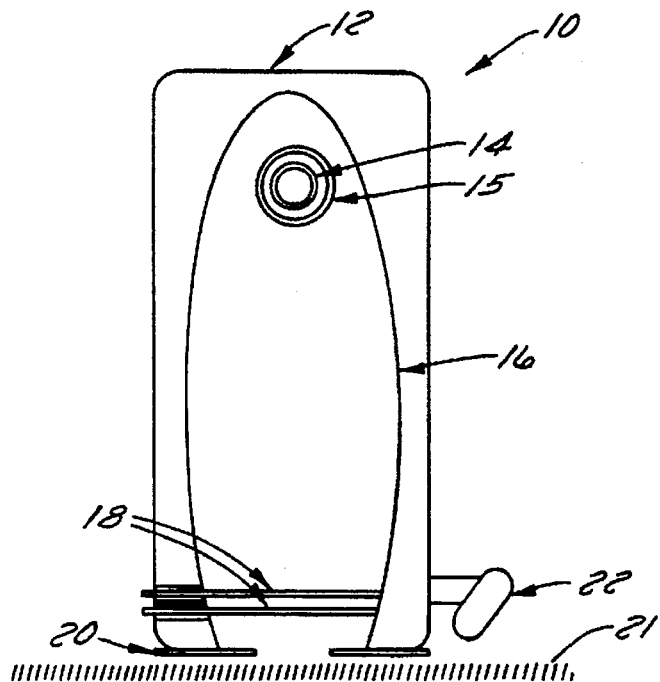
FIG. 1 is a cross-sectional view of an incoherent, pulsed light source skin treatment device.

Before explaining at least one embodiment of the invention in detail it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
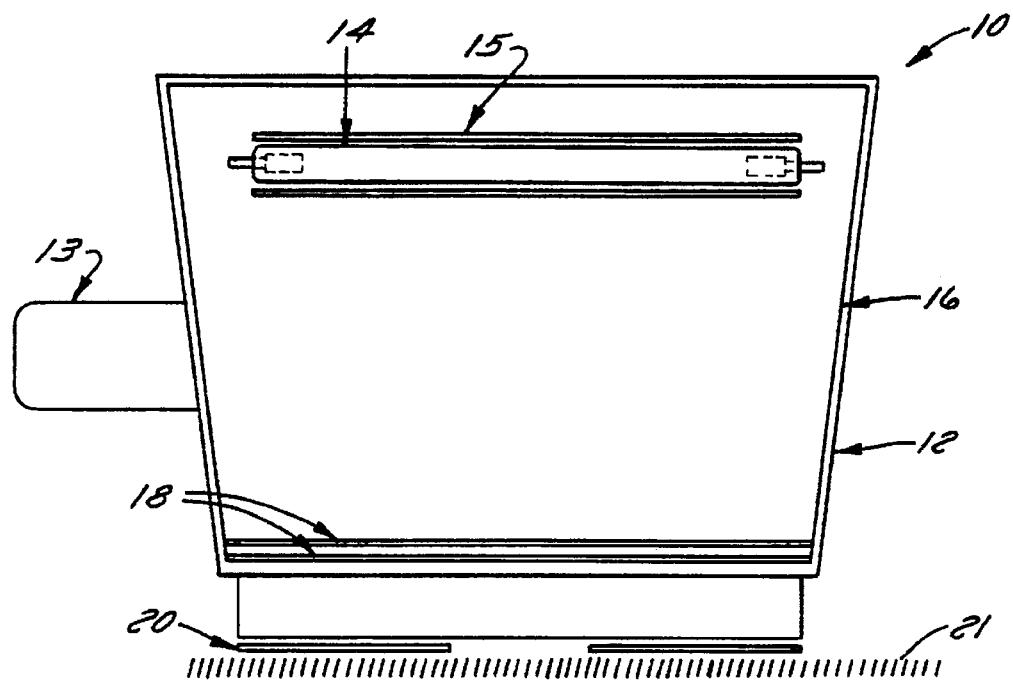
FIG. 2 is a side view of the light source of FIG. 1.

Referring now to FIGS. 1 and 2, cross-sectional and side views of an incoherent, pulsed light source skin treatment device 10 constructed and operated in accordance with the principles of the present invention are shown. The device 10 may be seen to include a housing 12, having an opening therein, a handle 13 (FIG. 2 only), a light source 14 having an outer glass tube 15, an elliptical reflector 16, a set of optical filters 18, an iris 20 and a detector 22 (FIG. 1 only).

Light source 14, which is mounted in housing 12, may be a typical incoherent light source such as a gas filled linear flashlamp Model No. L5568 available from ILC. The spectrum of light emitted by gas filled linear flashlamp 14 depends on current density, type of glass envelope material and gas mixture used in the tube. For large current densities (e.g., 3000 A/Cm$^2$ or more) the spectrum is similar to a black body radiation spectrum. Typically, most of the energy is emitted in the 300 to 1000 nm wavelength range.

To treat a skin (or visible) disorder a required light density on the skin must be delivered. This light density can be achieved with the focusing arrangement shown in FIGS. 1 and 2. FIG. 1 shows a cross-section view of reflector 16, also mounted in housing 12. As shown in FIG. 1, the cross-section of reflector 16 in a plane is perpendicular to the axis of flashlamp 14 is an ellipse. Linear flashlamp 14 is located at one focus of the ellipse and reflector 16 is positioned in such a way that the treatment area of skin 21 is located at the other focus. The arrangement shown is similar to focusing arrangements used with lasers and efficiently couples light from flashlamp 14 to the skin. This arrangement should not, however, be considered limiting. Elliptical reflector 16 may be a metallic reflector, typically polished aluminum which is an easily machinable reflector and has a very high reflectivity in the visible, and the UV range of the spectrum can be used. Other bare or coated metals can also be used for this purpose.

Optical and neutral density filters 18 are mounted in housing 12 near the treatment area and may be moved into the beam or out of the beam to control the spectrum and intensity of the light. Typically, 50 to 100 nm bandwidth filters, as well as low cutoff filters in the visible and ultraviolet portions of the spectrum, are used. In some procedures it is desirable to use most of the spectrum, with only the UV portion being cut off. In other applications, mainly for deeper penetration, it is preferable to use narrower bandwidths. The bandwidth filters and the cutoff filters are readily available commercially.

Glass tube 15 is located coaxially with flashlamp 14 and has fluorescent material deposited on it. Glass tube 15 will typically be used for treatment of coagulation of blood vessels to optimize the energy efficiency of device 10. The fluorescent material can be chosen to absorb the UV portion of the spectrum of flashlamp 14 and generate light in the 500 to 650 nm range that is optimized for absorption in the blood. Similar materials are coated on the inner walls of commercial fluorescent lamps. A typical material used to generate "warm" white light in fluorescent lamps has a conversion efficiency of 80%, has a peak emission wavelength of 570 nm and has a bandwidth of 70 nm and is useful for absorption in blood. The few millisecond decay time of these phosphors is consistent with long pulses that are required for the treatment of blood vessels.

Other shapes or configurations of flashlamp 14 such as circular, helical, short arc and multiple linear flashlamps may be used. Reflector 16 may have other designs such as parabolic or circular reflectors. The light source can also be used without a reflector and the required energy and power density may be achieved by locating light source 14 in close proximity to the treatment area.

Iris 20 is mounted in housing 12 between optical filters 18 and the treatment area and controls the length and the width of the exposed area, i.e. by collimating the output of flashlamp 14. The length of flashlamp 14 controls the maximum length that can be exposed. Typically an 8 cm long (arc length) tube will be used and only the central 5 cm of the tube is exposed. Using the central 5 cm assures a high degree of uniformity of energy density in the exposed skin area. Thus, in this embodiment the iris 20 (also called a collimator) will enable exposure of skin areas of a maximum length of 5 cm. The iris 20 may be closed to provide a minimum exposure length of one millimeter. Similarly, the width of the exposed skin area can be controlled in the range of 1 to 5 mm for a 5 mm wide flashlamp. Larger exposed areas can be easily achieved by using longer flash tubes or multiple tubes, and smaller exposure areas are obtainable with an iris that more completely collimates the beam. The present invention provides a larger exposure area compared to prior art lasers or point sources and is very effective in the coagulation of blood vessels since blood flow interruption over a longer section of the vessel is more effective in coagulating it. The larger area exposed simultaneously also reduces the required procedure time.

Detector 22 (FIG. 1) is mounted outside housing 12 and monitors the light reflected from the skin. Detector 22 combined with optical filters 18 and neutral density filters can be used to achieve a quick estimate of the spectral reflection and absorption coefficients of the skin. This may be carried out at a low energy density level prior to the application of the main treatment pulse. Measurement of the optical properties of the skin prior to the application of the main pulse is useful to determine optimal treatment conditions. As stated above, the wide spectrum of the light emitted from the non-laser type source enables investigation of the skin over a wide spectral range and choice of optimal treatment wavelengths.

In an alternative embodiment, detector 22 or a second detector system may be used for real-time temperature measurement of the skin during its exposure to the pulsed light source. This is useful for skin thermolysis applications with long pulses in which light is absorbed in the epidermis and dermis. When the external portion of the epidermis reaches too high a temperature, permanent scarring of the skin may result. Thus, the temperature of the skin should be measured. This can be realized using infra-red emission of the heated skin, to prevent over-exposure.

A typical real-time detector system would measure the infra-red emission of the skin at two specific wavelengths by using two detectors and filters. The ratio between the signals of the two detectors can be used to estimate the instantaneous skin temperature. The operation of the pulsed light source can be stopped if a preselected skin temperature is reached. This measurement is relatively easy since the temperature threshold for pulsed heating that may cause skin scarring is on the order of 50° C. or more, which is easily measurable using infra-red emission.

The depth of heat penetration depends on the light absorption and scattering in the different layers of the skin and the thermal properties of the skin. Another important parameter is pulse-width. For a pulsed light source, the energy of which is absorbed in an infinitesimally thin layer, the depth of heat penetration (d) by thermal conductivity during the pulse can be written as shown in Equation 1:

$$d=4[k\Delta t/C\rho]^{1/2} \quad \text{(Eq. 1)}$$

where k=heat conductivity of the material being illuminated;

Δt=the pulse-width of the light pulse;

C=the heat capacity of the material;

ρ=density of the material.

It is clear from Equation 1 that the depth of heat penetration can be controlled by the pulse-width of the light source. Thus, a variation of pulse-width in the range of $10^{-5}$ sec to $10^{-1}$ sec will result in a variation in the thermal penetration by a factor of 100.

Accordingly, the flashlamp 14 provides a pulse width of from $10^{-5}$ sec to $10^{-1}$ sec. For treatment of vascular disorders in which coagulation of blood vessels in the skin is the objective the pulse length is chosen to uniformly heat as much of the entire thickness of the vessel as possible to achieve efficient coagulation. Typical blood vessels that need to be treated in the skin have thicknesses in the range of 0.5 mm. Thus, the optimal pulse-width, taking into account the thermal properties of blood, is on the order of 100 msec. If shorter pulses are used, heat will still be conducted through the blood to cause coagulation, however, the instantaneous temperature of part of the blood in the vessel and surrounding tissue will be higher than the temperature required for coagulation and may cause unwanted damage.

For treatment of external skin disorders in which evaporation of the skin is the objective, a very short pulse-width is used to provide for very shallow thermal penetration of the skin. For example, a $10^{-5}$ sec pulse will penetrate (by thermal conductivity) a depth of the order of only 5 microns into the skin. Thus, only a thin layer of skin is heated, and a very high, instantaneous temperature is obtained so that the external mark on the skin is evaporated.

Figure 3:
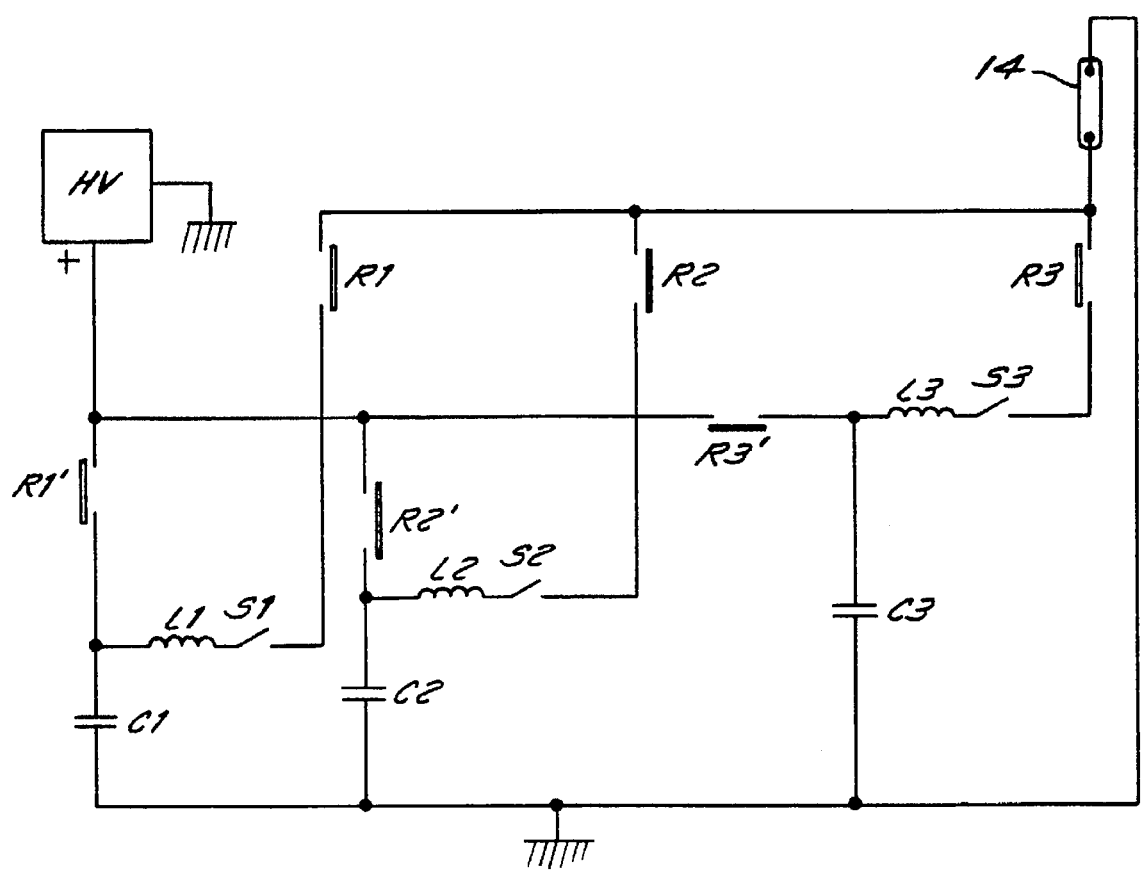
FIG. 3 is a schematic diagram of a pulse forming network with a variable pulse width for use with the skin treatment device of FIGS. 1 and 2.

FIG. 3 shows a variable pulse-width pulse forming circuit comprised of a plurality of individual pulse forming networks (PFN's) that create the variation in pulse-widths of flashlamp 14. The light pulse full width at half maximum (FWHM) of a flashlamp driven by a single element PFN with capacitance C and inductance L is approximately equal to:

$$\Delta t \approx 2[LC]^{1/2} \quad \text{(Eq. 2)}$$

Flashlamp 14 may be driven by three different PFN's, as shown in FIG. 3. The relay contacts R1', R2' and R3' are used to select among three capacitors C1, C2 and C3 that are charged by the high voltage power supply. Relays R1, R2 and R3 are used to select the PFN that will be connected to flashlamp 14. The high voltage switches S1, S2 and S3 are used to discharge the energy stored in the capacitor of the PFN into flashlamp 14. In one embodiment L1, L2 and L3 have values of 100 mH, 1 mH and 5 mH, respectively, and C1, C2 and C3 have values of 100 mF, 1 mF and 10 mF, respectively.

In addition to the possibility of firing each PFN separately, which generates the basic variability in pulse-width, additional variation can be achieved by firing PFN's sequentially. If, for example, two PFN's having pulse-width Δt1 and Δt2 are fired, so that the second PFN is fired after the first pulse has decayed to half of its amplitude, then an effective light pulse-width of this operation of the system will be given by the relation: Δt≈Δt1+Δt2.

The charging power supply typically has a voltage range of 500 V to 5 kV. The relays should therefore be high voltage relays that can isolate these voltages reliably. The switches S are capable of carrying the current of flashlamp 14 and to isolate the reverse high voltage generated if the PFNs are sequentially fired. Solid-state switches, vacuum switches or gas switches can be used for this purpose.

A simmer power supply (not shown in FIG. 3) may be used to keep the flashlamp in a low current conducting mode. Other configurations can be used to achieve pulse-width variation, such as the use of a single PFN and a crowbar switch, or use of a switch with closing and opening capabilities.

Typically, for operation of flashlamp 14 with an electrical pulse-width of 1 to 10 msec, a linear electrical energy density input of 100 to 300 J/cm can be used. An energy density of 30 to 100 J/cm$^2$ can be achieved on the skin for a typical flashlamp bore diameter of 5 mm. The use of a 500 to 650 nm bandwidth transmits 20% of the incident energy. Thus, energy densities on the skin of 6 to 20 J/cm$^2$ are achieved. The incorporation of the fluorescent material will further extend the output radiation in the desired range, enabling the same exposure of the skin with a lower energy input into flashlamp 14.

Pulsed laser skin treatment shows that energy densities in the range of 0.5 to 10 J/cm$^2$ with pulse-widths in the range of 0.5 msec are generally effective for treating vascular related skin disorders. This range of parameters falls in the range of operation of pulsed non-laser type light sources such as the linear flashlamp. A few steps of neutral density glass filters 18 can also be used to control the energy density on the skin.

For external disorders a typical pulse-width of 5 microsecond is used. A 20 J/cm electrical energy density input into a 5 mm bore flashlamp results in an energy density on the skin of 10 J/cm$^2$. Cutting off the hard UV portion of the spectrum results in 90% energy transmission, or skin exposure to an energy density of close to 10 J/cm$^2$. This energy density is high enough to evaporate external marks on the skin.

Device 10 can be provided as two units: a lightweight unit held by a physician using handle 13, with the hand-held unit containing flashlamp 14, filters 18 and iris 20 that together control the spectrum and the size of the exposed area and the detectors that measure the reflectivity and the instantaneous skin temperature. The power supply, the PFN's and the electrical controls are contained in a separate box (not shown) that is connected to the hand-held unit via a flexible cable. This enables ease of operation and easy access to the areas of the skin that need to be treated.

The invention has thus far been described in conjunction with skin treatment. However, using a flashlamp rather than a laser in invasive treatments provides advantages as well. Procedures such as lithotripsy or removal of blood vessel blockage may be performed with a flashlamp. Such a device may be similar to that shown in FIGS. 1 and 2, and may use the electronics of FIG. 3 to produce the flash. However, to properly couple the light to an optical fiber a number of couplers 40, 80 and 90 are shown in FIGS. 4 and 8–10, respectively.

Coupler 40 includes an optical source of high intensity incoherent and isotropic pulsed light such as a linear flash tube 42, a light reflector 44 which delivers the light energy to an optical fiber 46. The latter has a generally conical edge in the embodiment of FIG. 4. Optical fiber 46 transfers the light from light collection system 44 to the treatment area. In general, coupler 40 couples pulsed light from a flash tube into an optical fiber and has applications in medical, industrial and domestic areas.

For example, coupler 40 may be used in material processing to rapidly heat or ablate a portion of a material being processed, or to induce a photo-chemical process. Alternatively, coupler 40 may be used in a photography application to provide a flash for picture taking. Using such a coupler would allow the flash bulb to be located inside the camera, with the light transmitted to outside the camera using an optical fiber. As one skilled in the art should recognize coupler 40 allows the use of incoherent light in many applications that coherent or incoherent light has been used in the past.

To provide for coupling the light to an optical fiber, flash tube 42 has a toroidal shape, shown in FIGS. 5 and 6, and is disposed inside reflector 44. In addition to the toroidal shape other shapes, such as a continuous helix, may be used for flash tube 42. However, a helical tube is more difficult to manufacture than a toroidal tube. Referring now to FIG. 6, flash tube 42 is generally in the shape of a tours, but is not a perfect tours since the electrodes located at the end of the tours have to be connected to the power source. This does not create a significant disturbance in the circular shape of flash tube 42, since the connection to the electrodes can be made quite small.

Reflector 44 collects and concentrates the light, and has a cross-section of substantially an ellipse, in a plane perpendicular to the minor axis of the toroidal flash tube 42. The major axis of this ellipse preferably forms a small angle with the major axis of toroidal lamp 42. The exact value of the angle between the ellipse axis and the main axis of lamp 42 depends on the Numerical Aperture (NA) of the optical fiber. The toroidal flash tube is positioned so that its minor axis coincides with the focus of the ellipse. The other focus of the ellipse is at the edge of optical fiber 46. Reflector 44 may be machined from metal with the inner surfaces polished for good reflectivity. Aluminum is a very good reflector with high reflectivity in the visible and ultraviolet wavelengths, and it may be used for this purpose. The reflector can be machined in one piece and then cut along a surface perpendicular to the main axis of the device. This will enable integration of the toroidal flash tube into the device.

Figure 4:
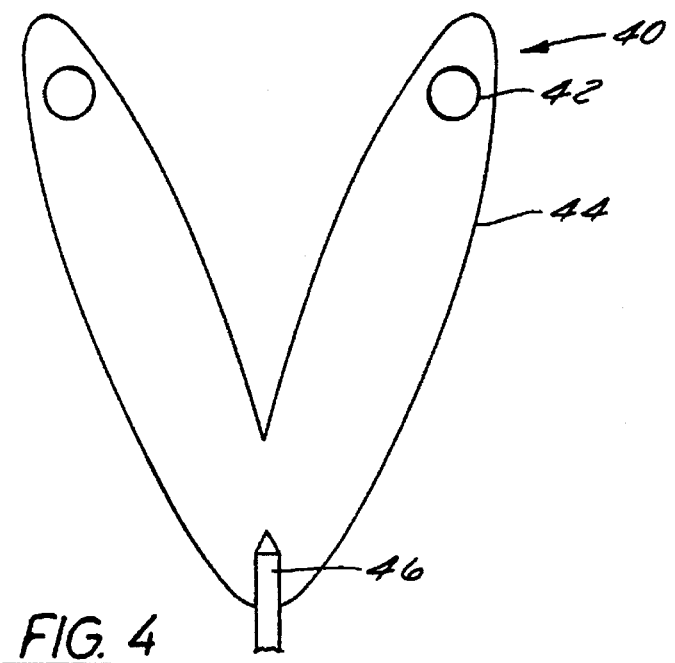
FIG. 4 is a cross-sectional view of a coupler for coupling light from a toroidal flash tube into an optical fiber with a conical edge.

As shown in FIG. 4, the edge of optical fiber 46 is a cone with a small opening angle, so that the total area of the fiber exposed to the light from the flash tube is increased. Referring now to FIG. 7 the geometry for coupling light into a conical tip is shown. It is assumed here that the light comes from a region in space with a refractive index of $n_2$ and that the conical section of the fiber (as well as the rest of the fiber core) has a refractive index of $n_1$.

Not all the light rays hitting the cone are trapped in it. For light rays that propagate in a plane that contains the major axis of the system, a condition can be derived for the angle of a ray that will be trapped and absorbed in the fiber. This condition is shown in Equation 3.

$$\text{Sin}=(\mu_{criti})=\text{Cos}(\beta)-[n_1^2/n_2^2-1]^{1/2}\sin(\beta) \qquad \text{(Eq. 3)}$$

Light will be trapped in the conical portion of the optical fiber if the incidence angle $\mu$ is larger than $\mu_{criti}$ calculated from Equation 3. Trapping is possible only if $n_1>n_2$. If the medium outside of the fiber is air, $n_2=1$. Not all of the light trapped in the conical section of the fiber will also be trapped in the straight portion of the fiber if a fiber with a core and a cladding is used. If a fiber with a core and no cladding is used (air cladding), then all the rays captured in the conical section of the fiber will also be trapped in the straight section of the fiber.

The configuration shown in FIG. 4 can also be used with a fluid filling the volume between the reflector and the optical fiber. A very convenient fluid for this purpose may be water. Water is also very effective in cooling the flashlamp if high repetition rate pulses are used. The presence of a fluid reduces the losses that are associated with glass to air transitions, such as the transition between the flashlamp envelope material and air. If a fluid is used in the reflector volume, then its refractive index can be chosen such that all the rays trapped in the conical section are also trapped in the fiber, even if core/cladding fibers are used.

Another way of configuring the fiber in the reflector is by using a fiber with a flat edge. This configuration is shown in FIG. 8 and has trapping efficiency very close to the trapping efficiency of the conical edge. Many other shapes of the fiber edge, such as spherical shapes, can also be used. The configuration of the fiber edge also has an effect on the distribution of the light on the exit side of the fiber and it can be chosen in accordance with the specific application of the device.

The device may be used with a variety of optical fibers. Single, or a small number of millimeter or sub-millimeter diameter fibers, will typically be used in invasive medical applications. In other applications, particularly in industrial and domestic applications, it may be preferable to use a fiber having a larger diameter, or a larger bundle of fibers, or a light guide.

According to one embodiment flexible or rigid light guides are used to couple the light to the treatment area. Flexible light guides made from a bundle of quartz or other glass fibers that are fused together by heat at the edge of the bundles. The bundles may be circular, rectangular, or any other useful shape. Rigid light guides may be made from quartz, acrylic, glass, or other materials having a high degree of transparency. The material is generally highly polished on all sides.

A typical cross section of a circular light guide useful for therapeutic treatment is one mm to ten mm in diameter. Alternatively, a rectangular light guide may be used having typical dimensions of 3 mm by 10 mm to 30 mm by 100 mm. In either case the length may be 20 to 300 mmm, or as needed for the specific application.

According to another alternative embodiment a rectangular light guide is used to more efficiently couple the light. The rectangular light guide is chosen to have a shape that matches a rectangular linear flashlamp and to match the shape of the vessel being treated.

The light guides described above may be used in another alternative embodiment to control the spectrum of light delivered to the treatment area. Spectral control can be achieved by making the light guide from a material that had an absorbing dye dissolved therein. Thus, light transmitted by the light guide will have a spectrum in as determined by the absorbing dye. Alternatively, a flat, discrete filter may be added to one end (preferably the input end) of the light guide. Both of these filters are absorbing filters. The inventors have found that absorbing filters produced by Schott, having Model Nos. OG515, OG550, OG570, and OG590 have suitable characteristics.

Additionally, interference filters or reflective coatings on the light guide may be used by applying a proper optical coating to the light guide. Again, a single discrete interference filter could also be used. Additionally, combinations of the various filters described herein, or other filters, may be used. The use of the filters described here may render the use of the filters described earlier with reference to FIG. 1 redundant.

An alternative embodiment entails the use of application specific light guides. In this way the spectra of light for various treatments can be easily controlled. According to this alternative each type of treatment will be performed with a specific light guide.

The optical properties of the light guide will be chosen to optimize the particular treatment. The wavelengths below are particularly useful for the respective treatments:

arteries less than 0.1 mm in diameter—520–650 nm veins less than 0.1 mm in diameter—520–700 nm vessels between 0.1 and 1.0 mm in diameter—550–1000 nm larger vessels—600–1000 nm In each case if the skin is darker (higher pigmentation) longer wavelengths on the lower cut-off portion of the spectrum should be used.

Multiple spectra may be used for optimal penetration. This may be accomplished by illuminating with a few pulses, each having a different spectrum. For example, the first pulse can have a spectrum that is highly absorbed in blood. This pulse will coagulate the blood, thereby changing the optical properties of the blood, making it more absorbing in another wavelength range (preferably longer). A second pulse will be more efficiently absorbed since the blood absorbs energy of a greater wavelength range. This principle may be used with lasers or other light sources as well.

In addition to the features of the light guides discussed above, a light guide is used, in one alternative embodiment, to control the angular distribution of the light rays impinging on the skin. Light that impinges on the skin at large angles (relative to the perpendicular) will not penetrate very deeply into the tissue. Conversely, light that impinges perpendicularly to the skin will have a deeper penetration. Thus, it is desirable to provide a distribution of light rays that has a relatively wide angular divergence when the treatment requires shallow penetration. Alternatively, a narrow divergence is preferable for treatment requiring deep penetration is desired. Some treatment might require both shallow and deep penetration.

Figures 15, 16:
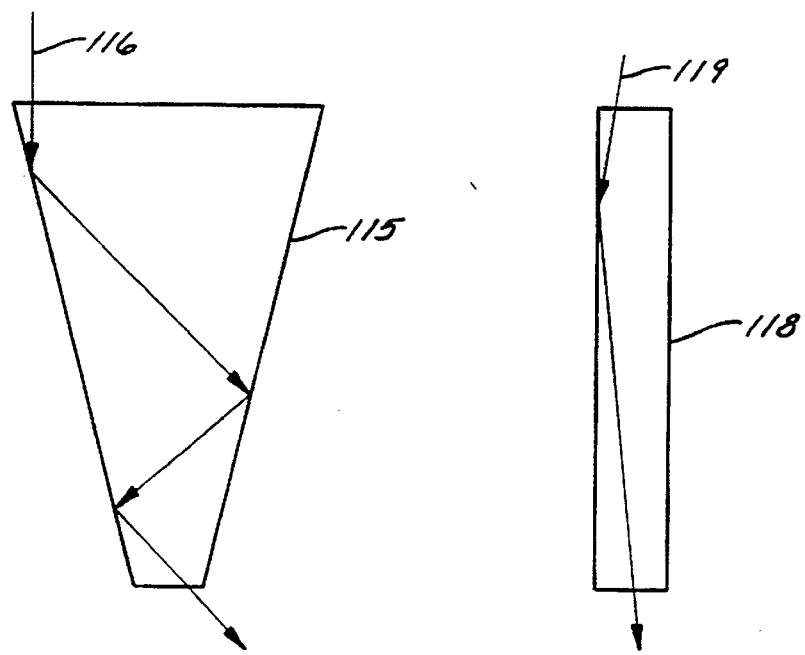
FIG. 15 shows a light guide providing a large angular divergence.
FIG. 16 shows a light guide providing a narrow angular divergence.

FIG. 15 shows a light guide 115 having an exit beam with a greater angular divergence than that of the entrance beam. As shown in FIG. 15, a beam 116 enters light guide 115 at a small angle, relative to the axis of light guide 115. When beam 501 exits light guide 115, the angle, relative to the axis, is much greater. The tapered shape of light guide 115 enhances this divergence.

FIG. 16 shows a straight light guide 118 that maintains the angular distribution of the rays of light that enter into it. A beam 119 is shown entering and exiting light guide 118 with the same angle, relative to the axis of coupler 601. Alternate use of both light guides 115 and 118 can achieve the narrow and deep penetration discussed above. Alternatively, the user can select the type of coupler according to the depth of penetration needed for the treatment being performed.

FIGS. 9 and 10 show a coupler 90 for coupling a linear flash tube 92 through a linear to circular fiber transfer unit 94 to a fiber bundle 96. A reflector 98 has an elliptical cross-section, shown in FIG. 10, in a plane parallel to the axis of linear flash tube 92 in this embodiment. Tube 92 is located on one focus of the ellipse while the linear side of linear to circular bundle converter 94 is located at the other focus of the ellipse. This configuration is relatively simple to manufacture and commercially available linear to circular converters such as 25-004-4 available from General Fiber Optics may be used. This configuration is particularly useful for larger exposure areas of the fiber, or for flash illumination purposes.

The energy and power densities that can be achieved by this invention are high enough to get the desired effects in surface treatment or medical applications. For the embodiment shown in FIG. 4 the total energy and power densities can be estimated as follows. For a typical toroidal lamp with a 4 mm bore diameter and a major diameter of 3.3 cm an electrical linear energy density input of 10 J/cm into the lamp can be used with a 5 μsec pulse width. The light output of the lamp will be 5 to 6 J/cm for optimal electrical operating conditions. For the reflector shown in FIG. 4, 50% of the light generated in the lamp will reach the lower focus. Thus, a total energy flux on the focus of 25 to 30 J may be obtained. For embodiments shown in FIG. 4 or FIG. 8 the total cross-section area of reflector at the focal plane has a cross-section of 0.8 cm$^2$. Energy densities on the order of 30 to 40 J/cm$^2$ at the entrance to the fiber should be attained with this cross-section. This corresponds to power densities of 5 to 10 MW/cm$^2$, which are the typical power densities used in medical or material processing applications.

For longer pulses, higher linear electrical energy densities into the lamp can be used. For a 1 msec pulse to the flash tube a linear electrical energy density of 100 J/cm can be used. The corresponding energy density at the focal area would be up to 300 J/cm$^2$. Such energy densities are very effective in industrial cleaning and processing applications as well as in medical applications.

Alternative embodiments for coupling the optical fiber to an extended light source such as a linear flashlamp are shown in FIGS. 11 and 12. In the embodiment of FIG. 11 an optical fiber 101 is wound around a lamp 102 and a lamp envelope 103. Some of the light that is produced by the light source is coupled into the fiber. If the light rays are propagating in the direction that is trapped by the fiber then this light will propagate in the fiber and it can be used at a fiber output 104. One limitation of this configuration is the fact that most of the light emitted by lamp 103 travels in a direction perpendicular to the surface of lamp 103 and cannot be trapped in fiber 101.

The embodiment shown in FIG. 12 overcomes this problem. A doped optical fiber 105 is wound around lamp 102 and envelope 103, rather than an undoped fiber such as fiber 101 of FIG. 11. The dopant is a fluorescent material which is excited by the radiation emanating from lamp 102 and radiates light inside the fiber. This light is radiated omnidirectionally and the part of it that is within the critical angle of fiber 105 is trapped and propagates through the fiber and can be used at fiber output 104. The angle of light that is trapped in the fiber is the critical angle of the material from which the optical fiber or optical wave guide is made. For a fiber (or optical wave guide) in air this angle is given by sin $\alpha = 1/n$.

Typically for glass or other transparent materials n=1.5 and $\alpha = 41.8°$. This corresponds to a trapping efficiency of more than 10% of the light emitted by fluorescence inside the fiber. If we assume a 50% efficiency of the fluorescence process we find out that more than 5% of the light produced by the lamp is trapped and propagated down the fiber. For example, a 4" lamp with a linear electrical energy input of 300 J/inch and 50% electrical to light conversion efficiency would couple 2.5% of its electrical energy into the fiber. This corresponds, for the 4" lamp case to a total light energy of 30 J of light. This embodiment has the additional advantage of transferring the wavelength emitted by the lamp to a wavelength that may be more useful in some of the therapeutic or processing applications mentioned before. Thus, fluorescent material doped in the fiber can be chosen in accordance with an emission wavelength determined by the specific application of the device.

One alternative embodiment includes the use of a gel to couple the light to the skin. This alternative reduces heating of the outer layer of the skin (the epidermis and upper layers of the dermis). The gel is preferably a high viscosity water based gel and is applied to the skin before treatment, although other gels that are not necessarily water based may be used. A gel having a relatively high heat capacity and thermal conductivity, such as a water based gel, is preferable to enable cooling of the outer skin (the epidermis in particular). Transparency is also desirable because during treatment light passes through the transparent gel and reaches the skin.

Figure 13:
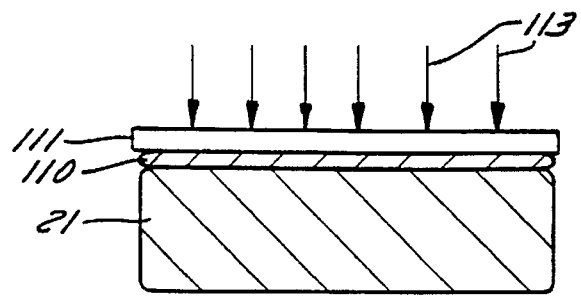
FIG. 13 is a schematic configuration of a gel skin interface with a transparent plate.

Referring now to FIG. 13, a gel 110 is applied to the skin 21 prior to the treatment. A flat layer of gel on top of the skin is used since irregularities in the upper layer of the gel through which the light passes may cause scattering of the light and reduce its penetration into the skin. In order to achieve this flatness a solid, transparent, flat piece 111 may be applied on top of the skin. The configuration is shown schematically in FIG. 13. The transparent plate can be made out of glass or other transparent materials. Either the flashlamp housing or the light guides discussed above may be placed in direct contact with the transparent plate.

Figure 14:
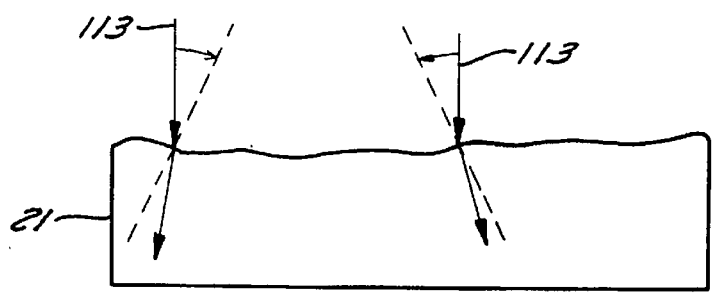
FIG. 14 shows an angular distribution of photons penetrating without using a gel.

The configuration of FIG. 13 has the advantage of reducing the scattering of light (represented by arrows 113) that enters into the skin due to irregularities in the surface of the skin. The skin has an index of refraction that is larger than that of the air. As a result, any photon that impinges on the air skin interface is deflected if it does not hit the skin at an incidence angle of 0°. Since the surface of the skin is irregular the angular distribution of the skin increases. This is shown schematically in FIG. 14.

The use of gel addresses this problem since the gel can fill irregular voids that are created by the skin structure. The transparent plate that covers the gel and the gel itself will preferably have an index of refraction that is close to that of the skin. This is relatively easy since the index of refraction of the skin is of the order of 1.4 in the visible and the near infrared. Most glasses and transparent plastics have indices of refraction that are of the order of 1.5 which is close enough. The index of refraction of water is of the order of 1.34 in this range. Water based gels will have similar indices of refraction. The index can be increased by proper additives. The plate and gel thus act as a flat surface for the light to impinge upon. Because the gel and plate have an index of refraction close to that of the skin there is very little scattering at the gel-plate and gel-skin interfaces.

The use of a gel has been experimentally successful in the treatment of leg veins and other benign vascular lesions of the skin. The treatments were carried out with the flashlamp described above. However, in alternative embodiments a different incoherent source, or a coherent source, may be used.

During operation light is typically applied to the skin in a sequence of three pulses with short delays between the pulses. This mode of operation is used in order to take advantage of the faster cooling of the superficial, thin (less than 0.1 mm thick) epidermis compared to the larger and deeper vessels typical of leg veins. The gel in contact with the skin cools the epidermis during the waiting period between the pulses. This cooling reduces significantly the damage to the epidermis.

In accordance with the invention, light is applied to the treated area in either a long pulse or in a sequence of pulses separated by a delay. The delay and/or pulse length is preferably controlled by the operator to provide enough heat to accomplish the desired treatment but not enough heat to damage the skin.

This concept was tested with large and deep vessels (of the order of 2 mm in diameter and 2 mm deep). A thin layer of commercial water based ultrasound gel (1 to 2 mm thick, "Aqua clear" gel made by Parker USA) was applied on the skin. A 1 mm thin glass window was used to generate a flat layer of the gel. The light from the device passed through the thin glass and the gel and into the skin. Care was taken to assure than no air bubbles exist in the gel. This configuration was tested with photon fluences of 30 to 50 J/cm$^2$. Coagulation and clearance of the vessels was obtained without causing damage to the skin. This is contrary to similar trials in which gel was not used and in which fluences of 20 J/cm$^2$ with the same pulse structure caused burns of the skin.

The epidermis has a thickness of approximately 0.1 mm and a cooling time of about 5 msec. Thus, to avoid burning delays greater than 5 msec are used.

Figure 17:
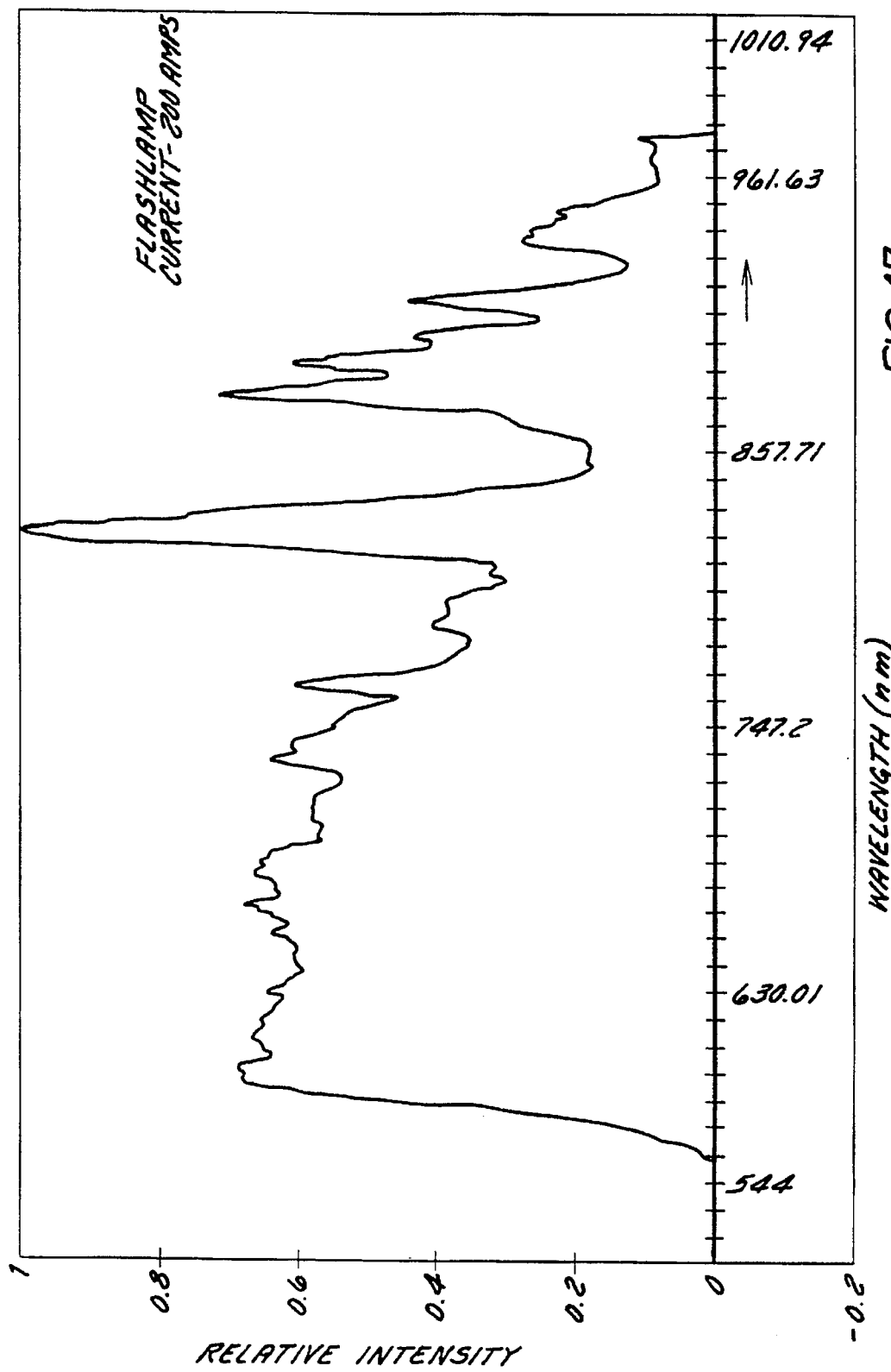
FIG. 17 shows a spectra produced with a flashlamp current of 200 amps.
Figure 18:
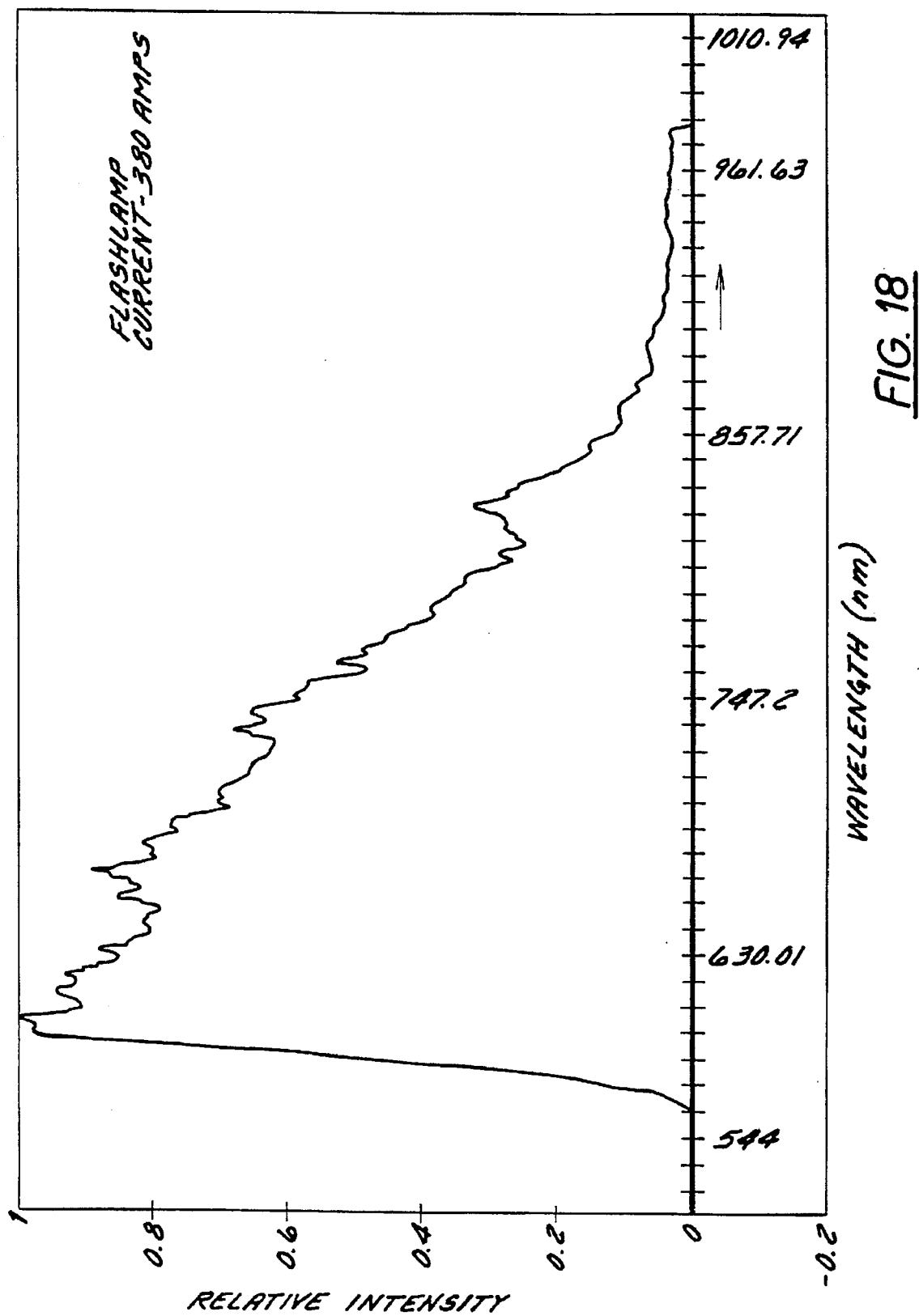
FIG. 18 shows a spectra produced with a flashlamp current of 200 amps.

In another alternative embodiment the spectrum of the light used for treatment is controlled by controlling the voltage and/or current applied to the flashlamp. As is well known in the art, the spectrum of light produced by a flashlamp is dependent on the voltage and current provided to the flashlamp. According to this embodiment the input voltage and current is selected to provide a desired treatment spectrum. The appropriate voltage and currents may be determined experimentally for each flashlamp used. For example, a flashlamp current of 200 amps produced the spectra shown in FIG. 17. Similarly, the spectra of FIG. 18 was produced using a flashlamp current of 380 amps. The spectra of FIG. 17 shows a significant enhancement in the wavelength range of 800–1000 nm. Such a spectra is particularly useful for treatment of large vessels.

The different currents and voltages used to control the output spectra may be obtained using a group or bank of capacitors that are capable of being connected in either series or parallel as part of the power source for the flashlamp. A series connection will provide a relatively high voltage and high current, thereby producing a spectra having energy in a shorter wavelength, such as 500–650 nm. Such a series connection will be more appropriate for generating shorter pulses (1 to 10 msec, e.g.) useful for treatment of smaller vessels.

A parallel connection provides a lower current and voltage, and thus produces an output spectra of a longer wavelength, such as 700–1000 nm. Such a spectra is more appropriate for treatment of larger vessels and is suitable for producing longer pulses (in the range of 10–50 msec, e.g.). The selection of series or parallel connections may be done using a relay or sets of relays.

Figure 19:
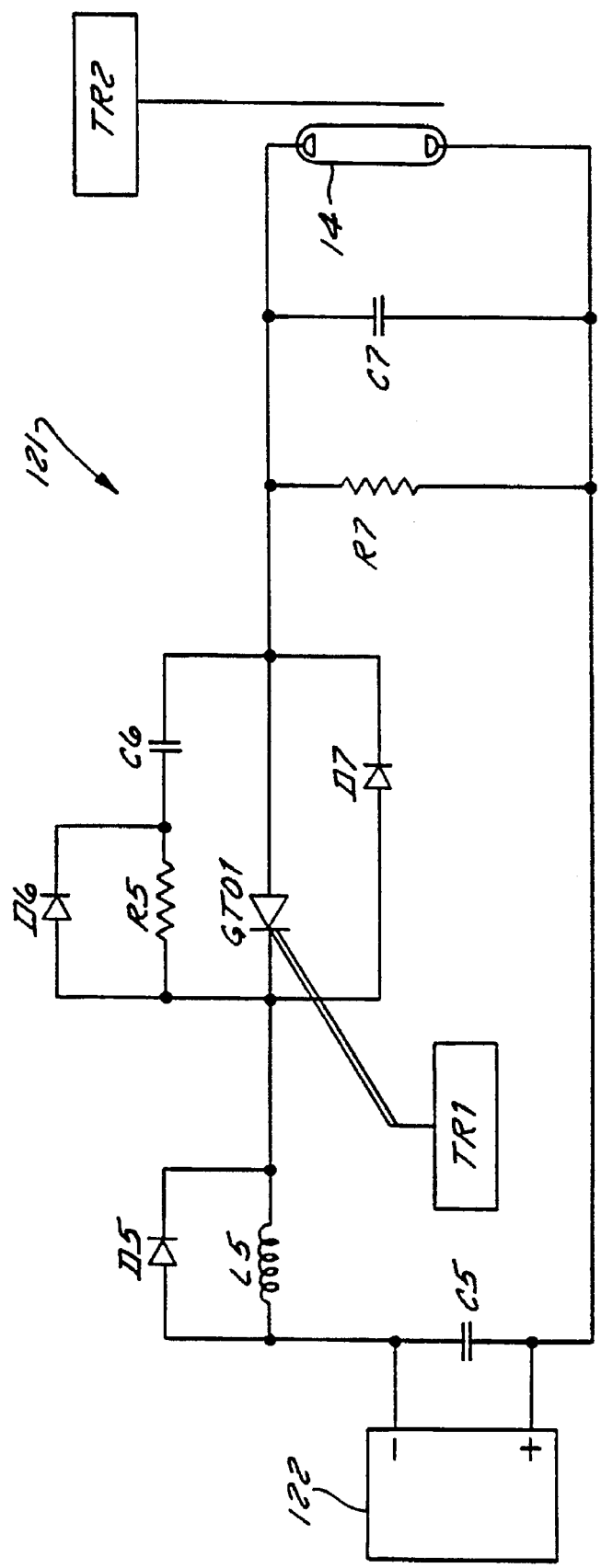
FIG. 19 shows a GTO driver circuit for a flashlamp.

In one alternative embodiment the pulse forming network of FIG. 3 is replaced by a GTO driver circuit 121, such as that shown in FIG. 19. The driver circuit of FIG. 19 uses a switch capable of being turned both on and off to control the application of power to the flashlamp. While this alternative embodiment will be described with respect to a GTO being used as the switch, other switches capable of being turned both on and off, such as IGBTs, may also be used.

Referring now to FIG. 19, driver circuit 121 includes a high voltage source 122, a capacitor bank C5, an inductor L5, a diode D5, a switch GTO1, a diode D6, a diode D7, a resistor R5, a capacitor C6, a GTO trigger generator TR1, a resistor R7, a capacitor C7 and a flashtube trigger generator TR2. These components are connected to flashlamp 14 and serve to provide the power pulses to flashlamp 14. The duration and timing of the pulses are provided in accordance with the description herein. Driver 121 operates in the manner described below.

High voltage source 122 is connected across capacitor bank C5, and charges capacitor bank C5 to a voltage suitable for application to flashlamp 14. Capacitor bank C5 may be a comprised of one or more capacitors, and may be configured in the manner described above.

Prior to illumination of flashlamp 14 flashtube trigger generator TR2 breaks down flashlamp 14 and creates a relatively low impedance channel therein. After the flashlamp breaks down, capacitor C7 dumps current into flashlamp 14, further creating a low impedance channel in flashlamp 14. In this manner a pre-discharge is provided that prepares flashlamp 14 for the power pulse. Capacitor C7 provides a small amount of current, relative to capacitor bank C5. Alternatively, driver circuit 121 may operate in a simmer mode, wherein the pre-discharge is not necessary.

Thereafter, switch GTO1 is turned on via a pulse from GTO trigger generator TR1, completing the circuit between flashlamp 14 and capacitor bank C5. Thus, capacitor bank C5 discharges through flashlamp 14. An inductor L5 may be provided to control the rise time of the current through flashlamp 14. Inductor L5 may include an inherent resistive component, not shown.

After a length of time determined by the desired pulse width has passed, GTO trigger generator TR1 provides a pulse to switch GTO1, turning it off. A control circuit determines the timing of the trigger pulses and provides them in accordance with the desired pulse widths and delays.

A snubber circuit comprised of diode D6, resistor R5, and a capacitor C6 is provided for switch GTO1. Also, diodes D5 and D7 are provided to protect switch GTO1 from reverse voltages. Resistor R7 is provided in parallel with flashlamp 14 to measure the leakage current of switch GTO1, which can in turn be used to make sure that switch GTO1 is operating properly.

A possible addition to driver circuit 121 is to provide an SCR or other switch in parallel with capacitor bank C5. This allows the discharge or resetting of capacitor bank C5 without turning on switch GTO1. Other modifications may be made, such as providing the circuit with a serial trigger, rather than the parallel trigger shown. Another modification is to use the driver circuit with a laser rather than flashlamp 14.

Proper use of pulse widths and delays can aid in avoiding burning the epidermis. The epidermis has a cooling time of about 5 msec, while large vessels have a longer cooling time (a 1 mm vessel has a cooling time of about 300 msec). Thus, during a pulse of duration longer than 5 msec the epidermis can cool down but the vessel will not. For example, for treatment of a large vessel (such as one having a diameter of about 1 mm) a pulse of 100 msec will allow the skin to cool, but the vessel will not cool.

The same effect may be achieved using trains of pulses. This is useful when it is not practical to provide a single long pulse to the flashlamp. The delays between pulses are selected to allow the skin to cool, but to be too short for the vessel to cool. Thus, larger vessels can be treated with longer delays because they have greater cooling times. Small vessels cool quickly and long delays are not effective. However, they also need less energy and can be treated effectively in a single pulse.

Typical delay times are in the range of 20 msec to 500 msec. More specifically, delays of between 100–500 msec are effective for vessels larger than 1 mm in diameter. Delays of between 20–100 msec are effective for vessels between 0.5 and 1 mm in diameter. Delays of between 10–50 msec are effective for vessels between 0.1 and 0.5 mm in diameter. A single pulse having a width in the range of 1 msec to 20 msec is effective for vessels less than 0.1 mm diameter.

Additionally, delays should be selected according to skin pigmentation. Darker skin absorbs more energy and needs more time to cool: thus longer delays are needed. Lighter skin absorbs less energy and can accommodate shorter delays.

It has been found that multiple pulses avoids "purpora" or the explosion of small vessels in or close to the skin. The use of pulses to avoid burning and provide cooling will be effective for light provided by lasers or other sources as well.

Another alternative embodiment includes the use of a microprocessor or personal computer to control the flashlamp. The microprocessor can be used to provide the timing functions and prompt the trigger signals described above. Additionally, in one embodiment the microprocessor includes a user interface, such as a screen and keyboard, buttons, mouse, or other input device. The microprocessors have information stored therein that aids in the selection of treatment parameters.

For example, if the condition being treated is a port wine stains skin type III, the physician inputs that condition into the microprocessor. The microprocessor responds with suggested treatment parameters, such as using a 570 nm cut-off filter, a double pulse with a delay of 50 msec and a fluence of 55 J/cm$^2$. The physician can alter these suggested parameters, but need not refer back to operating guidelines for suggested parameters.

The microprocessor or personal computer can also be used to create and store patient information in a database. Thus, past treatment information such as condition being treated, treatment parameters, number of treatments, etc. is stored and may be recalled when the patient is again treated. This aids in providing the proper treatment to the patient. Additionally, the database may include photographs of the patient's condition before and after each treatment. Again, this aids in record keeping and determining what treatments are most successful for given conditions.

In addition to the treatments described above the devices and methods described herein may be used to treat other conditions. For example, psoriasis and warts have been successfully treated. Similarly, skin rejuvenation (treating wrinkles) should be effective. The inventor further contemplates using this invention to treat hemorrhoids, throat lesions, and gynecological problems associated with vascular malformations.

Thus, it should be apparent that there has been provided in accordance with the present invention a flashlamp and coupler that fully satisfy the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

I claim:

1. A therapeutic treatment device for coagulating blood in blood vessels underlying an epidermal layer comprising an incoherent light source operable to provide a pulsed light output for coagulation blood and a driver circuit, including a switch capable of being electrically turned on and being electrically turned off to thereby provide a first interval of light, connected to the light source to control the pulse width and delay between pulses.

2. The treatment device of claim 1 further comprising a housing with an opening, said light source being disposed in said housing, and said housing is adapted to be disposed adjacent a skin treatment area, and wherein the switch is a GTO.

3. The therapeutic treatment device of claim 1, wherein the switch and driver circuit limit the first interval to a predetermined duration of less than 100 milliseconds.

4. The therapeutic treatment device of claim 3, wherein the incoherent light source provides an incoherent light output having an energy fluence of between 6 and 300 J/cm$^2$ during the first interval.

5. The therapeutic treatment device of claim 4, wherein the incoherent light source provides an incoherent light output of between 6 and 20 J/cm$^2$ during the first interval.

6. The therapeutic treatment device of claim 5, further including a light guide having a cross-sectional area of no less than 0.3 cm$^2$ which couples the light output to the epidermal layer.

7. The therapeutic treatment device of claim 6, wherein the light guide has a rectangular cross-section of between 3 and 30 millimeters in width and 10 and 100 millimeters in length.

8. The therapeutic treatment device of claim 4 wherein the incoherent light source provides an incoherent light output of between 30 and 100 J/cm$^2$ during the first interval.

9. The therapeutic treatment device of claim 1, wherein the light source is a flashtube, and further comprising a first capacitor electrically coupled to the switch, wherein the switch electrically connects and disconnects the capacitor to the light source.

10. The therapeutic treatment device of claim 9 further comprising a second capacitor operable to be alternately coupled both in series and in parallel to the first capacitor.

* * * * *

EX PARTE REEXAMINATION CERTIFICATE (6682nd)
United States Patent
Eckhouse

(10) Number: US 5,626,631 C1
(45) Certificate Issued: Mar. 3, 2009

(54) METHOD AND APPARATUS FOR THERAPEUTIC ELECTROMAGNETIC TREATMENT

(75) Inventor: Shimon Eckhouse, Haifa (IL)

(73) Assignee: Lumenis, Ltd., Yokneam (IL)

Reexamination Request:
No. 90/010,069, Dec. 5, 2007
No. 90/010,134, Apr. 4, 2008

Reexamination Certificate for:
Patent No.: 5,626,631
Issued: May 6, 1997
Appl. No.: 08/383,509
Filed: Feb. 3, 1995

Related U.S. Application Data

(63) Continuation-in-part of application No. 07/964,210, filed on Oct. 20, 1992, now Pat. No. 5,405,368.

(51) Int. Cl.
*A61N 5/06* (2006.01)

(52) U.S. Cl. ............................................. 607/88; 606/9
(58) Field of Classification Search ........................ None
See application file for complete search history.

(56) References Cited

U.S. PATENT DOCUMENTS

| | | | |
|---|---|---|---|
| 2,716,698 A | 8/1955 | Brukner | 240/1 |
| 2,954,771 A | 10/1960 | Boyan | 128/396 |
| 3,327,712 A | 6/1967 | Kaufman et al. | 128/398 |
| 3,693,623 A | 9/1972 | Harte et al. | 128/303.1 |
| 3,834,391 A | 9/1974 | Block | 128/303.1 |
| 3,930,504 A | 1/1976 | de Laforcade | 128/303.1 |
| 4,229,658 A | 10/1980 | Gonser | 250/504 H |
| 4,233,493 A | 11/1980 | Nath | 219/354 |
| 4,283,661 A | 8/1981 | Doty | 315/360 |
| 4,298,005 A | 11/1981 | Mutzhas | 128/396 |
| 4,321,930 A | 3/1982 | Jobsis et al. | 128/633 |
| 4,366,570 A | 12/1982 | Bees | 372/70 |
| 4,380,240 A | 4/1983 | Jobsis et al. | 128/633 |
| 4,388,924 A | 6/1983 | Weissman et al. | 128/303.1 |
| 4,444,190 A | 4/1984 | Mutzhas | 128/396 |
| 4,497,018 A | 1/1985 | Rice | 363/96 |
| 4,506,196 A | 3/1985 | Bees | 315/241 R |
| 4,539,987 A | 9/1985 | Nath et al. | 128/303.1 |
| 4,560,883 A | 12/1985 | Kerschgens | 250/504 |
| 4,564,011 A | 1/1986 | Goldman | 128/303.1 |
| 4,645,980 A | 2/1987 | Yang | 315/159 |
| 4,647,830 A | 3/1987 | Bees | 320/1 |
| 4,653,495 A | 3/1987 | Nanaumi | 128/303.1 |
| 4,672,969 A | 6/1987 | Dew | 128/397 |
| 4,726,377 A | 2/1988 | Jegers et al. | 128/376 |

(Continued)

FOREIGN PATENT DOCUMENTS

| | | |
|---|---|---|
| DE | 27 17 421 A1 | 11/1978 |
| JP | 4-90360 | 8/1992 |
| SE | 465 953 B | 11/1991 |
| WO | WO 89/00871 | 2/1989 |
| WO | WO 90/14836 | 12/1990 |
| WO | WO 91/15264 | 10/1991 |
| WO | WO 98/52645 | 11/1998 |

OTHER PUBLICATIONS

Gros, et al, Diaphanologie Mammaire, Memoires Originaux, *J. Radiol. Electrol.*, 53(4):297–306 (1972), in French, with English translation.

Brochure for an Infrared Coagulator by Redfield Corporation (1968).

(Continued)

*Primary Examiner*—Beverly M. Flanagan

(57) ABSTRACT

A therapeutic treatment device for coagulating blood in blood vessels underlying an epidermal layer is disclosed having an incoherent light source operable to provide a pulsed light output for treatment and a driver circuit, including a switch capable of being electrically turned on and being electrically turned off to thereby provide a first interval of light, connected to the light source to control the pulse width and delay between pulses.

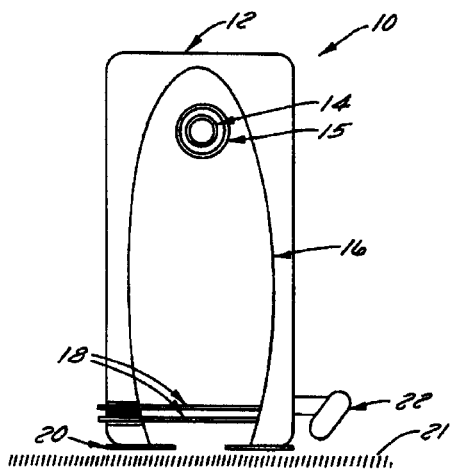

U.S. PATENT DOCUMENTS

| | | | | |
|---|---|---|---|---|
| 4,729,375 | A | 3/1988 | Jegers et al. | 128/376 |
| 4,733,660 | A | 3/1988 | Itzkan | 128/303.1 |
| 4,775,361 | A | 10/1988 | Jacques et al. | 604/20 |
| 4,810,658 | A | 3/1989 | Shanks et al. | 436/172 |
| 4,829,262 | A | 5/1989 | Forumoto | 330/4.3 |
| 4,835,749 | A | 5/1989 | Welton | 368/10 |
| 4,839,562 | A | 6/1989 | Francis et al. | 315/149 |
| 4,851,738 | A | 7/1989 | Yang | 315/159 |
| 4,871,559 | A | 10/1989 | Dunn et al. | 426/248 |
| 4,884,568 | A | 12/1989 | Hahn | 128/303.1 |
| 4,930,504 | A | 6/1990 | Diamantopoulos et al. | 128/395 |
| 4,938,221 | A | 7/1990 | Tuffel | 128/401 |
| 4,947,859 | A | 8/1990 | Brewer et al. | 128/715 |
| 5,008,579 | A | 4/1991 | Conley et al. | 310/303 |
| 5,020,995 | A | 6/1991 | Levy | 433/215 |
| 5,034,235 | A | 7/1991 | Dunn et al. | 426/238 |
| 5,039,867 | A | 8/1991 | Nishihara et al. | 250/492.3 |
| 5,054,488 | A | 10/1991 | Muz | 128/633 |
| 5,059,192 | A | 10/1991 | Zaias | 606/9 |
| 5,066,293 | A | 11/1991 | Furumoto | 606/9 |
| 5,071,422 | A | 12/1991 | Watson et al. | 606/128 |
| 5,083,093 | A | 1/1992 | Adler et al. | 328/65 |
| 5,113,462 | A | 5/1992 | Clancy et al. | 385/53 |
| 5,125,922 | A | 6/1992 | Dwyer et al. | 606/3 |
| 5,126,621 | A | 6/1992 | Morton et al. | 313/237 |
| 5,194,723 | A | 3/1993 | Cates et al. | 250/205 |
| 5,204,517 | A | 4/1993 | Cates et al. | 250/205 |
| 5,226,107 | A | 7/1993 | Stern et al. | 392/416 |
| 5,269,778 | A | 12/1993 | Rink et al. | 606/12 |
| 5,281,798 | A | 1/1994 | Hamm et al. | 250/205 |
| 5,282,797 | A | 2/1994 | Chess | 606/9 |
| 5,290,273 | A | 3/1994 | Tan | 606/9 |
| 5,290,274 | A | 3/1994 | Levy et al. | 606/13 |
| 5,312,395 | A | 5/1994 | Tan et al. | 606/9 |
| 5,320,618 | A | 6/1994 | Gustafsson | 606/9 |
| 5,328,488 | A | 7/1994 | Daikuzono | 606/16 |
| 5,328,517 | A | 7/1994 | Cates et al. | 134/7 |
| 5,334,190 | A | 8/1994 | Seiler | 606/5 |
| 5,337,741 | A | 8/1994 | Diamond | 600/8 |
| 5,344,418 | A | 9/1994 | Ghaffari | 606/9 |
| 5,344,433 | A | 9/1994 | Talmore | 607/88 |
| 5,374,265 | A | 12/1994 | Sand | 606/5 |
| 5,400,791 | A | 3/1995 | Schlier et al. | 128/664 |
| 5,423,803 | A | 6/1995 | Tankovich et al. | 606/9 |
| 5,445,146 | A | 8/1995 | Bellinger | 607/89 |
| D363,349 | S | 10/1995 | Dittert | D24/158 |
| 5,474,528 | A | 12/1995 | Meserol | 604/20 |
| 5,489,279 | A | 2/1996 | Meserol | 604/290 |
| 5,522,814 | A | 6/1996 | Bernaz | 606/36 |
| 5,546,214 | A | 8/1996 | Black et al. | 359/203 |
| 5,558,666 | A | 9/1996 | Dewey et al. | 606/9 |
| 5,595,568 | A | 1/1997 | Anderson et al. | 606/9 |
| 5,618,284 | A | 4/1997 | Sand | 606/5 |
| 5,725,565 | A | 3/1998 | Smith | 607/88 |
| 5,755,753 | A | 5/1998 | Knowlton | 607/98 |
| 5,814,040 | A | 9/1998 | Nelson et al. | 606/9 |
| 5,817,089 | A | 10/1998 | Tankovich et al. | 606/9 |
| 5,817,090 | A | 10/1998 | Abergel et al. | 606/9 |
| 5,843,143 | A | 12/1998 | Whitehurst | 607/88 |
| RE36,634 | E | 3/2000 | Ghaffari | 606/9 |
| 6,171,332 | B1 | 1/2001 | Whitehurst | 607/89 |

OTHER PUBLICATIONS

Achauer et al., "Argon Laser Treatment of Telangiectasia of the Face and Neck: 5 Years' Experience", *Lasers Surg. Med.*, 7:495–498 (1987).

Alora et al., "Recent Developments in Cutaneous Lasers", *Lasers Surg. Med.*, 26:108–118 (2000).

Alster et al., "Treatment of Port–Wine Stains with the Flashlamp–pumped Pulsed Dye Laser: Extended Clinical Experience in Children and Adults", *Ann. Plast. Surg.*, 32(5):478–484 (1994).

Altshuler et al., "Extended Theory of Selective Photothermolysis", *Lasers Surg. Med.*, 29:416–432 (2001).

Ambrose et al., "Prospective randomized comparison of photocoagulation and rubber band ligation in treatment of haemorrhoids", *Br. Med. J.*, 286:1389–1391 (1983).

Anderson et al., "Mechanisms of Selective Vascular Changes Caused by Dye Lasers",*Lasers Surg. Med.*, 3:211–215 (1983).

Anderson et al., "Microvasculature Can Be Sensitively Damaged Using Dye Lasers: A Basic Theory and Experimental Evidence in Human Skin", *Lasers Surg. Med.*, 1:263–276 (1981).

Anderson et al., "Selective Photothermolysis: Precise Microsurgery by Selective Absorption of Pulsed Radiation", *Science*, 220:524–527 (1983).

Anderson, T.F., "Light Sources in Photomedicine", in *Clinical Photomedicine*, Chapter 3, pp. 37–58, Marcel Dekker, Inc., New York (1993).

Angermeier, M.C., "Treatment of facial vascular lesions with intense pulsed light",*J. Cutan. Laser Ther.*, 1:95–100 (1999).

Anvari et al., "Selective cooling of biological tissues: application for thermally mediated therapeutic procedures", *Phys. Med. Biol.*, 40:241–252 (1995).

Apfelberg et al., "Comparison of Argon and Carbon Dioxide Laser for Treatment of Decorative Tattoos Clinical and Pathological Observations", *Lasers Surg. Med.*, 3:183 (Abstract No. 294) (1983).

Apfelberg et al., Dot or Pointillistic Method for Improvement in Results of Hypertrophic Scarring in the Argon Laser Treatment of Portwine Hemangioamas,*Lasers Surg. Med.*, 6:552–558 (1987).

Apfelberg et al., "Investigation of YAG Laser Uses in Plastic Surgery", *Lasers Surg.*, 6:246 (Abstract No. 77) (1986).

Apfelberg et al., "Preliminary Investigation of KTP/532 Laser Light in the Treatment of Hemangiomas and Tattoos", *Lasers Surg. Med.*, 6:38–42 (1986).

Apfelberg et al., "Progress Report on Extended Clinical Use of the Argon Laser for Cutaneous Lesions", *Lasers Surg. Med.*, 1:71–83 (1980).

Apfelberg et al., "Progress Report on Multicenter Study of Laser–Assisted Liposuction", *Aesth. Plast. Surg.*, 18:259–264 (1994).

Apfelberg et al., "Results of Argon and CO2 Laser Exposure of Telangiectasia of the Lower Extremiity: A Preliminary Report", *Lasers Surg. Med.*, 3:149 (Abstract No. 165) (1983).

Apfelberg et al., "Study of Three Laser Systems for Treatment of Superficial Varicosities of the Lower Extremity", *Lasers Surg. Med.*, 7:219–223 (1987).

Apfelberg et al., "Superpulse $CO_2$ Laser Treatment of Facial Syringomata", *Lasers Surg. Med.*, 7:533–537 (1987).

Apfelberg et al., "Update on Laser Usage in Treatment of Decorative Tattoos", *Lasers Surg. Med.*, 2:169–177 (1982).

Apfelberg, D.B., "Intralesional Laser Photocoagulation—Steroids as an Adjunct to Surgery for Massive Hemangiomas and Vascular Malformations",*Ann. Plast. Surg.*, 35:144–148 (1995).

Ara et al., "Irradiation of Pigmented Melanoma Cells with High Intensity Pulsed Radiation Generates Acoustic Waves and Kills Cells", *Lasers Surg. Med.*, 10:52–59 (1990).

Ashinoff et al., "Cappillary Hemangiomas and Treatment with the FlashLamp–Pumped Pulsed Dye Laser", *Arch. Dermatol.*, 127:202–205 (1991).

Ashinoff et al., "Flashlamp–pumped pulsed dye laser for port–wine stains in infancy: Earlier versus later treatment", *J. Am. Acad. Dermatol.*, 24:467–472 (1991).

Bell et al.,. "100 µsec pulsed $CO_2$ laser resurfacing of lower eyelids: Erythema and rhytides reduction", *SPIE*, 2970:360–366 (1997).

Broska et al., "Comparison of the Argon Tunable Dye Laser with the Flashlamp Pulsed Dye Laser in Treatment of Facial Telangiectasia", *J. Dermatol. Surg. Oncol.*, 20:749–753 (1994).

Brugmans et al., "Temperature Response of Biological Materials to Pulsed Non–Ablative $CO_2$ Laser Irradiation", *Lasers Surg. Med.*, 11:587–594 (1991).

Burson et al., "Gel de Transmision de Ultrasonidos: Estudio Comparitivo de Distintas Formulaciones", *Farm Hosp.*, pp. 394–399 (1991) (in Spanish, with English Abstract Only).

Cates, M.C., "A long pulse (5 µs) e–beam pumped XeF laser", *SPIE*, 1225:34–43 (1990).

Cates, M.C., "Excimer laser produced plasma studies", *SPIE*, 1279:102–111 (1990).

Chess et al., "Cool Laser Optics Treatment of Large Telangiectasia of the Lower Extremities", *J. Dermatol. Surg. Oncol.*, 19:74–80 (1993).

Chissler et al., "Tanning Beds Are Not Without Drawbacks", *FDA Consumer*, pp. 21–22 (1984).

Cliff et al., "Treatment of mature port wine stains with the PhotoDerm VL",*J. Cutan. Laser Ther.*, 1:101–104 (1999).

Cole–Beuglet et al., "Ultrasound mammography for the Augmented Breast",*Radiology*, 146:737–742 (1983).

Colver et al., "Port Wine Stains", *J. Roy. Soc. Med.*, 80:603 (1987).

Colver et al., "Precise dermal damage with an infrared coagulator", *Br. J. Dermatol.*, 114:603–608 (1986).

Colver et al., "Tattoo removal using infra–red coagulation", *Br. J. Dermatol*, 112:481–485 (1985).

Colver G.B., "The Infrared Coagulator in Dermatology", *Dermatologic Clinics*, 7(1):155–167 (1989).

Daniell et al., "A History of Photodynamic Therapy",*Aust. N. Z. J. Surg.*, 61:340–348 (1991).

Denham et al., "Light Distribution in Laser Irradiate Tissue", *Lasers Surg. Med.*, 5:141 (Abstract No. 21) (1985).

Dzubow et al., "Leg Veins and Stretch Marks", *Am. Soc. Dermatol. Surg.*, 22:321 (1996).

Efthymiopoulos et al., "High–energy Short–pulse Flashlamps: Operating Characteristics", *Applied Optics*, 16:70–75 (1977).

Ell et al., "Laser Lithotripsy of Gallstone by Means of a Pulsed Neodymium YAG Laser—In Vitro and Animal Experments", *Endoscopy*, 18:92–94 (1986).

Englehardt et al., "Spectroscopy During Laser Induced Shock Wave Lithotripsy",*SPIE*, 906:200–204 (1988).

Fitzpatrick et al., "Flashlamp–pumped Pulsed Dye Laser Treatment of Port–Wine Stains", *J. Dermatol. Surg. Oncol.*, 20:743–748 (1994).

Fitzpatrick et al., "Treatment of Leg Veins: A Comparison of Laser Therapy with a Noncoherent Multiwave Light Source", *Proc. Ann. Meeting IEEE Lasers & Electro–Optics Soc*, pp. 238–239 (1993).

Flock et al., "Er:YAG Laser–Induced Changes in Skin In Vivo And Transdermal Drug Delivery", *SPIE*, 2970:374–379 (1997).

Flock et al., "Thermal Damage of Blood Vessels in Rat Skin–flap Window Chamber Using Indocyanine Green and a Pulsed Alexandrite Laser: A Feasibility Study", *Lasers Med. Sci.*, 8:185–196 (1993).

Foster et al., "The Successful Use of the PhotoDerm VL in the Treatment of a Cavernous Hemangioma in a Dark–Skinned Infant", *Minimally Invasive Surgical Nursing*, 10:102–104 (1996).

Garden et al., "Effect of Dye Laser Pulse Duration on Selective Cutaneous Vascular Injury",*J. Invest. Dermatol.*, 87(5):653–657 (1986).

Garden et al., "The Treatment of Port–wine Stains by the Pulsed Dye Laser: Analysis of Pulse Duration and Long–term Therapy", *Arch. Dermatol.*, 124:889–896 (1988).

Geronemus et al., "The Medical Necessity of Evaluation and Treatment of Port–Wine Stains", *J. Dermatol. Surg. Oncol.*, 17:76–79 (1991).

Gijsbers et al., "CW Laser Ablation Velocities as a Function of Absorption in an Experimental One–Dimensional Tissue Model", *Lasers Surg. Med.*, 11:287–296 (1991).

Gijsbers et al., "Effect of Force on Ablation Depth for a XeCL Excimer Laser Beam Delivered by an Optical Fiber in Contact with Arterial Tissue Under Saline", *Lasers Surg. Med.*,12:576–584 (1992).

Gilbert, D.J., "Incorporating Photodynamic Therapy Into a Medical and Cosmetic Dermatology Practice", *Dermatol. Clin.*, 25:111–118 (2007).

Gold et al., "5–Aminolevulinic Acid Photodynamic Therapy: Where We Have Been and Where We Are Going", *Dermatol. Surg.*, 30:1077–1084 (2004).

Gold et al., "One–Year Follow–Up Using an Intense Pulsed Light Source for Long–Term Hair Removal", *J. Cutan. Laser Ther.*, 1:167–171 (1999).

Gold et al., "Treatment of Wrinkles and Skin Tightening Using Aluma ™ Skin Renewal System with FACES™ (Functional Aspiration Controlled Electrothermal Stimulation) Technology",*Aesthetic Buyers Guide*, pp. 1–6 (2005).

Gold, M.H., "Aminolevulinic Acid Photodynamic Therapy: Medical Evidence for Its Expanded Use", *Expert Rev. Med. Devices*, 3:357–371 (2006).

Gold, M.H., "Introduction to Photodynamic Therapy: Early Experience",*Dermatol. Clin.*, 25:1–4 (2007).

Goldberg et al., "Nonablative Treatment of Rhytids With Intense Pulsed Light", *Lasers Surg. Med.*, 26:196–200 (2000).

Goldberg et al., "Q–switched Nd:YAG Laser: Rhytid Improvement by Non–Ablative Dermal Remodeling", *J. Cutan. Laser Ther.*, 2:157–160 (2000).

Goldberg, D.J., "Effect of Temperature–Controlled Cooling on Light–Based Skin Treatments", *J. Cos. Laser Ther.*, 8:155–156 (2006).

Goldberg, D.J., "Erbium: YAG Laser Resurfacing: What Is Its Role?", *Aesth. Surg. J.*, 18(4):255–260 (1998).

Goldberg, D.J., "New Collagen Formation After Dermal Remodeling with an Intense Pulsed Light Source", *J. Cutan. Laser Ther.*, 2:59–61 (2000).

Goldman et al., "600 nm Flash Pumped Dye Laser for Fragile Telangiectasia of the Elderly",*Lasers Surg. Med.*, 13:227–233 (1993).

Goldman et al., "Photothermal Sclerosis of Leg Veins", *Dermatol. Surg.*, 22:323–330 (1996).

Goldman et al., "Pulsed dye laser treatment of telangiectases with and without subtherapeutic sclerotherapy", *J. Am. Acad. Dermatol.*, 23(1):23–30 (1990).

Goldman et al., "Treatment of Cutaneous Vascular Lesions", in *Cutaneous Laser Surgery*, Chapter 2, pp. 99–105 (1994).

Goldman et al., "Treatment of port–wine stains (capillary malformation) with the flashlamp–pumped pulsed dye laser", *J. Pediatrics*, 122(1):71–77 (1993).

Goldman, M.P., "Laser and Noncoherent Pulsed Light Treatment of Leg Telangiectasia and Venules", *Cos. Dermatol.*, 8(10):43–44 (1995).

Goldman, M.P., "Sclerotherapy Treatment for Varicose and Telangiectatic Leg Veins", in *Vascular and Pigmented Abnormalities*, Chapter 17, pp. 256–271 (1997).

Gomer, H., "Military laser burns away skin flaws", *The London Sunday Times*, No. 8929 (Oct. 15, 1995).

Gonzalez et al., "Treatment of telangiectases and other benign vascular lesions with the 577 nm pulsed dye laser", *J. Am. Acad. Dermatol.*, 27(2):220–226 (1992).

Gregory et al., "Effect of Blood Upon the Selective Ablation of Atherosclerotic Plaque with a Pulsed Dye Laser", *Lasers Surg. Med.*, 10:533–543 (1990).

Grevelink et al., "Update on the Treatment of Benign Pigmented Lesions with the Q–Switched Ruby Laser", *Lasers Surg. Med.*, 4:73–74 (Abstract No. 326) (1992).

Groot et al., "Comparision of the infrared coagulator and the carbon dioxide laser in the removal of decorative tattoos", *J. Am. Acad. Dermatol.*, 15:518–522 (1986).

Gustafsson et al., "A Variable Pulsewidth Vascular System for Dermatology",*SPIE*, 2128:188–196 (1994).

Guttman, C., "Novel radiofrequency–based treatment achieves skin tightening with minimal discomfort", http://www.modernmedicine.com, pp. 1–3 (2005).

Harris et al., "Facial skin resurfacing with a very short pulsed $CO_2$ laser: Beam characterization and initial histological results", *SPIE*, 2671:211–218 (1996).

Henderson, B.W., "Photodynamic therapy—coming of age", *Photodermatology*, 6:200–211 (1989).

Henning et al., "Clinical and Histological Evaluation of Portwine Stain Treatment with a Microsecond pulsed Dye–laser at 577 NM", *Lasers Surg. Med.*, 4:375–380 (1984).

Henning et al., "Port Wine Stain Coagulation Experiments with a 540–nm Continuous Wave Dye–laser", *Lasers Surg. Med.*, 2:205–210 (1983).

Henning et al., "Rhinophyma Treated by Argon Laser",*Lasers Surg. Med.*, 2:211–215 (1983).

Henning et al., "Treatment of Keloids and Hypertrofic Scars with an Argon Laser",*Lasers Surg. Med.*, 6:72–75 (1986).

Hilsenrath, J.E., "Investing it; Unsightly Veins? Zap. Wall St. Woes? Zap.", *New York Times*, http://www.nytimes.com, pp. 1–3 (Jun. 23, 1996).

Hruza et al., "Laser Skin Resurfacing", *Arch. Dermatol.*, 132:451–455 (1996).

Hughes, P.S.H., "Multiple Miliary Osteomas of the Face Ablated With the Erbium: YAG Laser",*Arch. Dermatol.*, 135:378–380 (1999).

"Infrared–Coagulator", Lumatec product leaflet, pp. 1–4.

Ishimaru, A., "Diffusion of light in turbid material",*Applied Optics*, 28(12):2210–2215 (1989).

Jacques, S.L., "The Role of Skin Optics in Diagnostic and Therapeutic Uses of Lasers", *Lasers Dermatol.*, pp. 1–21 (1992).

Jaitly et al., "1 MV Long Pulse Generator with Low Ripple and Low Droop",*$8^{th}$ IEEE Int'l Pulsed Power Conf.*, pp. 161–165 (1991).

Jaitly et al., "Design and Testing of Multi–output 300kV Prototype Induction Cell Pulsed Power Supply for Darht", *$10^{th}$ IEEE Int'l Pulsed Power Conf.*, pp. 1412–1421 (1995).

Jay, H.H., "Victory Over Veins", http://www.nytimes.com, pp. 1–2 (Jul. 21, 1996).

Johannigmann et al., "Ein Neus Ultraschall–Kontaktgel", *Geburtsh. U. Frauenheilk*, p. 34 (1974) (in German, with English Abstract Only).

Kalka et al., "Photodynamic Therapy in Dermatology",*J. Am. Acad. Dermatol.*, 42:389–413 (2000).

Kaminester, L.H., "Suntanning Centers", *JAMA*, 244(11):1258–1259 (1980).

Kaufmann et al., "Pulsed 2·94–µm erbium–YAG laser skin ablation–experimental results and first clinical application", *Clin. Exp. Dermatol.*, 15:389–393 (1990).

Keijzer et al., "Laser Beam Diameter for Port Wine Stain Treatment", *Lasers Surg. Med.*, 11:601–605 (1991).

Kennedy et al., "Photodynamic Therapy with Endogenous Protoporphyrin, IX: Basic Principles and Present Clinical Experience", *J. of Photochem. Photobio.*, 6:143–148 (1990).

Kilmer et al., "Pulse Dye Laser Treatment of Rhytids", *Lasers Surg. Med.*, p. 44 (Abstract No. 194) (1997).

Koechner, W., in *Solid State Laser Engineering*, Springer Series in Optical Sciences—vol. 1, Chapters 1–2, pp. 1–620, Springer–Verlag, New York (1976).

Lakmaker et al., "Modeling the Color Perception of Port Wine Stains and its Relation to the Depth of Laser Coagulated Blood vessels", *Lasers Surg. Med.*, 13:219–226 (1993).

Lash et al., "How We Got Here", *Lasers Surg. Med.*, 3:13 (Abstract No. 29) (1983).

Lask et al., "Laser Skin Resurfacing with the Sik Touch Flashscanner for Facial Rhytides", *Dermatol. Surg.*, 21:1021–1024 (1995).

Lask et al., "Nonablative laser treatment of facial rhytides", *SPIE*, 2970:338–349 (1997).

Levins et al., "Q–Switched Ruby Laser Treatment of Tattoos", *Lasers Surg. Med.*, Suppl. 3:63–64 (Abstract No. 255) (1991).

Lowe et al., "Skin Resurfacing with the Ultrapulse Carbon Dioxide Laser",*Dermatol. Surg.*, 21:1025–1029 (1995).

Magee et al., "Vein Marking Through Ultrasound Coupling Gel",*Eur. J. Vasc. Surg.*, 4:491–492 (1990).

Majaron et al., "Deep Coagulation of Dermal Collagen with Repetitive Er:YAG Laser Irradiation", *Lasers Surg. Med.*, 26:215–222 (2000).

Majaron et al., "Er:YAG Laser Skin Resurfacing Using Repetitive Long–Pulse Exposure and Cryogen Spray Cooling: I. Histological Study", *Lasers Surg. Med.*, 23:121–130 (2001).

Majaron et al., "Er:YAG Laser Skin Resurfacing Using Repetitive Long–Pulse Exposure and Cryogen Spray Cooling: II. Theoretical Analysis", *Lasers Surg. Med.*, 28:131–137 (2001).

Margolis et al., "Visible Action Spectrum for Melanin–Specific Selective Photothermolysis", *Lasers Surg. Med.*, 9:389–397 (1989).

Marhic et al., "White–Light Flashlamp–pumped dye laser for photography through endoscopes", *Optics Communications*, 45(1):21–25 (1983).

McCaughan et al., "Photodynamic Therapy for Cutaneous and Subcutaneous Malignant Neoplasms", *Arch. Surg.*, 124:211–216 (1989).

McCaughan et al., "Photodynamic Therapy: An Eight–Year Experience", in *Photodynamic Therapy: Basic Principles and Clinical Applications*, pp. 323–331 (1992).

Meijering et al., "Limits of Radial Time Constants to Approximate Thermal Response of Tissue", *Lasers Surg. Med.*, 13:685–687 (1993).

Miller et al., "Optical Modelling of Light Distributions in Skin Tissue Following Laser Irradiation", *Lasers Surg. Med.*, 13:565–571 (1993).

Milner et al., "Analysis of nonablative skin resurfacing", *SPIE*, 2970:367–373 (1997).

Mordon et al., "Rationale for Automatic Scanners in Laser Treatment of Port wine Stains", *Lasers Surg. Med.*, 13:131–123 (1993).

Morelli et al., "Tunable Dye Laser (577 nm) Treatment of Port Wine Stains", *Lasers Surg. Med.*, 6:94–99 (1986).

Motamedi et al., "Thermal Response of Tissue During Laser Angioplasty", *Lasers Surg. Med.*, 5:172 (Abstract No. 114) (1985).

Mutzhas et al., "A New Apparatus with High Radiation Energy Between 320–460 nm: Physical Description and Dermatological Applications", *J. Invest. Dermatol.*, 76:42–47 (1981).

Nakagawa et al., "Ultrastructural Changes in Human Skin After Exposure to a Pulsed Laser", *J. Invest. Dermatol.*, 84(5):396–400 (1985).

Nestor et al., "New Perspectives on Photorejuvenation", *Skin & Aging*, 11:68–74 (2003).

Newman et al., "Variable Pulse Erbium: YAG Laser Skin Resurfacing of Perioral Rhytides and Side–by–side Comparison with Carbon Dioxide Laser", *Lasers Surg. Med.*, 26:208–214 (2000).

Parrish et al., "Exploring Mechanisms of Specificity in Laser–Tissue Interactions", *Lasers Surg. Med.*, 3:175 (Abstract No. 260) (1983).

Parrish et al., "Spatial Confinement of Thermal Effects of Pulsed Laser Irradiation of Tissue", *Lasers Surg. Med.*, 3:157 (Abstract No. 195) (1973).

Paul et al., "The Effect of Temperature and Other Factors on Selective Microvascular Damage Caused by Pulsed Dye Laser", *J. Invest. Dermatol.*, 81(4):333–336 (1983).

Pfefer et al., "Mechanisms of Laser–Induced Thermal Coagulation of Whole Blood in vitro", *SPIE*, 3590:20–31 (1999).

Philipp et al., "Treatment of Congenital Vascular Disorders: Classification, Step Programme and Therapeutical Procedures", *SPIE*, 2086:228–238 (1993).

Pickering et al., "585 nm for the Laser Treatment of Port Wine Stains: A Possible Mechanism", *Lasers Surg. Med.*, 11:616–618 (1991).

Plewig et al., "A new apparatus for the delivery of high intensity UVA and UVA + UVB irradiation, and some dermatological applications", *Br. J. Dermatol.*, 98:15–24 (1978).

Polla et al., "Tunable Pulsed Dye Laser for the Treatment of Benign Cutaneous Vascular Ectasia", *Dermatologica*, 174:11–17 (1987).

Pottier et al., "Assessment of Non–Coherent Light Sources for Photodynamic Therapy", *SPIE*, 2371:364–368 (1995).

Pratesi, R., "Potential Use of Incoherent and Coherent Light–Emitting–Diodes (LEDs) in Photomedicine", in *Photomedicine, Laser Photobiol. Photomed.*, 22:293–308 (1983).

Ramrus et al., "A Compact One–Half MV Rep–Rate Pulser", $20^{th}$ *IEEE Power Modulator Symposium*, pp. 68–71 (1992).

Ramrus et al., "Design and Performance of a One–Half MV Rep–Rate Pulser", Proc. Of the $8^{th}$ IEEE International Pulsed Power Conference, pp. 982–985 (1991).

Ranganathan et al., "Promises for Ultrasonic Waves on Activity of Silica Gel and Some Supported Catalystes", *Ind. Eng. Chem. Prod. Res. Develop.*, 12:155–158 (1973).

Rassing et al., "Measurement of Ultrasonic Absorption in a Gel by Light Diffraction and Resonator Methods", *J. Mol. Liq.*, 26:97–108 (1983).

Rastegar et al., "Technique for Measurement of One–Dimensional Instantaneous Ablation Velocity", *Lasers Surg. Med.*, 8:533–535 (1988).

Raulin et al., "Treatment of a Nonresponding Port–Wine Stain With a New Pulsed Light Source (PhotoDerm® VL)", *Lasers Surg. Med.*, 21:203–208 (1997).

Raulin et al., "Treatment of Adult Port–Wine Stains Using Intense Pulsed Light Therapy (PhotoDerm VL): Brief Initial Clincial Report", *Dermatol. Surg.*, 23:594–601 (1997).

Raulin et al., "Treatment of benign venous malformations with an intense pulsed light source (PhotoDerm VL)", *Eur. J. Dermatol.*, 7:279–282 (1997).

Raulin et al., "Treatment of Essential Telangiectasias with an Intense Pulsed Light Source (PhotoDerm VL)", *Dermatol. Surg.*, 23:941–946 (1997).

Raulin et al., "Treatment of Port–wine Stains With a Noncoherent Pulsed Light Source", *Arch. Dermatol.*, 135:679–683 (1999).

Reyes et al., "Treatment of port–wine stains during childhood with the flashlamp–pumped pulsed dye laser", *J. Am. Acad. Dermatol.*, 23:1142–1148 (1990).

Ross et al., "Effects of $CO_2$ Laser Pulse Duration in Ablation and Residual Thermal Damage Implications for Skin Resurfacing", *Lasers Surg. Med.*, 19:123–129 (1996).

Rowe, P.M., "Photodynammic therapy begins to shine", *Lancet*, 351:1496 (1998).

Sadick et al., "Photorejuvation with Intense Pulsed Light: Results of a Multi–Center Study", *J. Drugs Dermatol.*, 3(1):41–49 (2004).

Sadick, N.S., "A Structural Approach to Nonablative Rejuvenation", *Cosmetic Dermatol.*, 15(12):39–43 (2002).

Sadick, N.S., "Update on Non–Ablative Light Therapy for Rejuvenation: A Review", *Lasers Surg. Med.*, 32:120–128 (2003).

Schamiloglu et al., "Modern Pulsed Power: Charlie Martin and Beyond", *Proceedings of the IEEE*, 92(7):1014–1020 (2004).

Schroeter et al., "An Intense Light Source: The Photoderm VL–Flashlamp as a New Treatment Possibility for Vascular Skin Lesions", *Dermatol. Surg.*, 24:743–748 (1998).

Schroeter et al., "Clinical significance of an intense, pulsed light source on leg telangiectasias of up to 1mm diameter", *Eur. J. Dermatol.*, 7:38–42 (1997).

Schroeter et al., "Photoderm VL treatment of leg teleangiectasia", *JEADV*, 5(Suppl. 1):S49 (Abstract No. W76) (1995).

Schwimmer et al., "The Effect of Ultrasound Coupling Gels on Sperm Motility In Vitro", *Fertil. Steril.*, 42:946–947 (1984).

Sheean et al., "Arrest of Embryo Development by Ultrasound Coupling Gels", *Fertil. Steril.*, 45:568–571 (1986).

Smith et al., "532–Nanometer Green Laser Beam Treatment of Superficial Varicosities of the Lower Extremities", *Lasers Surg. Med.*, 8:130–134 (1988).

Steiger et al., "Comparison of Different Pulsed and Q–switched Solid–state Laser Systems for Endoscopic Laser Induced Shock Wave Lithotripsy: Performance and Laser/Stone Interactions", *SPIE*, 2300:94–101 (1990).

Strickland et al., "A 5kV, 250 kA Rep–Rated Pulser Using Parallel Ignitrons", $7^{th}$ *IEEE Int'l Pulsed Conf.*, pp. 729–731 (1989).

Sunde et al., "Traumatic Tattoo Removal: Comparison of Four Treatment Methods in an Animal Model with Correlation to Clinical Experience", *Lasers Surg. Med.*, 10:158–164 (1990).

Svaasand et al., "Light and Drug Distribution with Topically Administered Photosensitizers", *Lasers Surg. Med.*, 11:261–265 (1996).

Szeimies et al., "A Possible New Incoherent Lamp for Photodynamic Treatment of Superficial Skin Lesions", *Acta Derm. Venereol (Stockh).*, 74:117–119 (1994).

Tan et al., "Action Spectrum of Vascular Specific Injury Using Pulsed Irradiation", *J. Invest. Dermatol.*, 92(6):868–871 (1989).

Tan et al., "EMLA for Laser Treatment of Portwine Stains in Children", *Lasers Surg. Med.*, 12:543–548 (1992).

Tan et al., "Histologic Responses of Port–wine Stains Treated by Argon, Carbon Dioxide, and Tunable Dye Lasers", *Arch. Dermatol.*, 122:1016–1022 (1986).

Tan et al., "Pulsed Dye Laser Treatment of Recalcitrant Verrucae: A Preliminary Report", *Lasers Surg. Med.*, 13:127–137 (1993).

Tan et al., "Treatment of Children with Port–Wine Stains Using the Flashlamp–Pulsed Tunable Dye Laser", *N. Engl. J. Med.*, 320(7):416–421 (1989).

Taub, A.F., "Photodynamic Therapy: Other Uses", *Dermtol. Clin.*, 25:101–109 (2007).

Taylor et al., "Q–Switched Ruby Laser (QSRL) Irradiation of Benign Pigmented Lesions: Dermal vs. Epidermal", *Lasers Surg. Med.*, 3:65 (Abstract No. 262) (1991).

Templeton et al., "Comparison of infrared coagulation and rubber band ligation for first and second degree haemorrhoids: a randomized prospective clinical trial", *Br. Med. J.*, 286:1387–1389 (1983).

Troccoli et al., "Multiple–Pulse Photocoagulation of Blood Vessels With A 585 Nm Tunable Laser", *Lasers Surg. Med.*, 4:3 (Abstract No. 2) (1992).

van Gemert et al., "Can Physical Modeling Lead to an Optimal Laser Treatment Strategy for Port–Wine Stains", in *Laser Applications in Medicine and Biology*, Chapter 5, pp. 199–247, Plenum Press, New York (1991).

van Germert et al., "Instantaneous Ablation Behavior of In–Vitro Rods During Laser Irradiation", *Lasers Surg. Med.*, 5:136 (Abstract No. 4) (1985).

van Germert et al., "Is There an Optimal Laser Treatment for Port Wine Stains?", *Lasers Surg. Med.*, 6:76–83 (1986).

van Germert et al., "Wavelengths for Laser Treatment of Port Wine Stains and Telangiectasia", *Lasers Surg. Med.*, 16:147–155 (1995).

"Varicose Vein Device Producer comes to U.S. Market", *Clinica*, 687:9 (Jan. 8, 1996).

Venning et al., "Tattoo removal using infra–red coagulation: a dose comparison", *Br. J. Dermatol.*, 117:99–105 (1987).

Wagner et al., "Percutalgine–Gel et Ultrasonotherapie en Pathologie du Sport", *La Revue de Medecine*, 32:1681–1683 (1982) (in French, with English Abstract Only).

Waldorf et al., "Skin Resurfacing of Fine to Deep Rhytides Using a Char–free Carbon Dioxide Laser in 47 Patients", *Dermatol. Surg.*, 21:940–946 (1995).

Walsh et al., "Er:YAG Laser Ablation of Tissue: Measurement of Ablation Rates", *Lasers Surg. Med.*, 9:327–337 (1989).

Walsh et al., "Pulsed $CO_2$ Laser Tissue Ablation: Effect of Tissue Type and Pulse Duration On Thermal Damage", *Lasers Surg. Med.*, 8:108–118 (1988).

Walsh, J.T., "Er:YAG Laser Ablation of Tissue: Effect of Pulse Duration and Tissue Type on Thermal Damage", *Lasers Surg. Med.*, 9:314–326 (1989).

Walsh, J.T., "Pulsed Laser Ablation of Tissue: Analysis of the Removal Process and Tissue Healing", *Unpublished Ph.D. dissertation Massachusetts Institute of Technology*, on file with Institute Archives and Hayden Library, Massachusetts Institute of Technology, pp. 1–312 (1988).

Weiss et al., "Rejuvenation of Photoaged Skin: 5 Years Results with Intense Pulsed Light of the Face, Neck and Chest", *Dermatol. Surg.*, 28:1115–1119 (2002).

Welch et al., "Practical Models for Light Distribution in Laser–Irradiated Tissue", *Lasers Surg. Med.*, 6:488–493 (1987).

Werner et al., "Die Hamangiombehandlung mit dem Neodym: Yttrium–Aluminum–Granat Laser (Nd:YAG–Laser)", *Laryngo–Rhino–Otol.*, 71:388–395 (1992), (in German, with English Abstract Only).

West, T., "How Laser Surgery Can Help Your Rosacea Patients", *Skin & Aging*, pp. 43–46 (1998).

Wilder, D., "Pulsed 1064–nm Nd:YAG Laser Therapy for Noninvasive Treatment of a Massive Hemangioma: Case Report", *J. Clin. Laser Med. Surg.*, 17(6):245–247 (1999).

Wilson et al., "The physics of photodynamic therapy", *Phys. Med. Biol.*, 31(4):327–360 (1986).

Groot et al., Comparison of the Infrared Coagulator and the Carbon Dioxide Laser in the Removal of Decorative Tattoos, Dermatologic Surgery, vol. 13, No. 3 (Sep. 1986).

Brochure for an Infrared Coagulator by Redfield Corporation (1988).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 7 is confirmed.

Claims 1–6 and 8–10 are cancelled.

New claims 11–41 are added and determined to be patentable.

*11. The therapeutic treatment device of claim 7 wherein the light guide is configured such that light from the incoherent light source is directed at about a 6.4 square centimeter area of skin.*

*12. A therapeutic treatment device for coagulating blood in blood vessels underlying an epidermal layer, the device comprising:*
  *a hand-held unit configured to be disposed in contact with a skin treatment area, including a flashlamp, at least one filter, and a light guide operable to provide a pulsed light output at least 3 square centimeters in size; and*
  *a control box operably connected to the hand-held unit, including a power supply, at least one microprocessor, and a driver circuit, the control box being configured to switch the flashlamp between an on and off state and to control a pulse width and a delay between pulses;*
  *wherein the pulsed light output has a wavelength of about 500-1000 nm, a pulse width of about 5 to 50 msec, and an energy density of about 6 to 30 Joules per square centimeter.*

*13. The therapeutic treatment device of claim 12 wherein the control box includes a snubber circuit operably connected to the driver circuit.*

*14. The therapeutic treatment device of claim 12 wherein the entrance of the light guide is rectangular in shape.*

*15. The therapeutic treatment device of claim 14 wherein the length of the flashlamp is at least as long as the length of the entrance of the light guide.*

*16. The therapeutic treatment device of claim 12 wherein the at least one filter is disposed in proximity to one end of the light guide.*

*17. The therapeutic treatment device of claim 12 wherein the at least one filter can be moved into and out of the light output.*

*18. The therapeutic treatment device of claim 12 wherein the driver circuit includes an IGBT.*

*19. The therapeutic treatment device of claim 12 wherein the driver circuit includes an GTO.*

*20. The therapeutic treatment device of claim 12 wherein the pulsed light output has a wavelength of about 550-1000 nm.*

*21. The therapeutic treatment device of claim 12 wherein the pulsed light output has a wavelength of about 520-650 nm.*

*22. The therapeutic treatment device of claim 12 wherein the pulsed light output has a wavelength of about 520-700 nm.*

*23. The therapeutic treatment device of claim 12 wherein the pulsed light output has a wavelength of about 600-1000 nm.*

*24. The therapeutic treatment device of claim 12 wherein the control box includes at least two capacitors connected in parallel.*

*25. The therapeutic treatment device of claim 12 wherein the control box includes at least two capacitors connected in series.*

*26. The therapeutic treatment device of claim 12 wherein the delay between pulses is at least 5 msec.*

*27. The therapeutic treatment device of claim 12 further comprising a gel disposed between the skin and the hand-held unit.*

*28. A therapeutic medical device for applying light to skin to coagulate blood in blood vessels underlying an epidermal layer, the device comprising:*
  *a housing means for disposing a flashlamp proximate to the skin;*
  *a filtering means for limiting the wavelength of light which impinges the skin to values within a range of 520-1000 nm;*
  *a light guide means for contacting the skin and directing light to at least a 4 square centimeter area of skin;*
  *a control means for controlling the flashlamp to provide at least one pulse of light characterized by a pulse width within the range of 10-50 msec, and an energy density on the skin within the range of 6-20 Joules per square centimeter, wherein the control means includes a driver circuit and is configured to switch the flashlamp between an on and off state and to control a pulse width and a delay between pulses; and*
  *a connection means for flexibly coupling the housing means to the control means.*

*29. The device of claim 28 comprising a gel means for contacting the skin, wherein the light guide means contacts the gel means.*

*30. The device of claim 28 wherein the control means is configured to provide a train of pulses.*

*31. The device of claim 30 wherein the delay between each pulse in the train of pulses is at least 5 msec.*

*32. The device of claim 28 comprising a database means for storing treatment parameters.*

*33. A method of applying light to skin to coagulate blood in blood vessels underlying an epidermal layer, the method comprising:*
  *selecting at least one treatment parameter on a user interface, wherein the treatment parameters include a pulse width and a fluence;*
  *positioning a hand-held unit on an area of the skin, wherein the hand-held unit includes a flashlamp, a filter, and a light guide which is placed in contact with at least a 4 square centimeter area of the skin;*
  *controlling the flashlamp, including controlling the pulse width and a delay between pulses, using a switch based on the at least one treatment parameter, wherein the controlling includes switching the flashlamp between an on and off state; and*
  *triggering the flashlamp to transmit a pulse of light corresponding to the at least one treatment parameter, wherein the pulse of light is capable of coagulating blood in the blood vessels underlying the epidermal layer.*

34. The method of claim 33 comprising applying gel to the skin, wherein the light guide makes contact with the gel.

35. The method of claim 33 comprising converting at least a portion of ultraviolet light emitted from the flashlamp to visible light with a fluorescent material.

36. The method of claim 33 wherein triggering the flashlamp includes transmitting a train of pulses corresponding to the at least one treatment parameters.

37. A system for applying light to skin to coagulate blood in blood vessels underlying an epidermal layer, the system comprising:
- a control system including:
  - a user interface configured to receive a fluence parameter and a pulse width parameter;
  - a microprocessor programmed to calculate a trigger signal based on the fluence parameter and the pulse width parameter;
  - a driver circuit including an IGBT switch operably coupled to the microprocessor and configured to generate at least one electrical pulse based on the trigger signal;
  - a plurality of capacitors operably connected to the IGBT switch;
  - a charging power supply operably connected to the plurality of capacitors;
- a hand-held unit, including:
  - a light guide having a cross section of at least 4 square centimeters configured to contact the skin;
  - a flashlamp operably connected to the driver circuit and configured to emit light to coagulate blood based on the electrical pulse;
  - at least one filter disposed between the light guide and the flashlamp and configured to transmit light having wavelengths between about 520-1000 nm, wherein the control system is configured to switch the flashlamp such that at least a first interval of light is transmitted to the blood vessels underlying the epidermal layer.

38. A therapeutic treatment device for coagulating blood in blood vessels underlying an epidermal layer comprising:
- a hand-held unit configured to be disposed in contact with a skin treatment area including an incoherent light source operable to provide a pulsed light output for coagulation of blood, wherein the incoherent light source is a flashlamp;
- a driver circuit including a switch capable of being electrically turned on and being electrically turned off to thereby provide intervals of light, wherein the driver circuit is connected to the light source to control the pulse width and delay between intervals of light, wherein the driver circuit is configured to cause the flashlamp to generate intervals of light having a duration of about 5-50 msec. and an energy density of about 6-20 Joules per square centimeter; and
- a filter configured transmit light having wavelengths of about 500-1000 nm; and
- a light guide configured to transmit light from the flashlamp to an area of skin that is at least 3 square centimeters in size.

39. The device of claim 38 wherein the driver circuit includes at least one of a IGBT and a GTO.

40. The device of claim 38 wherein the driver circuit is configured to delay subsequent interval of light by at least 5 msec.

41. The device of claim 38 further comprising a gel disposed between the skin treatment area and the hand-held unit.

* * * * *

(12) EX PARTE REEXAMINATION CERTIFICATE (7505th)
United States Patent
Eckhouse

(10) Number: US 5,626,631 C2
(45) Certificate Issued: May 11, 2010

(54) METHOD AND APPARATUS FOR THERAPEUTIC ELECTROMAGNETIC TREATMENT

(75) Inventor: Shimon Eckhouse, Haifa (IL)

(73) Assignee: Lumenis, Ltd., Yokneam (IL)

Reexamination Request:
No. 90/010,386, Jan. 15, 2009
No. 90/010,493, Apr. 10, 2009

Reexamination Certificate for:
Patent No.: 5,626,631
Issued: May 6, 1997
Appl. No.: 08/383,509
Filed: Feb. 3, 1995

Reexamination Certificate C1 5,626,631 issued Mar. 3, 2009

Related U.S. Application Data

(63) Continuation-in-part of application No. 07/964,210, filed on Oct. 20, 1992, now Pat. No. 5,405,368.

(51) Int. Cl.
*A61N 5/06* (2006.01)

(52) U.S. Cl. .................................. 607/88; 606/9
(58) Field of Classification Search .................. None
See application file for complete search history.

(56) References Cited

U.S. PATENT DOCUMENTS

| | | | |
|---|---|---|---|
| 1,106,699 A | 8/1914 | Carroll | 600/200 |
| 1,651,385 A | 12/1927 | Goodrich | 392/409 |
| 2,699,771 A | 1/1955 | Ruttger-Pelli | 601/15 |
| 2,716,698 A | 8/1955 | Brukner | 240/1 |
| 2,888,927 A | 6/1959 | Fozard | 606/43 |
| 2,954,771 A | 10/1960 | Boyan | 128/396 |
| 3,126,295 A | 3/1964 | Young | 428/337 |
| 3,289,669 A | 12/1966 | Dwyer et al. | 600/565 |
| 3,307,553 A | 3/1967 | Liebner | 607/1 |
| 3,327,712 A | 6/1967 | Kaufman et al. | 606/40 |
| 3,538,919 A | 11/1970 | Meyer | 606/36 |
| 3,559,531 A | 2/1971 | Leibfritz et al. | 91/26 |
| 3,599,934 A | 8/1971 | Reed | 251/363 |
| 3,601,616 A | 8/1971 | Katsumata | 250/223 |
| 3,658,068 A | 4/1972 | McNall | 128/395 |

(Continued)

FOREIGN PATENT DOCUMENTS

| | | |
|---|---|---|
| AT | 355200 | 3/2006 |
| AU | 1851583 | 3/1984 |
| AU | 2940397 | 12/1997 |
| AU | 0691713 | 5/1998 |
| BE | 894290 | 3/1983 |
| CA | 1122156 | 4/1982 |
| CA | 1197563 | 12/1985 |
| CA | 1260116 | 9/1989 |
| CA | 2093055 | 10/1993 |
| CA | 2131750 | 1/1996 |

(Continued)

OTHER PUBLICATIONS

"Sharplan 771 Microscan Data Sheet", Mar. 28, 1985.
Alster et al., "Improvement of facial acne scars by the 585 nm flashlamp-pumped pulsed dye laser", *Journal of the American Academy of Dermatology*, 35(1):79–81 (Jul. 1996).

(Continued)

*Primary Examiner*—Beverly M. Flanagan

(57) ABSTRACT

A therapeutic treatment device for coagulating blood in blood vessels underlying an epidermal layer is disclosed having an incoherent light source operable to provide a pulsed light output for treatment and a driver circuit, including a switch capable of being electrically turned on and being electrically turned off to thereby provide a first interval of light, connected to the light source to control the pulse width and delay between pulses.

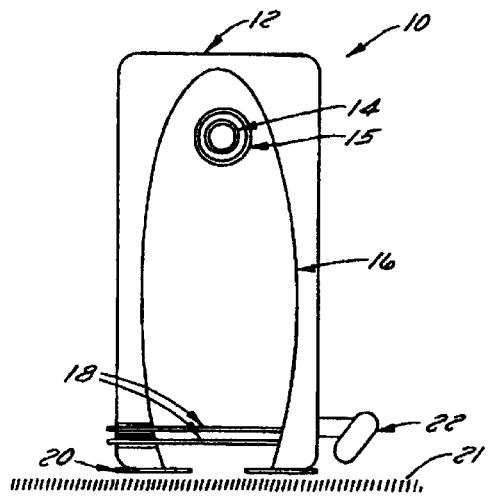

U.S. PATENT DOCUMENTS

| | | |
|---|---|---|
| 3,680,000 A | 7/1972 | Chesler et al. .................. 372/99 |
| 3,693,623 A | 9/1972 | Harte et al. ...................... 606/9 |
| 3,710,798 A | 1/1973 | Bredemeier .................. 606/11 |
| 3,804,732 A | 4/1974 | Goodkin ...................... 204/58 |
| 3,806,829 A | 4/1974 | Duston et al. ............. 372/38.01 |
| 3,818,914 A | 6/1974 | Bender ........................ 607/90 |
| 3,821,510 A | 6/1974 | Muncheryan ................ 219/121 |
| 3,834,391 A | 9/1974 | Block ............................ 606/9 |
| 3,884,236 A | 5/1975 | Krasnov ........................ 606/3 |
| 3,916,143 A | 10/1975 | Farrell .................... 219/121.69 |
| 3,930,504 A | 1/1976 | de Laforcade ............ 128/303.1 |
| 3,967,627 A | 7/1976 | Brown ........................ 128/400 |
| 3,999,552 A | 12/1976 | Huggins ................ 128/303.13 |
| 4,022,534 A | 5/1977 | Kishner ...................... 356/446 |
| 4,058,752 A | 11/1977 | Woods et al. ............... 315/360 |
| 4,112,335 A | 9/1978 | Gonser ................... 315/241 R |
| 4,122,853 A | 10/1978 | Smith ............................ 606/4 |
| 4,174,714 A | 11/1979 | Mehl .................... 128/303.13 |
| 4,213,462 A | 7/1980 | Sato ........................... 128/634 |
| 4,229,658 A | 10/1980 | Gonser ................... 250/504 H |
| 4,232,678 A | 11/1980 | Skovajsa .................... 128/395 |
| 4,233,493 A | 11/1980 | Nath ......................... 219/354 |
| 4,241,382 A | 12/1980 | Daniel ........................ 362/581 |
| 4,246,902 A | 1/1981 | Martinez ..................... 604/22 |
| 4,266,548 A | 5/1981 | Davi ........................... 606/14 |
| 4,283,661 A | 8/1981 | Doty ........................... 315/360 |
| 4,298,005 A | 11/1981 | Mutzhas .................... 128/396 |
| 4,316,467 A | 2/1982 | Muckerheide ................ 606/9 |
| 4,321,930 A | 3/1982 | Jobsis et al. ................ 128/633 |
| 4,336,809 A | 6/1982 | Clark ......................... 128/665 |
| 4,366,570 A | 12/1982 | Bees ........................... 372/70 |
| 4,380,240 A | 4/1983 | Jobsis et al. ................ 128/633 |
| 4,381,007 A | 4/1983 | Doss .................... 128/303.1 |
| 4,387,952 A | 6/1983 | Slusher ................... 359/220.1 |
| 4,388,924 A | 6/1983 | Weissman et al. ........ 128/303.1 |
| 4,408,602 A | 10/1983 | Nakajima ................... 606/10 |
| 4,436,097 A | 3/1984 | Cunningham ............... 600/520 |
| 4,441,485 A | 4/1984 | Reynolds ................... 600/200 |
| 4,444,190 A | 4/1984 | Mutzhas .................... 128/396 |
| 4,454,882 A | 6/1984 | Takano ........................ 607/89 |
| 4,469,098 A | 9/1984 | Davi ............................ 606/7 |
| 4,497,018 A | 1/1985 | Rice ........................... 363/96 |
| 4,503,854 A | 3/1985 | Jako ........................... 603/11 |
| 4,506,196 A | 3/1985 | Bees ..................... 315/241 R |
| 4,515,165 A | 5/1985 | Carroll ...................... 600/475 |
| 4,516,195 A | 5/1985 | Gonser ...................... 362/281 |
| 4,520,816 A | 6/1985 | Schachar et al. .............. 606/4 |
| 4,521,194 A | 6/1985 | Myers et al. ................ 433/215 |
| 4,539,987 A | 9/1985 | Nath et al. ............... 128/303.1 |
| 4,554,666 A | 11/1985 | Altman ........................ 372/19 |
| 4,555,179 A | 11/1985 | Langerholc et al. ......... 356/342 |
| 4,559,942 A | 12/1985 | Eisenberg .................. 128/303 |
| 4,560,883 A | 12/1985 | Kerschgens ................ 250/504 |
| 4,564,011 A | 1/1986 | Goldman ................ 128/303.1 |
| 4,566,453 A | 1/1986 | Kumano et al. ................ 606/8 |
| 4,587,396 A | 5/1986 | Rubin ................... 219/121.78 |
| 4,601,037 A | 7/1986 | McDonald ................... 372/25 |
| 4,608,978 A | 9/1986 | Rohr ............................ 606/9 |
| 4,608,979 A | 9/1986 | Breidenthal et al. ...... 128/303.1 |
| 4,611,245 A | 9/1986 | Trias et al. ................. 358/235 |
| 4,617,926 A | 10/1986 | Sutton .......................... 606/9 |
| 4,619,887 A | 10/1986 | Hooper et al. .............. 430/313 |
| 4,620,547 A | 11/1986 | Boebel ....................... 600/567 |
| 4,645,980 A | 2/1987 | Yang ........................... 315/159 |
| 4,647,830 A | 3/1987 | Bees ............................ 320/1 |
| 4,653,495 A | 3/1987 | Nanaumi ................ 128/303.1 |
| 4,657,018 A | 4/1987 | Hakky ........................ 606/46 |
| 4,669,466 A | 6/1987 | L'Esperance .................. 606/3 |
| 4,672,969 A | 6/1987 | Dew .......................... 128/397 |
| 4,686,986 A | 8/1987 | Fenyo et al. .................. 607/90 |
| 4,712,537 A | 12/1987 | Pender ....................... 600/200 |
| 4,718,418 A | 1/1988 | L'Esperance, Jr. ............. 606/5 |
| 4,726,377 A | 2/1988 | Jegers et al. ................ 128/376 |
| 4,729,375 A | 3/1988 | Jegers et al. ................ 128/376 |
| 4,733,660 A | 3/1988 | Itzkan .................... 128/303.1 |
| 4,744,360 A | 5/1988 | Bath ............................ 606/6 |
| 4,750,486 A | 6/1988 | Butler et al. .................. 606/18 |
| 4,754,381 A | 6/1988 | Downs ....................... 362/297 |
| 4,757,431 A | 7/1988 | Cross et al. ................. 362/261 |
| 4,768,513 A | 9/1988 | Suzuki ....................... 600/476 |
| 4,773,097 A | 9/1988 | Suzaki et al. ............... 382/128 |
| 4,775,361 A | 10/1988 | Jacques et al. ................ 604/20 |
| 4,784,135 A | 11/1988 | Blum et al. ................... 606/3 |
| 4,792,341 A | 12/1988 | Kozikowski et al. ........... 8/103 |
| 4,803,694 A | 2/1989 | Lee et al. ...................... 372/98 |
| 4,810,658 A | 3/1989 | Shanks et al. .............. 436/172 |
| 4,818,230 A | 4/1989 | Myers et al. ................ 433/215 |
| 4,818,847 A | 4/1989 | Hara et al. .................. 235/455 |
| 4,829,262 A | 5/1989 | Furumoto .................... 330/4.3 |
| 4,835,749 A | 5/1989 | Welton ........................ 368/10 |
| 4,839,562 A | 6/1989 | Francis et al. ............... 315/149 |
| 4,840,798 A | 6/1989 | Skaliotis .................... 424/488 |
| 4,846,172 A | 7/1989 | Berlin ........................... 606/4 |
| 4,846,192 A | 7/1989 | MacDonald ............... 600/565 |
| 4,851,738 A | 7/1989 | Yang ........................... 315/159 |
| 4,858,090 A | 8/1989 | Downs ....................... 362/297 |
| 4,860,172 A | 8/1989 | Schlager et al. ............. 362/553 |
| 4,862,886 A | 9/1989 | Clarke et al. .................. 606/7 |
| 4,871,559 A | 10/1989 | Dunn et al. ................. 426/248 |
| 4,874,009 A | 10/1989 | Pickerrell et al. ......... 137/454.6 |
| 4,874,361 A | 10/1989 | Obagi ........................... 606/3 |
| 4,875,214 A | 10/1989 | Denne ........................... 372/5 |
| 4,883,333 A | 11/1989 | Yanez ......................... 385/33 |
| 4,884,568 A | 12/1989 | Hahn ...................... 128/303.1 |
| 4,894,547 A | 1/1990 | Leffell et al. .............. 250/461.2 |
| 4,897,771 A | 1/1990 | Parker ........................ 362/298 |
| 4,907,235 A | 3/1990 | Kuizenga ..................... 372/21 |
| 4,909,782 A | 3/1990 | Semm et al. ............... 606/171 |
| 4,910,942 A | 3/1990 | Dunn ........................... 53/425 |
| 4,913,132 A | 4/1990 | Gabriel ....................... 600/200 |
| 4,917,083 A | 4/1990 | Harrington et al. ............. 606/15 |
| 4,917,084 A | 4/1990 | Sinofsky ........................ 606/7 |
| 4,917,486 A | 4/1990 | Raven et al. ................. 351/221 |
| 4,926,861 A | 5/1990 | Fenyo et al. .................. 607/88 |
| 4,930,504 A | 6/1990 | Diamantopoulos et al. .. 128/395 |
| 4,938,221 A | 7/1990 | Tuffel ......................... 128/401 |
| 4,940,922 A | 7/1990 | Schuda et al. ............... 315/246 |
| 4,941,082 A | 7/1990 | Pailthorp et al. .............. 700/57 |
| 4,945,914 A | 8/1990 | Allen .......................... 600/426 |
| 4,947,305 A | 8/1990 | Gunter, Jr. .................. 362/297 |
| 4,947,859 A | 8/1990 | Brewer et al. .............. 128/715 |
| 4,950,880 A | 8/1990 | Hayner ..................... 250/201.9 |
| 4,955,882 A | 9/1990 | Hakky ........................ 606/14 |
| 4,973,848 A | 11/1990 | Kolobanov et al. ........ 250/458.1 |
| 4,974,138 A | 11/1990 | Negishi ....................... 362/347 |
| 4,976,709 A | 12/1990 | Sand ............................ 606/5 |
| 4,988,163 A | 1/1991 | Cohen et al. .................. 385/31 |
| 4,996,046 A | 2/1991 | Warshaw et al. ............ 424/445 |
| 5,000,752 A | 3/1991 | Hoskin et al. .................. 606/9 |
| 5,005,180 A | 4/1991 | Edelman et al. .............. 372/57 |
| 5,008,579 A | 4/1991 | Conley et al. ............... 310/303 |
| 5,011,793 A | 4/1991 | Obinata ..................... 427/383.1 |
| 5,016,151 A | 5/1991 | Mula ......................... 362/267 |
| 5,020,995 A | 6/1991 | Levy ........................... 433/215 |
| 5,023,886 A | 6/1991 | Hobart et al. ................. 372/99 |
| 5,025,446 A | 6/1991 | Kuizenga ..................... 372/21 |
| 5,034,235 A | 7/1991 | Dunn et al. ................. 426/238 |
| 5,039,867 A | 8/1991 | Nishihara et al. ......... 250/492.3 |
| 5,048,034 A | 9/1991 | Tulip ........................... 372/41 |
| 5,049,147 A | 9/1991 | Danon ........................ 606/10 |
| 5,054,488 A | 10/1991 | Muz ......................... 128/633 |

| Patent No. | Date | Inventor | Class |
|---|---|---|---|
| 5,057,100 A | 10/1991 | Lombardo | 606/17 |
| 5,057,104 A | 10/1991 | Chess | 606/9 |
| 5,059,192 A | 10/1991 | Zaias | 606/9 |
| 5,063,961 A | 11/1991 | Brunner | 137/454.5 |
| 5,066,291 A | 11/1991 | Stewart | 606/3 |
| 5,066,293 A | 11/1991 | Furumoto | 606/9 |
| 5,071,417 A | 12/1991 | Sinofsky | 606/8 |
| 5,071,422 A | 12/1991 | Watson et al. | 606/128 |
| 5,074,861 A | 12/1991 | Schneider et al. | 606/17 |
| 5,077,099 A | 12/1991 | Kukanskis et al. | 427/437 |
| 5,078,711 A | 1/1992 | Kakami et al. | 606/16 |
| 5,083,093 A | 1/1992 | Adler et al. | 328/65 |
| 5,084,881 A | 1/1992 | Farries et al. | 372/6 |
| 5,089,945 A | 2/1992 | Mula | 362/261 |
| 5,097,471 A | 3/1992 | Negus et al. | 372/18 |
| 5,106,364 A | 4/1992 | Hayafuji et al. | 604/22 |
| 5,109,463 A | 4/1992 | Lee | 385/123 |
| 5,112,328 A | 5/1992 | Taboada et al. | 606/4 |
| 5,113,462 A | 5/1992 | Clancy et al. | 385/53 |
| 5,123,026 A | 6/1992 | Fan et al. | 372/75 |
| 5,125,922 A | 6/1992 | Dwyer et al. | 606/3 |
| 5,126,621 A | 6/1992 | Morton et al. | 313/237 |
| 5,130,997 A | 7/1992 | Ortiz et al. | 372/21 |
| 5,133,035 A | 7/1992 | Hicks | 385/117 |
| 5,137,539 A | 8/1992 | Bowling | 44/626 |
| 5,139,494 A | 8/1992 | Freiberg | 606/3 |
| 5,146,923 A | 9/1992 | Dhawan | 600/476 |
| 5,161,526 A | 11/1992 | Hellwing et al. | 607/89 |
| 5,178,617 A | 1/1993 | Kuizenga et al. | 606/17 |
| 5,194,723 A | 3/1993 | Cates et al. | 250/205 |
| 5,200,604 A | 4/1993 | Rudko et al. | 250/205 |
| 5,201,731 A | 4/1993 | Hakky | 606/15 |
| 5,204,517 A | 4/1993 | Cates et al. | 250/205 |
| 5,206,867 A | 4/1993 | Esterowitz et al. | 372/20 |
| 5,207,670 A | 5/1993 | Sinofsky | 606/8 |
| 5,207,671 A | 5/1993 | Franken et al. | 606/9 |
| 5,217,455 A | 6/1993 | Tan | 606/9 |
| 5,222,952 A | 6/1993 | Loertscher | 606/6 |
| 5,226,107 A | 7/1993 | Stern et al. | 392/416 |
| 5,226,430 A | 7/1993 | Spears et al. | 128/898 |
| 5,226,907 A | 7/1993 | Tankovich | 606/133 |
| 5,242,460 A | 9/1993 | Klein et al. | 606/159 |
| 5,243,615 A | 9/1993 | Ortiz et al. | 372/34 |
| 5,246,435 A | 9/1993 | Bille et al. | 606/6 |
| 5,246,436 A | 9/1993 | Rowe | 606/13 |
| 5,247,935 A | 9/1993 | Cline et al. | 128/653.2 |
| 5,249,190 A | 9/1993 | Kortz et al. | 372/22 |
| 5,257,274 A | 10/1993 | Barrett et al. | 372/20 |
| 5,259,380 A | 11/1993 | Mendes et al. | 607/115 |
| 5,263,038 A | 11/1993 | Lukas et al. | 372/22 |
| 5,263,950 A | 11/1993 | L'Esperance, Jr. | 606/6 |
| 5,265,598 A | 11/1993 | Searfoss et al. | 607/88 |
| 5,269,778 A | 12/1993 | Rink et al. | 606/12 |
| 5,272,518 A | 12/1993 | Vincent | 356/405 |
| 5,272,713 A | 12/1993 | Sobey et al. | 372/69 |
| 5,274,728 A | 12/1993 | Tran | 385/142 |
| 5,280,378 A | 1/1994 | Lombardo | 359/199.1 |
| 5,281,798 A | 1/1994 | Hamm et al. | 250/205 |
| 5,282,797 A | 2/1994 | Chess | 606/9 |
| 5,282,798 A | 2/1994 | Bruse et al. | 606/17 |
| 5,287,380 A | 2/1994 | Hsia | 372/69 |
| 5,289,479 A | 2/1994 | Oka et al. | 372/22 |
| 5,290,273 A | 3/1994 | Tan | 606/9 |
| 5,290,274 A | 3/1994 | Levy et al. | 606/13 |
| 5,293,872 A | 3/1994 | Alfano | 128/664 |
| 5,300,097 A | 4/1994 | Lerner et al. | 607/93 |
| 5,304,167 A | 4/1994 | Freiberg | 606/3 |
| 5,304,169 A | 4/1994 | Sand | 606/5 |
| 5,304,170 A | 4/1994 | Green | 606/9 |
| 5,312,395 A | 5/1994 | Tan et al. | 606/9 |
| 5,312,396 A | 5/1994 | Feld et al. | 606/11 |
| 5,312,399 A | 5/1994 | Hakky et al. | 606/15 |
| 5,320,618 A | 6/1994 | Gustafsson | 606/9 |
| 5,321,715 A | 6/1994 | Trost | 372/69 |
| 5,325,458 A | 6/1994 | Morrow et al. | 385/125 |
| 5,328,488 A | 7/1994 | Daikuzono | 606/16 |
| 5,328,517 A | 7/1994 | Cates et al. | 134/7 |
| 5,330,517 A | 7/1994 | Mordon et al. | 607/89 |
| 5,334,190 A | 8/1994 | Seiler | 606/5 |
| 5,336,216 A | 8/1994 | Dewey | 606/4 |
| 5,336,217 A | 8/1994 | Buys et al. | 606/9 |
| 5,337,741 A | 8/1994 | Diamond | 600/8 |
| 5,342,198 A | 8/1994 | Vassiliadis et al. | 433/215 |
| 5,344,418 A | 9/1994 | Ghaffari | 606/9 |
| 5,344,433 A | 9/1994 | Talmore | 607/88 |
| 5,344,434 A | 9/1994 | Talmore | 607/88 |
| 5,345,457 A | 9/1994 | Zenzie et al. | 372/22 |
| 5,349,590 A | 9/1994 | Amirkhanian et al. | 372/6 |
| 5,360,424 A | 11/1994 | Klopotek | 606/4 |
| 5,363,387 A | 11/1994 | Sinofsky | 372/15 |
| 5,363,854 A | 11/1994 | Martens et al. | 600/477 |
| 5,364,390 A | 11/1994 | Taboada et al. | 606/10 |
| 5,368,031 A | 11/1994 | Cline et al. | 600/411 |
| 5,368,634 A | 11/1994 | Hackett | 95/260 |
| 5,370,651 A | 12/1994 | Summers | 606/159 |
| 5,374,265 A | 12/1994 | Sand | 606/5 |
| 5,375,132 A | 12/1994 | Connors et al. | 372/34 |
| 5,382,013 A | 1/1995 | Walsh | 271/186 |
| 5,383,467 A | 1/1995 | Auer | 128/664 |
| 5,384,796 A | 1/1995 | Jee | 372/22 |
| 5,386,837 A | 2/1995 | Sterzer | 128/898 |
| 5,387,211 A | 2/1995 | Saadatmanesh et al. | 606/10 |
| 5,390,204 A | 2/1995 | Yessik et al. | 372/38 |
| 5,394,307 A | 2/1995 | Matsuura | 362/16 |
| 5,395,362 A | 3/1995 | Sacharoff et al. | 606/17 |
| 5,397,327 A | 3/1995 | Koop et al. | 606/17 |
| 5,400,428 A | 3/1995 | Grace | 385/115 |
| 5,400,791 A | 3/1995 | Schlier et al. | 128/664 |
| 5,401,171 A | 3/1995 | Paghdiwala | 433/215 |
| 5,403,276 A | 4/1995 | Schechter et al. | 604/22 |
| 5,405,368 A | 4/1995 | Eckhouse | 607/88 |
| 5,405,726 A | 4/1995 | Abe et al. | 430/97 |
| 5,406,577 A | 4/1995 | Gagosz | 372/69 |
| 5,409,479 A | 4/1995 | Dew et al. | 606/9 |
| 5,409,483 A | 4/1995 | Campbell et al. | 606/15 |
| 5,411,502 A | 5/1995 | Zair | 606/10 |
| 5,414,600 A | 5/1995 | Strobl et al. | 362/551 |
| 5,422,899 A | 6/1995 | Freiberg et al. | 372/25 |
| 5,423,798 A | 6/1995 | Crow | 606/4 |
| 5,423,803 A | 6/1995 | Tankovich et al. | 606/9 |
| 5,425,728 A | 6/1995 | Tankovich | 606/9 |
| 5,431,646 A | 7/1995 | Vassiliadis et al. | 606/6 |
| 5,435,724 A | 7/1995 | Goodman et al. | 433/215 |
| 5,438,303 A | 8/1995 | Murakami et al. | 332/109 |
| 5,441,531 A | 8/1995 | Zarate et al. | |
| 5,445,146 A | 8/1995 | Bellinger | 607/89 |
| D363,349 S | 10/1995 | Dittert | D24/158 |
| 5,454,807 A | 10/1995 | Lennox et al. | 605/15 |
| 5,456,689 A | 10/1995 | Kresch et al. | 606/180 |
| 5,458,112 A | 10/1995 | Weaver | 600/566 |
| 5,474,528 A | 12/1995 | Meserol | 604/20 |
| 5,474,549 A | 12/1995 | Ortiz et al. | 606/9 |
| 5,476,461 A | 12/1995 | Cho et al. | 606/15 |
| 5,484,432 A | 1/1996 | Sand | 606/5 |
| 5,489,279 A | 2/1996 | Meserol | 604/290 |
| 5,490,860 A | 2/1996 | Middle et al. | 606/171 |
| 5,498,258 A | 3/1996 | Hakky et al. | 606/15 |
| 5,498,935 A | 3/1996 | McMahan et al. | 315/241 P |
| 5,501,680 A | 3/1996 | Kurtz et al. | 606/9 |
| 5,511,563 A | 4/1996 | Diamond | 128/898 |
| 5,520,679 A | 5/1996 | Lin | 606/5 |
| 5,522,814 A | 6/1996 | Bernaz | 606/36 |

| | | | |
|---|---|---|---|
| 5,527,332 A | 6/1996 | Clement | 606/171 |
| 5,527,350 A | 6/1996 | Grove et al. | 607/89 |
| 5,529,954 A | 6/1996 | Iijima et al. | 438/653 |
| 5,531,739 A | 7/1996 | Trelles | 606/2.5 |
| 5,531,740 A | 7/1996 | Black | 606/9 |
| 5,540,676 A | 7/1996 | Freiberg | 606/3 |
| 5,544,651 A | 8/1996 | Wilk | 600/310 |
| 5,546,214 A | 8/1996 | Black et al. | 359/203 |
| 5,558,666 A | 9/1996 | Dewey et al. | 606/9 |
| 5,558,667 A | 9/1996 | Yarborough et al. | 606/9 |
| 5,560,699 A | 10/1996 | Davenport et al. | 362/558 |
| 5,569,284 A | 10/1996 | Young et al. | 606/180 |
| 5,572,311 A | 11/1996 | Abe | 399/127 |
| 5,578,029 A | 11/1996 | Trelles et al. | 606/25 |
| 5,586,981 A | 12/1996 | Hu | 606/9 |
| 5,588,428 A | 12/1996 | Smith et al. | 600/425 |
| 5,591,157 A | 1/1997 | Hennings et al. | 606/3 |
| 5,595,568 A | 1/1997 | Anderson et al. | 606/9 |
| 5,599,342 A | 2/1997 | Hsia et al. | 606/9 |
| 5,606,798 A | 3/1997 | Kelman | 30/41.5 |
| 5,608,520 A | 3/1997 | Fleming | 356/318 |
| 5,611,795 A | 3/1997 | Slatkine et al. | 606/9 |
| 5,618,284 A | 4/1997 | Sand | 606/5 |
| 5,618,285 A | 4/1997 | Zair | 606/10 |
| 5,620,478 A | 4/1997 | Eckhouse | 607/88 |
| 5,621,745 A | 4/1997 | Yessik et al. | 372/26 |
| 5,626,631 A | 5/1997 | Eckhouse | 607/88 |
| 5,628,744 A | 5/1997 | Coleman et al. | 606/12 |
| 5,630,811 A | 5/1997 | Miller | 606/9 |
| 5,642,370 A | 6/1997 | Mitchell et al. | 372/25 |
| 5,643,334 A | 7/1997 | Eckhouse et al. | 697/88 |
| 5,644,585 A | 7/1997 | Mitchell et al. | 372/25 |
| 5,649,972 A | 7/1997 | Hochstein | 607/100 |
| 5,655,547 A | 8/1997 | Karni | 128/898 |
| 5,658,323 A | 8/1997 | Miller | 607/89 |
| 5,660,836 A | 8/1997 | Knowlton | 424/400 |
| 5,662,644 A | 9/1997 | Swor | 606/9 |
| 5,683,380 A | 11/1997 | Eckhouse et al. | 606/9 |
| 5,707,413 A | 1/1998 | Inao | 65/78 |
| 5,710,626 A | 1/1998 | O'rourke et al. | 356/301 |
| 5,720,772 A | 2/1998 | Eckhouse | 607/88 |
| 5,722,970 A | 3/1998 | Colvard et al. | 606/3 |
| 5,725,565 A | 3/1998 | Smith | 607/88 |
| 5,733,277 A | 3/1998 | Pallarito | 606/7 |
| 5,733,297 A | 3/1998 | Wang | 606/167 |
| 5,735,844 A | 4/1998 | Anderson et al. | 606/9 |
| 5,738,677 A | 4/1998 | Colvard et al. | 606/4 |
| 5,741,245 A | 4/1998 | Cozean et al. | 606/5 |
| 5,743,902 A | 4/1998 | Trost | 606/18 |
| 5,748,655 A | 5/1998 | Yessik et al. | 372/22 |
| 5,749,868 A | 5/1998 | Furumoto | 606/9 |
| 5,754,573 A | 5/1998 | Yarborough et al. | 372/22 |
| 5,755,751 A | 5/1998 | Eckhouse | 607/88 |
| 5,755,753 A | 5/1998 | Knowlton | 607/98 |
| 5,769,844 A | 6/1998 | Ghaffari | 606/16 |
| 5,776,175 A | 7/1998 | Eckhouse et al. | 607/100 |
| 5,783,798 A | 7/1998 | Abraham | 219/121.73 |
| 5,786,929 A | 7/1998 | Nabors | 359/330 |
| 5,810,801 A | 9/1998 | Anderson et al. | 606/9 |
| 5,814,040 A | 9/1998 | Nelson et al. | 606/9 |
| 5,817,089 A | 10/1998 | Tankovich et al. | 606/9 |
| 5,817,090 A | 10/1998 | Abergel et al. | 606/9 |
| 5,828,803 A | 10/1998 | Eckhouse | 385/88 |
| 5,830,208 A | 11/1998 | Muller | 606/9 |
| 5,833,612 A | 11/1998 | Eckhouse | 600/476 |
| 5,833,683 A | 11/1998 | Fuller et al. | 606/17 |
| 5,836,939 A | 11/1998 | Negus et al. | 606/11 |
| 5,836,999 A | 11/1998 | Eckhouse et al. | 607/88 |
| 5,843,143 A | 12/1998 | Whitehurst | 607/88 |
| 5,849,029 A | 12/1998 | Eckhouse et al. | 607/104 |
| 5,853,407 A | 12/1998 | Miller | 606/9 |
| 5,855,595 A | 1/1999 | Fujishima et al. | 607/90 |
| 5,860,967 A | 1/1999 | Zavislan et al. | 606/9 |
| 5,860,968 A | 1/1999 | Wojcik et al. | 606/10 |
| 5,865,830 A | 2/1999 | Parel et al. | 606/5 |
| 5,871,479 A | 2/1999 | Furumoto et al. | 606/9 |
| 5,879,346 A | 3/1999 | Waldman et al. | 606/9 |
| 5,879,376 A | 3/1999 | Miller | 607/89 |
| 5,885,273 A | 3/1999 | Eckhouse et al. | 606/9 |
| 5,885,274 A | 3/1999 | Fullmer | 606/9 |
| 5,900,211 A | 5/1999 | Dunn et al. | 422/24 |
| 5,906,609 A | 5/1999 | Assa et al. | 606/9 |
| 5,907,574 A | 5/1999 | Karni | 372/95 |
| 5,911,718 A | 6/1999 | Yarborough et al. | 606/9 |
| 5,912,457 A | 6/1999 | McQuaid | 240/227.17 |
| 5,938,657 A | 8/1999 | Assa et al. | 606/9 |
| 5,957,915 A | 9/1999 | Trost | 606/13 |
| 5,970,983 A | 10/1999 | Karni et al. | 128/898 |
| 5,983,900 A | 11/1999 | Clement et al. | 128/898 |
| 6,024,751 A | 2/2000 | Lovato et al. | 606/170 |
| RE36,634 E | 3/2000 | Ghaffari | 606/9 |
| 6,045,548 A | 4/2000 | Furumoto et al. | 606/9 |
| 6,077,294 A | 6/2000 | Cho et al. | 607/89 |
| 6,090,101 A | 7/2000 | Quon et al. | 606/9 |
| 6,096,031 A | 8/2000 | Mitchell et al. | 606/15 |
| 6,130,900 A | 10/2000 | Black et al. | 372/25 |
| 6,139,712 A | 10/2000 | Patton et al. | 205/143 |
| 6,165,170 A | 12/2000 | Wynne et al. | 606/9 |
| 6,171,302 B1 | 1/2001 | Talpalriu et al. | 606/9 |
| 6,171,332 B1 | 1/2001 | Whitehurst | 607/89 |
| 6,190,376 B1 | 2/2001 | Asah et al. | 606/9 |
| 6,193,711 B1 | 2/2001 | Connors et al. | 606/12 |
| 6,235,016 B1 | 5/2001 | Stewart | 606/9 |
| 6,280,438 B1 | 8/2001 | Eckhouse et al. | 606/9 |
| 6,282,223 B1 | 8/2001 | Angeley | 372/92 |
| 6,289,236 B1 | 9/2001 | Koenig et al. | 600/477 |
| 6,379,376 B1 | 4/2002 | Lubart | 607/88 |
| 6,387,089 B1 | 5/2002 | Kreindel et al. | 606/9 |
| 6,451,010 B1 | 9/2002 | Angeley | 606/17 |
| 6,475,138 B1 | 11/2002 | Schechter et al. | 600/108 |
| 6,505,059 B1 | 1/2003 | Kollias et al. | 600/316 |
| 6,514,243 B1 | 2/2003 | Eckhouse et al. | 606/9 |
| 6,522,911 B1 | 2/2003 | Toida et al. | 600/473 |
| 6,544,585 B1 | 4/2003 | Hongo et al. | 216/18 |
| 6,702,838 B1 | 3/2004 | Andersen et al. | 607/89 |
| 6,766,187 B1 | 7/2004 | Black et al. | 600/473 |

FOREIGN PATENT DOCUMENTS

| | | |
|---|---|---|
| CA | 2168624 | 8/1996 |
| CH | 416861 | 7/1966 |
| DE | 565331 | 11/1932 |
| DE | 2308554 | 8/1974 |
| DE | 2740179 | 3/1978 |
| DE | 27 17 421 A1 | 11/1978 |
| DE | 2717421 | 11/1978 |
| DE | 2740969 | 3/1979 |
| DE | 7901050 | 5/1979 |
| DE | 2901534 | 7/1979 |
| DE | 2846471 | 5/1980 |
| DE | 2948580 | 6/1980 |
| DE | 3220218 | 3/1983 |
| DE | 3330293 | 3/1985 |
| DE | 3804732 | 8/1989 |
| DE | 3906860 | 9/1989 |
| DE | 4031320 A | 4/1992 |
| DE | 9304869 | 9/1993 |
| DE | 9321497 | 8/1998 |
| EP | 0003312 | 8/1979 |
| EP | 0052765 | 6/1982 |
| EP | 0075860 | 4/1983 |
| EP | 0172490 | 2/1986 |
| EP | 0185810 | 7/1986 |

| | | |
|---|---|---|
| EP | 0198257 | 10/1986 |
| EP | 0240990 | 10/1987 |
| EP | 0310285 | 4/1989 |
| EP | 0324490 | 7/1989 |
| EP | 0335714 | 10/1989 |
| EP | 0429297 | 5/1991 |
| EP | 0480995 | 4/1992 |
| EP | 0527050 | 2/1993 |
| EP | 0565331 A2 | 10/1993 |
| EP | 0575274 | 12/1993 |
| EP | 0626229 | 11/1994 |
| EP | 0724292 | 7/1996 |
| EP | 0724894 | 8/1996 |
| EP | 0736308 | 10/1996 |
| EP | 0753285 A1 | 1/1997 |
| EP | 0763371 | 3/1997 |
| EP | 0807418 | 11/1997 |
| EP | 0880168 | 11/1998 |
| EP | 0885629 | 12/1998 |
| EP | 1078604 | 2/2001 |
| EP | 1078605 | 2/2001 |
| ES | 8306601 | 9/1983 |
| FI | 822940 | 3/1983 |
| FI | 0931608 | 10/1993 |
| FR | 2193628 | 2/1974 |
| FR | 2342745 | 9/1977 |
| FR | 2364038 | 4/1978 |
| FR | 2389229 | 11/1978 |
| FR | 2571264 | 4/1986 |
| GB | 1116465 | 6/1968 |
| GB | 2012939 | 8/1979 |
| GB | 2105195 | 3/1983 |
| GB | 2218660 | 11/1989 |
| HU | 181836 | 11/1983 |
| HU | 186081 | 5/1985 |
| IL | 101547 | 12/1996 |
| JP | 52109387 | 9/1977 |
| JP | 53105083 | 9/1978 |
| JP | 55117166 | 9/1980 |
| JP | 56109654 | 8/1981 |
| JP | 56124451 | 9/1981 |
| JP | 56137140 | 10/1981 |
| JP | 58086178 | 5/1983 |
| JP | 60006871 | 1/1985 |
| JP | 60132571 | 7/1985 |
| JP | 62114543 | 5/1987 |
| JP | 63277771 | 11/1988 |
| JP | 1034378 | 2/1989 |
| JP | 64012402 | 2/1989 |
| JP | 1240694 | 9/1989 |
| JP | 2154753 | 6/1990 |
| JP | 3016956 | 1/1991 |
| JP | H3-128069 | 5/1991 |
| JP | 3211287 | 9/1991 |
| JP | 3233986 | 10/1991 |
| JP | HEI 4-53569 | 2/1992 |
| JP | HEI-4-53569 | 2/1992 |
| JP | 4067860 | 3/1992 |
| JP | 4079966 | 3/1992 |
| JP | 4-90360 | 8/1992 |
| JP | 5001559 | 1/1993 |
| JP | 5029089 | 2/1993 |
| JP | 5111539 | 5/1993 |
| JP | 6063165 | 3/1994 |
| JP | 6198945 | 7/1994 |
| JP | 7008281 | 1/1995 |
| JP | 7275380 | 10/1995 |
| JP | 7308300 | 11/1995 |
| JP | 86266326 | 10/1996 |
| LU | 84349 | 6/1983 |
| SE | 416861 | 2/1981 |
| SE | 452852 | 12/1987 |
| SE | 465 953 B | 11/1991 |
| SE | 515325 | 7/2001 |
| SU | 1347142 | 10/1987 |
| WO | 80/02640 | 12/1980 |
| WO | 84/03049 | 8/1984 |
| WO | 84/04463 | 11/1984 |
| WO | 89/00871 | 2/1989 |
| WO | 89/11261 | 11/1989 |
| WO | 90/12545 | 11/1990 |
| WO | 90/14836 | 12/1990 |
| WO | 91/00063 | 1/1991 |
| WO | 91/12766 | 9/1991 |
| WO | 91/13652 | 9/1991 |
| WO | WO-91/15264 | 10/1991 |
| WO | 91/15264 | 10/1991 |
| WO | 92/19165 | 11/1992 |
| WO | 93/008715 | 5/1993 |
| WO | 95/15725 | 6/1995 |
| WO | 96/21490 | 7/1996 |
| WO | 96/32895 | 10/1996 |
| WO | 96/33538 | 10/1996 |
| WO | 96/41577 | 12/1996 |
| WO | 97/37602 | 10/1997 |
| WO | 98/52645 | 11/1998 |
| WO | 99/25905 | 5/1999 |
| WO | 99/55243 | 11/1999 |
| WO | 00/32835 | 6/2000 |

OTHER PUBLICATIONS

Alster et al., "Treatment of Scars: A Review", *Annuals of Plastic Surgery,* 39(4):418–432 (Oct. 1997).

Anderson et al., "Selective Photothermolysis: Precise Microsurgery by Selective Absorption of Pulsed Radiation", *Science,* 220:524–527 (Apr. 1993).

Anderson et al., "Pulsed photothermal radiometry in turbid media: internal reflection of backscattered radiation strongly influences optical dosimetry", *Applied Optics,* 28(12):2256–2262 (1989).

Anderson et al., "Microvasculature can be selectively damaged using dye lasers: basic theories and experimental evidence in human skin", *Laser in Surg. Med.,* 1:263–276 (1981).

Arthrex, Inc. "Single Use Shaver Blades and Burs", (1996).

Birngruber et al., "Fundus Reflectometry: A Step towards Optimization of the Retina Photocoagulation", *Mod. Probl, Ophthal.,* 18:383–390 (1977).

Blitzer, "Laser Photocoagulation in the Care of Patients with Osier—Weber—Rendu Disease", *Operative Techniques in Otolaryngology—Head and Neck Surgery,* 5(4):274–277 (Dec. 1994).

Boulnois, "Photophysical Processes in Recent Medical Laser Developments: A Review", *Lasers in Medical Science,* 1:47–64 (1986).

Brauner et al., "Treatment of Pigmented Lesions with the Flashlamp Pumped PL DL ("Brown Spot") Laser", *Laser Med. And Surgery Abstracts,* 4:73 (Sep. 1992).

Cisneros et al., "The Q–Switched Neodymium (Nd): YAG Laser with Quadruple Frequency", *Dermatol. Surg.,* 24:345–350 (1998).

Dagan et al., "Microprocessor—Controlled Scanning Micromanipulator for Carbon—Dioxide Laser Surgery", *J. Neurosurgery,* 59:1098–1099 (Dec. 1983).

Fitzpatrick et al., "Treatment of Benign Cutaneous Pigmented Lesions with the Candela 510 NM Pulsed Laser", *Laser Med. and Surgery Abstracts,* 4S:73 (Sep. 1992).

Frauchiger et al., "Laser properties of selectively excited YA10.sub.3 :Er", *Optics Letters,* 13(11):964–966 (1988).

Gabay et al., "Modelling the Assessment of Port Wine Stain Parameters From Skin Surface Temperature Following a Diganostic Laser Pulse", *Lasers in Surgery and Medicine,* 20(2):179–187 (1997).

Geeraets et al., "Light Reflectance of the Ocular Fundus", *Archives of Ophthalmology,* 69:612–617 (May 1963).

Gustafsson et al., "A Variable Pulsewidth Vascular System for Dermatology", *SPIE,* 2128:186–196 (1994).

Hacker et al., "The Effect of Flash Lamp–Pulsed Dye Laser on Psoriasis", *Archives of Dermatology,* 128:853–855 (Jun. 1992).

Herloski et al., "Gaussiab beam ray–equivalent modelling and optical design", *Applied Optics,* 22(8):1168–1174 (1983).

International Search Report, dated Jul. 24, 1996, for International Application No. PCT/US96/04515, 4 pages.

Ishimaru, "Diffusion of Light in Turbid Material", *Applied Optics,* 28(12):2210–2215 (1989).

Jacques et al., "The Role of Skin Optics in Diagnostic and Therapeutic Uses of Lasers", *Lasers in Dermatology,* 1–21 (1991).

Jerath et al., "Calibrated real–time control for lesion size based on reflectance images", *Applied Optics,* 32(7):1200–1209 (Mar. 1993).

Jerath et al., "Reflectance Feedback Control of Photocoagulation In Vivo", *Arch Ophthalmol,* 111:531–534 (Apr. 1993).

Jeys et al., "Sum frequency generation of sodium resonance radiation", *Applied Optics,* 28(13):2588–2591 (1989).

Kaufman et al., "Clinical Evaluation of Pulsed Erbium:YAG Laser Ablation in Cutaneous Surgery", (Abstract), *Partly Presented at 15th Annual Mtg of the American Society for Laser/Medicine and Surgery,* (1995).

Kauvar et al., "Laser Therapy for Cutaneous Vascular Lesions", *Operative Techniques in Otolaryngology—Head and Neck Surgery,* 5(4):250–258 (Dec. 1994).

Kienle et al., "Why do veins appear blue? A new look at an old question", *Applied Optics,* 35(7):1151–1160 (1996).

Lahaye et al., "Optimal laser parameters for port wine stain therapy: a theoretical approach", *Phys. Med. Biol.,* 30(6):573–587 (1995).

LaserSight Centers brochure, "CENTAURI.TM. Ophthalmic Erbium:Yag Laser", (Nov. 1993).

Lesinski et al., "Carbon Dioxide Lasers for Otosclerosis", *Otolaryngologic Clinics of North America,* 26(3)417–441 (Jun. 1993).

Lewis et al., "Backscattering target detection in a turbid medium by polarization discrimination", *Applied Optics,* 38(18):3937–3944 (Jun. 1999).

Lytle et al., "Improved Efficacy of SnET2 Mediated PDT With the Simultaneous Application of Selective Laser—Induced Hyperthermia", *SPIE Proceedings,* 2392–6:15–22.

Maloney et al., "Laser Otology", *Operative Techniques in Otolaryngology—Head and Neck Surgery,* 3(2):74–83 (Jun. 1992).

Milner et al., "Depth determination of chromophores in human skin by pulsed photothermal radiometry," *Applied Optics,* 35(19):3379–3385 (Jul. 1996).

Milner et al., "Depth profiling of laser–heated chromophores in biological by pulsed photothermal radiometry", *Journal of the Optical Society of America A,* 12(7):1479–1488 (Jul. 1995).

Minamihaba et al., "Double–Level CU Inlaid Interconnects with Simultaneously Filled Viaplugs" *Japanese Journal of Applied Physics,* 35(2B):1107–1110 (Feb. 1996).

Mordon et al., "Relation Between Skin Surface Temperature and Minimal Blanching During Argon, Nd–YAG 532, and CW Dye 585 Laser Therapy of Port–Wine Stains," *Lasers in Surgery and Medicine,* 13(1):124–126 (1993).

Morreli et al., "Tunable Dye Lasers (577 nm) Treatment of Port Wine Stains", *Lasers Surg. Med.,* 6(1):94–99 (1986).

Orenberg et al., "Comparison of heat delivery systems for hyoerthemia treatment of psoriasis", *Int. J. Hyperthemia,* 2(3):231–241 (1986).

Pai et al., "Selective Electroless Copper for FLSI Interconnection", *IEEE Electron Device Letters,* 10(9):423–425 (1989).

Patent Abstracts of Japan, vol. 012, No. 337 (E–657), Sep. 12, 1988 & JP 63 100749 A (Hitachi Ltd.), May 2, 1988.

Patent Abstracts of Japan, vol. 016, No. 263 (D–1216), Jun. 15, 1992 & JP 04 061125 A (Kanegafuchi Chem. Ind. Co. Ltd.), Feb. 27, 1992.

Patent Abstracts of Japan, vol. 018, No. 480 (E–1603), Sep. 8, 1994 & JP 06 164140 A (Ibiden Co. Ltd.), Jun. 10, 1994.

Patent Abstracts of Japan, vol. 4, No. 172 (P–038), Sep. 9, 1980.

Petrovich et al., "Relationship of Response to Transurethral Hyperthermia and Prostate Volume in BPH Patients", *Urology,* 40(4):317–321 (Oct. 1992).

Polla, et al., "Tunable Pulsed Dye Laser for the Treatment of Benign Cutaneous Vascular Ectasia", *Drematologica,* 174:11–17 (1987).

Pornerantzeff et al., "A Method to Predetermine the Correct Photocoagulation Dosage", *Arch Ophthalmol,* 101:949–953 (1983).

Pornerantzeff et al., "Time and Location Analysis of Lesion Formation in Photocoagulation", *Arch Ophthalmol,* 101:954–957 (1983).

Sausville et al., "Blue Lamps in Phototherapy of Hyperbilrubinemia", *Journal of IES,* 112–118 (1972).

Semm et al., "Tissue Morcellation In Endoscopic Surgery", *Surgical Technology International V, International Developments In Surgery & Surgical Research,* 175–178. (1996).

Slatkine et al., "Instrumentation for Office Laser Surgery", *Operative Techniques in Otolaryngology—Head and Neck Surgery,* 5(4):211–217 (Dec. 1994).

Smith & Nephew, Inc., "Shaver Systems–Endoscopic Powered Instruments System", Mar. 1997.

Smith et al., "The Design of Optical Systems", *Modern Optical Engineering,* 273–278 (1990).

Smithies et al., "The Effect of the Illumination Time When Treating Port–wine Stains", *Lasers in Medical Science,* 10(2):93–104 (1995).

Taylor et al., "Light & Electron Microscopic Analysis of Tattoss Treated by O–Switched Ruby Laser", *J. of Investigative Dermatology,* 97:131–136 (1991).

Van–Gemert et al., "Treatment of Port–Wine Stains: Analysis", *Medical Instrumentation,* 21:213–217 (1987).

Waldow et al., "Nd: YAG Laser–Induced Hyperthermia In A Mouse Tumor Model", *Lasers in Surgery and Medicine,* 8(5)510–514 (1988).

Weinberg et al., "The Change in Light Reflection of the Retina During Therapeutic Laser–Photocoagulation," *IEEE J. Quantum Electronics,* QE–20(12):1481–1489 (1984).

Wright et al., "Initial in vivo results of hybrid retinal photo-coagulation system", *Journal of Biomedical Optics*, 5(1):56–61 (Jan. 2000).

Yang et al., "Automatic Control of Lesion Size in a Simulated Model of the Eye", *IEEE Journal of Quantum Electronics*, 26(12):2232–2239 (1990).

Yang et al., "Reflectance as an Indirect Measurement of the Extent of Laser–Induced Coagulation," *IEEE Transactions on Biomedical Engineering*, 37(5):466–473 (1990).

Zee et al, "Whole–Body Hyperthermia in Cancer Therapy: A Report of a Phase I–II Study" *Eur. J., Cancer Clinical Oncology*, 19(9):1189–1200 (1983).

Zimmer information brochure, "Arthroscopic Blades and Burrs", (1996).

File history for EP0565331, Various Dates.

Deposition transcript of Lars Ake Morgan Gustavsson (Dec. 10, 2007).

*Lumenis Ltd., et al. v. Alma Ltd., et al.,* 07:CV3622, N.D.III.—Complaint (Jun. 28, 2007).

*Lumenis Ltd., et al. v. Alma Ltd., et al.,* 07:CV3622, N.D.III.—Joint Claim Construction Statement (Jan. 4, 2008).

*Lumenis Ltd., et al. v. Alma Ltd., et al.,* 07:CV3622, N.D.III.—Plaintiffs' Opening Claim Construction Brief) (Jan. 7, 2008).

*Lumenis Ltd., et al. v. Alma Ltd., et al.,* 07:CV3622, N.D.III.—Plaintiffs' Reply to Defendants' Responsive Claim Construction Brief (Jan. 22, 2008).

*Lumenis Ltd., et al. v. Alma Ltd., et al.,* 07:CV3622, N.D.III.—Plaintiffs' Demonstratives for Markman Hearing (Jan. 23, 2008).

*Lumenis Ltd., et al. v. Alma Ltd., et al.,* 07:CV3622, N.D.III.—Defendants' Amended Answer, Affirmative Defenses, and Counterclaims (Jan. 25, 2008).

*Lumenis Ltd., et al. v. Alma Ltd., et al.,* 07:CV3622, N.D.III.—Plaintiffs' Reply to Defendants' Counterclaim (Feb. 14, 2008).

*Lumenis Ltd., et al. v. Alma Ltd., et al.,* 07:CV3622, N.D.III.—Plaintiffs' Further Supplemental Answers to Defendants' First Set of Interrogatories to Plaintiffs (Nos. 3 an 11) (Feb. 1, 2008).

*Lumenis Ltd., et al. v. Alma Ltd., et al.,* 07:CV3622, N.D.III.—Plaintiffs' Rule 26(a)(1) Initial Disclosures to Defendants (Oct. 29, 2007).

*Lumenis Ltd., et al. v. Alma Ltd., et al.,* 07:CV3622, N.D.III.—Defendants' Initial Disclosures Pursuant to Fed. R. Civ. P. 26(a) (Oct. 29, 2007).

*Lumenis Ltd., et al. v. Alma Ltd., et al.,* 07:CV3622, N.D.III.—Plaintiffs' Answers to Defendants' First Set of Interrogatories to Plaintiffs (Nov. 19, 2007).

*Lumenis Ltd., et al. v. Alma Ltd., et al.,* 07:CV3622, N.D.III.—Plaintiffs' Supplemental Answers to Defendants' First Set of Interrogatories to Plaintiffs (Nos. 2, 5, 8 & 15) (Dec. 14, 2007).

*Lumenis Ltd., et al. v. Alma Ltd., et al.,* 07:CV3622, N.D.III.—Plaintiffs' Further Supplemental Answers to Defendants' First Set of Interrogatories to Plaintiffs (Nos. 7, 11 & 12) (Dec. 21, 2007).

*Lumenis Ltd., et al. v. Alma Ltd., et al.,* 07:CV3622, N.D.III.—Plaintiffs' Further Supplemental Answers to Defendants' First Set of Interrogatories to Plaintiffs (No. 3) (Dec. 27, 2007).

*Lumenis Ltd., et al. v. Alma Ltd., et al.,* 07:CV3622, N.D.III.—Plaintiffs' Answers to Defendants'Second Set of Interrogatories to Plaintiffs (Nos. 16–18) (Dec. 28, 2007).

*Lumenis Ltd., et al. v. Alma Ltd., et al.,* 07:CV3622, N.D.III.—Plaintiffs' Supplemental Answers to Defendants' Second Set of Interrogatories to Plaintiffs (No. 18) (Jan. 14, 2008).

"Aesthetic CO2 Laser System", literature, 2 pages, (Aug. 1994).

"New Laser for Microlaryngeal Surgery", *I.L.. Med. Newsletter*, 1(1) (Spring 1991).

"The Er:YAG Laser System for ophthalmic microsurgery", *Aesculap Meditec brochure*, 2 pages, (Oct. 1994).

"The Proven Solution for Disk, Spinal Cord and Brain Microsurgery", *I. L. Med. Unilase product info. Brochure* (1993).

"The Proven Solution for Otologic and Microlaryngeal Surgery", *I. L. Med. Unilase product info. Brochure* (1993).

"Using a CO2 Laser During Conventional Microdisketomy Shows Promise of Faster Recovery", *I.L. Med Newsletter*, 1(4) (Spring 1991).

"Control of Pulse Duration and Pulse Sequence Delays for Effective Photo–Epilation", *EpiLight™ Application Notes*, 3(2) (1997).

Adrian, "LightSheer™ 800 NM Pulsed. High–Power Diode Laser Hair Removal System", (2002).

Adrian, "Tissue Effects of a New Long Pulse Frequency Doubled 532 nm Neodymium: YAG Laser on Vascular Lesions", (2001).

Adrian, "Treatment of Facial Telangiectasia Using the VersaPulse® Variable Pulse Width Frequency Doubled Neodymium:YAG Laser: A Case Report", (2001).

Anderson et al., "Microvasculature Can Be Selectively Damaged Using Dye Lasers: A Basic Theory and Experimental Evidence in Human Skin", *Laser in Surgery and Medicine*, 1:263–276 (1981).

Anderson et al., "The Optics of Human Skin", *The Journal of Investigative Dermatology*, 77(1):13–19 (Jul. 1981).

Anderson, "Laser Hair Removal—A Lecture Presented to the 77th Congress of the Japan Society of Aesthetic Surgery", (Nov. 1999).

Bandel, "Effective Resolution of a Mature Port–Wine Stain Using PhotoDerm®VL", *Clinical Application Notes*, 1(2) (1998).

Bartley et al., "An Experimental Study to Compare Methods of Eyelash Ablation", *Ophthalmology*, 94(10):1286–1289 (Oct. 1987).

Battle et al., "Study of Very Long–Pulsed (100 ms) High–Powered Diode Laser for Hair Reduction on All Skin Types", (2002).

Beasley et al., "New Parameters for Intense Pulsed Light Rejuvination With a Thermoelectrically Chilled Crystal Delivery System", *Cosmetic Dermatology*, 15(7):14–16 (Jul. 2002).

Bitter, "Noninvasive Rejuvenation of Photodamaged Skin Using Serial, Full–Face Intense Pulsed Light Treatments", *Dermatol Surg.*, 26(9):835–43 (Sep. 2000).

Campos et al., "Use of an 800 nm High–power Diode Laser for the Treatment of Leg Vein Telangiectasia", (2002).

Campos, "Safe and Effective Long–Term Hair Reduction in Tanned Patients Using an 800 nm Diode Laser", (2002).

Del Giglio, "Hair Removal Using a Combination of Electrical and Optical Energies—3–Month Clinical Study", 1–4 (Not Dated).

Del Giglio, "Hair Removal Using a combination of Electrical and Optical Energies: Multiple Treatments Clinical Study—Six–Month Follow up", 1–4 (Not Dated).

Dierickx et al., "Effective, Permanent Hair Reduction Using a Pulsed, High–Power Diode Laser", (2002).

Dierickx, "Laser Hair Removal: Scientific Principles and Practical Aspects", (2002).

Dover et al., "Pigmented Guinea Pig Skin Irradiated With Q–Switched Ruby Laser Pulses", *Arch Dermatol*, 125(1):43–44 (Jan. 1989).

Dréno et al., "The Benefit of Chilling in Argon–Laser Treatment of Port–Wine Stains", *Plast Reconstr Surg.*, 75(1):42–45 (Jan. 1985).

Dzubow, "Leg Veins and Stretch Marks—Have They Seen the Light?", *Dermatol Surg.*, 22(4):321 (Apr. 1996).

Eckhouse et al., "The Application of Selective Photothermolysis in Treating Leg Veins and Other Benign Vascular Lesions", (Apr. 1996).

ESC Medical Systems, "Eliminating Multicolored Tattoos with PhotoDerm®PL", *PhotoDerm® Application Notes*, 2(2) (1997).

ESC Medical Systems, "Facial and truncal angiomas—treating patients quickly and effectively", *PhotoDerm® Application Notes*, 1(2) (1996).

ESC Medical Systems, "How does it look in theory?", (1996).

ESC Medical Systems, "Significance of Wavelength Range for Effective Hair Photo–Epilation", *EpiLight Hair Removal System Application Notes*, 3(1) (1997).

ESC Medical Systems, "Superior Treatment of Benign Pigmented Lesions with PhotoDerm® PL", *PhotoDerm® Application Notes*, 2(1) (1997).

ESC Medical Systems, "Why are leg veins so difficult to treat?", *PhotoDerm®VL Application Notes*, 1(1) (1996).

Gilchrest et al., "Chilling Port Wine Stains Improves the Response to Argon Laser Therapy", *Plast Reconstr Surg.*, 69(2):278–83 (Feb. 1982).

Gold et al., "Intense Pulsed Light (IPL™) System Enables Successful Treatment of Skin Type VI", *Clinical Application Notes*, 2(5) (2000).

Gold et al., "Long–term epilation using the EpiLight broad band, intense pulsed light hair removal system", *Dermatol Surg.*, 23(10):909–913 (Oct. 1997).

Gold, "Treatment of Larger and Deeper Varicosities Utilizing a 1064 nm Laser System", *Cosmetic Dermatology*, (Nov. 2000).

Goldman, "Effects of New Laser Systems on the Skin" *Arch. Dermatol.*, 108:385–390 (Sep. 1973).

Goldman et al., "Impact of the Laser on Nevi and Melanomas", *Arch Dermatol*, 90:71–75 (Jul. 1964).

Goldman et al., "Laser Treatment of Tattoos—A Preliminary Survey of Three Year's Clinical Experience", *JAMA*, 201(11):163–166 (Sep. 1967).

Goldman et al., "Long–Term Laser Exposure of a Senile Freckle", *Arch. Environ. Health*, 22:401–403 (Mar. 1971).

Goldman et al., "Pathology of the Effect of the Laser Beam on the Skin", *Nature*, 197:912–914 (Mar. 1963).

Goldman et al., "Photothermal Sclerosis of Leg Veins", *Dermatol Surg.*, 22(4):323–30 (Apr. 1996).

Goldman et al., "Preliminary Investigation of Fat Embolization from Pulsed Ruby Laser Impacts of Bone", *Nature*, 221:361–363 (Jan. 1969).

Goldman et al., "Radiation from a Q–Switched Ruby Laser, Effect of Repeated Impacts of Power Output of 10 Megawatts on a Tattoo of Man", *The Journal of Investigative Dermatology*, 44:69–71 (Jan. 1965).

Goldman et al., "Replica Microscopy and Scanning Electron Microscopy of Laser Impacts on the Skin", *The Journal of Investigative Dermatology*, 52(1):18–24 (Jan. 1969).

Goldman et al., "The Biomedical Aspects of Lasers", *JAMA*, 188(3):230–234 (Apr. 1964).

Goldman et al., "The Effect of Repeated Exposures to Laser Beams", *Acta derm.–venereol*, 44:264–268 (1964).

Goldman et al., "Treating Varicose and Telangiectatic Leg Veins", *Federal Practitioner*, (Mar. 1997).

Goldman et al., "Treatment of Basal Cell Epithelioma by Laser Radiation", *JAMA*, 189:773–5 (Sep. 1964).

Goldman, "Dermatologic manifestations of Laser radiation", S92–S93 (Not Dated).

Goldman, "Laser Surgery for Skin Cancer", *New York State Journal of Medicine*, (Oct. 1977).

Goldman, "One Laser For A Cosmetic Dermatologic Practice", *Cosmetic Dermatology*, 15(7):49–50 (Jul. 2002).

Goldman, "Surgery by Laser for Malignant Melanoma", *J. Dermatol. Surg. Oncol.*, 5(2) (Feb. 1979).

Goldman, "The Skin", *Arch Environ Health*, 18:434–436 (Mar. 1969).

Herloski et al., "Gaussian beam ray–equivalent modeling and optical design", *Applied Optics*, 22(8):1168–1174 (Apr. 1983).

Huang et al., "Intense Pulsed Light for the Treatment of Facial Freckles in Asian Skin", *Dermatol Surg.*, 29(11):1008–1012 (Nov. 2002).

Hunt et al., "Treatment of Large Body Areas with EpiLight® Hair Removal System: Multi–Center Back Epilation", *Clinical Application Notes*, 2(2):1–4 (1998).

Inderfurth et al., "Dynamic Reflectometer for Control of Laser Photocoagulation on the Retina", *Lasers in Surgery and Medicine*, 15(1):54–61 (May 1994).

Jay, "Photo–Epilation with the EpiLight™ Hair Removal System: Multi–case Study", *Clinical Application Notes*, 2(3) (1998).

Johnson et al., "Intense pulsed light treatment of hirsutism: case reports of skin photoypes V and VI", *Journal of Cutaneous Laser Therapy*, 1:233–237 (1999).

Karpen, "Treating Benign Vascular Lesions of the Lower Extremities Past, Present, and Future", *Journal of Clinical Laser Medicine & Surgery*, 12(2):111–112 (1994).

Kautz et al., "Early Intervention in Pediatric Hemangiomas with the VascuLight™ Intense Pulsed Light / Laser Source", *Clinical Application Notes*, 8(4) (2000).

Kazmi, "Laser Hair Removal with an 800nm Diode Laser–A Retrospective Study of 1000 Women with Skin Types II to VI", (Jun. 2002).

Klavuhn, "Coverage Rate: The Influence of Laser Parameters on Treatment Time", *Laser Removal Note No. 3*, (Mar. 2000).

Klavuhn, "Epidermal Protection: A Comparative Analysis of Sapphire Contact and Cryogen Spray Cooling", *Laser Hair Removal Technical Note No. 1*, (Jan. 2000).

Klavuhn, "Illumination Geometry: The Importance of Laser Beam Spatial Characteristics", *Laser Hair Removal Technical Note No. 2*, (Feb. 2000).

Kono et al., "Diode Laser–Assisted Hair Removal in Asians: A Study of 101 Japanese Patients", (2000).

Kreindel et al., "Electro–Optical Synergy (ELOS™) Technology for Aesthetic Medicine—Light Triggering Effect on RF Selectivity", 1–4, (Not Dated).

Kreindel et al., "Electro–Optical Synergy (ELOS™) Technology for Aesthetic Medicine Advantages and limitations of various forms of electromagnetic energy for safe and effective hair removal", 1–4 (Not Dated).

Kuriloff et al., "Pharyngoesophageal hair growth: The role of laser epilations", *Otolaryngol Head Neck Surg.*, 98(4):342–5 (Apr. 1988).

Lask et al., "The role of laser and intense light sources in photo–epilation: a comparative evaluation", *Journal of Cutaneous Laser Therapy*, 1:3–13 (1999).

Laughlin, "Effective Epilation of a white hair using combined radio–frequency and optical energy", (Not Dated).

Laughlin, "Epilation in dark skin (types V and VI) with integrated radio–frequency and optical energy", 23–26 (Not Dated).

Levy, "Intense pulsed light treatment for chronic facial erythema of systemic lupus erythematosus: a case report", *Journal of Cutaneous Laser Therapy*, 2(4):195–198 (Dec. 2000).

Lou et al., "Prospectives Study of Hair Reduction by Diode Laser (800nm) with Long–Term Follow Up", *Dermatol Surg.*, 26(5):428–432 (May 2000).

Lumenis Inc., "IPL Skin Treatments using Photorejuvenation: helps restore the skin's youthful look", (2002).

Lumenis Inc., "VascuLight: Intense Pulsed Light and Laser Technology", (2002).

Lumenis Inc., "VascuLight Elite: Intense Pulsed Light and Laser Technology", (2002).

McCoy et al., "An Evaluation of the Copper–Bromide Laser for Treating Telangiectasia", *Dermatol. Surg.*, 22:551–557 (1996).

Moraga, "European Multi–Center Study: VascuLight® for the Treatment of Varicose Veins and Leg Telagiectasias, as well as Other Vascular Lesions", *Clinical Application Notes*, 8(1) (2001).

Moretti, "IPL Photorejuvenation Popularity Spreads Rapidly", *Aesthetic Buyers Guide*, (Mar. 2001).

Moretti, "Laser–Based Technology Expands Treatment Options", *Medical Laser Insight*, (Apr. 1997).

Negishi et al., "Full–Face Photorejuvenation of Photodamaged Skin by Intense Pulsed Light with Integrated Contact Cooling: Initial Experiences in Asian Patients", *Lasers in Surgery and Medicine*, 30(4):298–305 (2002).

Negishi et al., "Photorejuvenation for Asian Skin by Intense Pulsed Light", *Dermatol Surg*, 27:7:627–32 (Jul. 2001).

Nestor et al., "Photorejuvenation Non–Ablative Skin Rejuvenation Using Intense Pulse Light" (Not dated).

Pardo et al., "Use of the LightSheer™ Diode Laser System for Hair Reduction: Safety and Efficay in a Large Series of Treatments", (Feb. 2001).

Parrish et al., "Selective Thermal Effects with Pulsed Irradiation from Lasers: From Organ to Organelle", *The Journal of Investigative Dermatology*, 80(6): 75s–80s (Jun. 1963).

Pervaiz et al., "A New Method of Quatitating Damage to the Hair Shaft: Its Application to Ultraviolet—and Radio Frequency—Treated Hair", *Annals New York Assembly of Sciences*, 642:491–2 (Dec. 1991).

Polla et al., "Melanosomes Are a Primary Target of Q–Switched Ruby Laser Irradiation in Guinea Pig Skin", *The Journal of Investigative Dermatology*, 89(3):281–6 (Sep. 1987).

Raulin et al, "Treatment of a Nonresponding Port–Wine Stain With a New Pulsed Light Source (PhotoDerm®VL)", *Laser Surg Med.*, 21(2):203–8 (1997).

Raulin et al., "Effective Treatment of Hypertrichosis with Pulsed Light: A Report of Two Cases", *Annals of Plastic Surgery*, 39(2):169–173 (Aug. 1997).

Raulin et al., "Photoderm VL®—efficiency and limitations of an intense pulsed light source", *Australian Journal of Dermatology*, 38(2) (Jun. 1997) (Abstract Only).

Raulin et al., "Treatment of Adult Port–Wine Stains Using Intense Pulsed Light Therapy (PhotoDerm®VL): Brief Initial Clinical Report", *Dermatol Surg*, 23(7):594–7 (Jul. 1997).

Raulin et al., "Treatment of benign venous malformation with an intense pulsed source (PhotoDerm®VL)", Europena Journal of Dermatology 7(4):279–285 (Jun. 1997).

Riggle et al., "Laser Effects on Normal and Tumor Tissue", 35–63 (Not Dated).

Sadick et al., "Advances in Laser Surgery for Leg Veins: Bimodal Wavelength Approach to Lower Extremity Vessels, New Cooling Techniques, and Longer Pulse Durations", *Dermatol Surg.*, 28:1:16–20 (Jan. 2002).

Sadick et al., "Long–term Photoepilation Using a Broad–spectrum Intense Pulsed Light Source", *Arch Dermatol*, 136:1336–1340 (Nov. 2000).

Sadick, "A dual wavelength approach for laser/intense pulsed light source treatment of lower extremity veins", *J Am Acad Dermatol*, 46(1):66–72 (Jan. 2002).

Sadick, "The Role of Combined Intense Pulsed Light/Radiofrequency Technology in the Management of Blond and White Hair Photoepilation", (Feb. 7, 2003, ISHR, Aspen, Colorado).

Schroeter et al., "An Intense Light Source", *Dermatol Surg.*, 24:743–748 (1998).

Schroeter et al., "Clinical significance of an intense, pulsed light source on leg telangiectasias of up to 1 mm diameter", *Eur J Dermatol*, 7:38–42 (Jan.–Feb. 1997).

Shimbashi et al., "Ruby Laser Treatment of Pigmented Skin Lesions", *Aesth. Plast. Surg.*, 19(3):225–9 (1995).

Svaasand et al., "On the physical rationale of laser induced hyperthermia", 65–81 (Not Dated).

Taylor et al., "Treatment of Tattoos by Q–Switched Ruby Laser", *Arch Dermatol*, 126(7): 893–9 (Jul. 1990).

Troxler, "One Clinic's Experience in the Treatment of Varicose Veins and Leg Telangiectasias with the VascuLight™ Intense Pulsed Light / Nd:YAG Laser Source", *Clinical Application Notes*, 8(3) (2001).

Waldman et al., "Cutaneous inflammation: Effects of hydroxy acids and eicosand inhibitors on vascular permeability", *The Journal of Investigative Dermatology*, 88:523 (1987) (Abstract Only).

Warren, "Pigmentation induction by melanocyte stimulating hormone in human skin culture", *The Journal of Investigative Dermatology*, 88:523 (1987) (Abstract Only).

Wastek et al., "Characterization of H–substance P (SP) binding to a mouse monoclonal mast cell line", *The Journal of Investigative Dermatology*, 88:523 (1987) (Abstract Only).

Watanabe et al., "The effect of pulse duration on selective pigmented cell injury by dye lasers", *The Journal of Investigative Dermatology*, 88:523 (1987) (Abstract Only).

Weir et al., "Photo–assisted epilation—review and personal observations", *Journal of Cutaneous Laser Therapy*, 1:135–143 (1999).

Weiss et al., "Intense pulsed light: newer perspective", *Dermatol. Surg.*, 23(10):941–945 (1997).

Weiss et al., "New Treatment for Telangiecases and Venulectases: Status of Intense Pulsed Light Therapy", (Not Dated).

Weiss et al., "Sclerotherapy in the U.S.", *Dermatol. Surg.*, 21:393–396 (1995).

Weisman et al., "Growth, collogen and glycosaminoglycan synthesis by dermal fribroblasts derived from puva treated and psoriatic patients", *The Journal of Investigative Dermatology*, 88:523 (1987) (Abstract Only).

Welsh et al., "Evaluation of Cooling Techniques for the Protection of the Epidermis During ND–YAG Laser Irradiation of the Skin", *Neodymium–YAG Laser in Medicine and Surgery*, (1983).

Werner et al., "New possibilities of epilation with a high energy flash lamp", (Not Dated).

Wertz et al., "Effects of essential fatty acid deficiency on the structure and function of epidermal lipids", *The Journal of Investigative Dermatology*, 88:523 (1987) (Abstract Only).

Wheeland, "Laser–Assisted Hair Removal", *Dermatol Clin.*, 15(3):469–477 (Jul. 1997).

Woo, "Using EpiLight® for Hair Removal Treatment of Fitzpatrick Skin Types IV and V", *Clinical Application Notes*, 2(3):1–4 (1998).

Yanai et al., "Argon Laser Therapy of Port–Wine Stains: Effects and Limitations", *Plastic and Reconstructive Surgery*, 75(4):520–525 (Apr. 1985).

Yules et al., "The Effect of Q–Switched Ruby Laser Radiation on Dermal Tattoo Pigment in Man", *Arch Surg*, 95 (Aug. 1967).

Zeitter et al., "Laser Characteristics that Might be Useful in Biology", Chapter 1, 1–18 (Not Dated).

Zelickson et al., "EpiLight® Treatment of Hair Removal Using the Circulating Cooling Device: Preliminary Study Report" (Not Dated).

Goldman et al., "Effect of the Laser Beam on the Skin", *The Journal of Investigative Dermotology*, 40:121–122 (Mar. 1963).

Westinghouse Engineer, "Special Blue Lamp Helps Treat Jaundice in Newborn Infants", 31(1) (Jan. 1971).

*Lumenis Ltd., et al. v. Syneron Medical Ltd., et al.*, 2:02–cv–08269–ABC–PLA, C.D. CA.—Syneron Inc.'s Answer to Plaintiffs' Complaint (Nov. 19, 2002).

*Lumenis Ltd., et al. v. Syneron Medical Ltd., et al.*, 2:02–cv–08269–ABC–PLA, C.D. CA.—Syneron Medical Ltd.'s Answer to Plaintiffs' Complaint (Dec. 9, 2002).

*Lumenis Ltd., et al. v. Syneron Medical Ltd., et al.*, 2:02–cv–08269–ABC–PLA, C.D. CA.—Appendix of Dictionary References in Support of Plaintiffs' Report of Court–Appointed Expert (Jan. 9, 2003).

*Lumenis Ltd., et al. v. Syneron Medical Ltd., et al.*, 2:02–cv–08269–ABC–PLA, C.D. CA.—Syneron's Appendix of Prior Art References Discussed in Declaration of Dr. Warren S. Grundfest (May 8, 2003).

*Lumenis Ltd., et al. v. Syneron Medical Ltd., et al.*, 2:02–cv–08269–ABC–PLA, C.D. CA.—Plaintiffs' Report to Court–Appointed Expert Dr. Bahram (Dec. 30, 2002).

*Lumenis Ltd., et al. v. Syneron Medical Ltd., et al.*, 2:02–cv–08269–ABC–PLA, C.D. CA.—Complaint for Patent Infringement (Oct. 30, 2002).

*Lumenis Ltd., et al. v. Syneron Medical Ltd., et al.*, 2:02–cv–08269–ABC–PLA, C.D. CA.—Declaration of Alon Maor in Support of Plaintiffs' Motion for Preliminary Injunction (Apr. 25, 2003).

*Lumenis Ltd., et al. v. Syneron Medical Ltd., et al.*, 2:02–cv–08269–ABC–PLA, C.D. CA.—Declaration of Alon Maor in Support of Plaintiffs' Ex Parte Application for Temporary Retraining Order and Order to Show Cause Re Preliminary Injunction (Oct. 30, 2002).

*Lumenis Ltd., et al. v. Syneron Medical Ltd., et al.*, 2:02–cv–08269–ABC–PLA, C.D. CA.—Declaration of Benjamin J. Fox in Opposition of Plaintiffs' Motion for a Preliminary Injunction (May 8, 2003).

*Lumenis Ltd., et al. v. Syneron Medical Ltd., et al.*, 2:02–cv–08269–ABC–PLA, C.D. CA.—Declaration of Domenic Serafino Re: Plaintiffs' Motion for Preliminary Injunction and Posting of Bond (Jul. 25, 2003).

*Lumenis Ltd., et al. v. Syneron Medical Ltd., et al.*, 2:02–cv–08269–ABC–PLA, C.D. CA.—Declaration of Dr. Michael Kreindel In Opposition to Motion for Preliminary Injunction (May 8, 2003).

*Lumenis Ltd., et al. v. Syneron Medical Ltd., et al.*, 2:02–cv–08269–ABC–PLA, C.D. CA.—Declaration of Dr. Warren S. Grundfest in Support of Syneron's Opposition to Plaintiffs' Motion for Preliminary Injunction (May 8, 2003).

*Lumenis Ltd., et al. v. Syneron Medical Ltd., et al.*, 2:02–cv–08269–ABC–PLA, C.D. CA.—Declaration of Felix T. Woo in Support of Plaintiffs' Motion for Preliminary Injunction (May 20, 2003).

*Lumenis Ltd., et al. v. Syneron Medical Ltd., et al.*, 2:02–cv–08269–ABC–PLA, C.D. CA.—Declaration of Felix T. Woo in Support of Plaintiffs Ex Parte Application for Temporary Restraining Order and order to Show Cause Re Preliminary Injunction (Oct. 30, 2002).

*Lumenis Ltd., et al. v. Syneron Medical Ltd., et al.*, 2:02–cv–08269–ABC–PLA, C.D. CA.—Declaration of Harry F. Manbeck, Jr. in Response to Expert Report of Gerald J. Mossinghoff (May 27, 2003).

*Lumenis Ltd., et al. v. Syneron Medical Ltd., et al.*, 2:02–cv–08269–ABC–PLA, C.D. CA.—Declaration of John M. May in Support of Opposition to Plaintiffs' Ex Parte Application for Temporary Restraining Order and Order to Show Cause Regarding Preliminary Injunction (Nov. 1, 2002).

*Lumenis Ltd., et al. v. Syneron Medical Ltd., et al.*, 2:02–cv–08269–ABC–PLA, C.D. CA.—Declaration of Jordan A. Sigale in Support of Lumenis' Response to Syneron's Objections to Lumenis' Proposed Order Re: Preliminary Injunction and Posting of Bond (Jul. 31, 2003).

*Lumenis Ltd., et al. v. Syneron Medical Ltd., et al.*, 2:02–cv–08269–ABC–PLA, C.D. CA.—Declaration of Laura A. Wytsma in support of Plaintiffs' Ex Parte Application for Temporary Restraining Order and order to Show Cause Re Preliminary Injunction (Oct. 30, 2002).

*Lumenis Ltd., et al. v. Syneron Medical Ltd., et al.*, 2:02–cv–08269–ABC–PLA, C.D. CA.—Declaration of Moshe Mizrahy in Opposition to Plaintiffs' Motion for Preliminary Injunction (May 8, 2003).

*Lumenis Ltd., et al. v. Syneron Medical Ltd., et al.*, 2:02–cv–08269–ABC–PLA, C.D. CA.—Declaration of Moshe Mizrahy in support of Opposition to Plaintiffs' Ex Parte Application for Temporary Restraining Order and Order to Show Cause Re Preliminary Injunction (Nov. 1, 2002).

*Lumenis Ltd., et al. v. Syneron Medical Ltd., et al.*, 2:02–cv–08269–ABC–PLA, C.D. CA.—Declaration of Robert Anderson in Support of Plaintiffs' Ex Parte Application for Temporary Restraining order and Order to Show Cause re Preliminary Injunction (Nov. 1, 2002).

*Lumenis Ltd., et al. v. Syneron Medical Ltd., et al.*, 2:02–cv–08269–ABC–PLA, C.D. CA.—Declaration of Sarit Moussayoff in Support of Plaintiffs' Motion for Preliminary Injunction (May 20, 2003).

*Lumenis Ltd., et al. v. Syneron Medical Ltd., et al.*, 2:02–cv–08269–ABC–PLA, C.D. CA.—Declaration of Shimon Eckhouse in Support of Opposition to Plaintiffs' Ex Parte Application for Temporary Restraining Order to Show Cause re Preliminary Injunction (Nov. 1, 2002).

*Lumenis Ltd., et al. v. Syneron Medical Ltd., et al.*, 2:02–cv–08269–ABC–PLA, C.D. CA.—Plaintiff Lumenis Ltd. And Lumenis Inc.'s Ex Parte Application for Temporary Restraining Order to Show Cause Re Preliminary Injunction; Memorandum of Points and Authorities; Declarations of Alon Maor, Robert Anderson and Felix T. Woo; [Proposed] Order (Oct. 28, 2000).

*Lumenis Ltd., et al. v. Syneron Medical Ltd., et al.*, 2:02–cv–08269–ABC–PLA, C.D. CA.—Expert Report of Hon. Gerald J. Mossinghoff in support of Plaintiffs' Motion for Preliminary Injunction (May 20, 2003).

*Lumenis Ltd., et al. v. Syneron Medical Ltd., et al.*, 2:02–cv–08269–ABC–PLA, C.D. CA.—Syneron Medical Ltd.'s First Amended Answer to Plaintiffs' Complaint (Apr. 23, 2003).

*Lumenis Ltd., et al. v. Syneron Medical Ltd., et al.*, 2:02–cv–08269–ABC–PLA, C.D. CA.—Syneron Inc.'s First Amended Answer to Plaintiffs' Complaint (Apr. 23, 2003).

*Lumenis Ltd., et al. v. Syneron Medical Ltd., et al.*, 2:02–cv–08269–ABC–PLA, C.D. CA.—Plaintiffs' Memorandum of Points and Authorities in Support for Preliminary Injunction (Apr. 25, 2003).

*Lumenis Ltd., et al. v. Syneron Medical Ltd., et al.*, 2:02–cv–08269–ABC–PLA, C.D. CA.—Syneron'Memorandum of Points and Authorities in Opposition to Plaintiffs' Motion for a Preliminary Injunction (May 28, 2003).

*Lumenis Ltd., et al. v. Syneron Medical Ltd., et al.*, 2:02–cv–08269–ABC–PLA, C.D. CA.—Plaintiffs' Ex Parte Application for Temporary Restraining Order and to Show Cause Re Preliminary Injunction (Nov. 4, 2002).

*Lumenis Ltd., et al. v. Syneron Medical Ltd., et al.*, 2:02–cv–08269–ABC–PLA, C.D. CA.—Plaintiffs' Notice of Errata Re Plaintiffs' Ex Parte Application for Temporary Restraining Order to Show Cause Re Preliminary Injunction (Oct. 30, 2002).

*Lumenis Ltd., et al. v. Syneron Medical Ltd., et al.*, 2:02–cv–08269–ABC–PLA, C.D. CA.—Notice of Errata (Jan. 8, 2003).

*Lumenis Ltd., et al. v. Syneron Medical Ltd., et al.*, 2:02–cv–08269–ABC–PLA, C.D. CA.—Plaintiffs' Notice of Lodging Opinion and Tutorial of Court Appointed Expert Dr. Oscar M. Stafsudd (Apr. 25, 2003).

*Lumenis Ltd., et al. v. Syneron Medical Ltd., et al.*, 2:02–cv–08269–ABC–PLA, C.D. CA.—Notice of Court Appointed Expert to Order Seeking Clarification (Jun. 16, 2003).

*Lumenis Ltd., et al. v. Syneron Medical Ltd., et al.*, 2:02–cv–08269–ABC–PLA, C.D. CA.—Syneron Inc.'s Objection to Declaration of Robert Anderson Submitted in Support of Plaintiffs' Ex Parte Application for Temporary Restraining order and Order to Show Cause Re Preliminary Injunction (Nov. 1, 2002).

*Lumenis Ltd., et al. v. Syneron Medical Ltd., et al.*, 2:02–cv–08269–ABC–PLA, C.D. CA.—Defendant Syneron, Inc.'s Opposition to Plaintiffs' Ex Parte Application for Temporary Restraining Order and Order to Show Cause Re Preliminary Injunction (Nov. 1, 2002).

*Lumenis Ltd., et al. v. Syneron Medical Ltd., et al.*, 2:02–cv–08269–ABC–PLA, C.D. CA.—Plaintiffs' Motion for Preliminary Injunction (Jul. 11, 2003).

*Lumenis Ltd., et al. v. Syneron Medical Ltd., et al.*, 2:02–cv–08269–ABC–PLA, C.D. CA.—Plaintiffs' Motion for Preliminary Injunction (Aug. 5, 2003).

*Lumenis Ltd., et al. v. Syneron Medical Ltd., et al.*, 2:02–cv–08269–ABC–PLA, C.D. CA.—Reply of Plaintiffs' Lumenis Ltd. And Lumenis Inc. in Support of Motion for Preliminary Injunction (May 22, 2003).

*Lumenis Ltd., et al. v. Syneron Medical Ltd., et al.*, 2:02–cv–08269–ABC–PLA, C.D. CA.—Reply Opinion of Joseph T. Walsh, Jr. in support of Plaintiffs' Motion for Preliminary Injunction (May 20, 2003).

*Lumenis Ltd., et al. v. Syneron Medical Ltd., et al.*, 2:02–cv–08269–ABC–PLA, C.D. CA.—Syneron's Response Brief for Court–Appointed Expert Re: Claim Construction (Jan. 17, 2003).

*Lumenis Ltd., et al. v. Syneron Medical Ltd., et al.*, 2:02–cv–08269–ABC–PLA, C.D. CA.—Plaintiffs' Response Brief to Court–Appointed Expert (Jan. 9, 2003).

*Lumenis Ltd., et al. v. Syneron Medical Ltd., et al.*, 2:02–cv–08269–ABC–PLA, C.D. CA.—Submission of Materials for Court Appointed Expert Pursuant to the Parties' Joint Stipulation (Dec. 19, 2002).

*Lumenis Ltd., et al. v. Syneron Medical Ltd., et al.*, 2:02–cv–08269–ABC–PLA, C.D. CA.—Supplemental Declaration Of Alon Moar in Support of Plaintiff Lumenis, Inc.'s Motion for Preliminary Injunction (May 23, 2003).

*Lumenis Ltd., et al. v. Syneron Medical Ltd., et al.*, 2:02–cv–08269–ABC–PLA, C.D. CA.—Supplemental Declaration of Felix T. Woo in Support of Plaintiffs' Ex Parte Application for Temporary Restraining Order and Order to Show Cause Re Preliminary Injunction (Nov. 4, 2002).

*Lumenis Ltd., et al. v. Syneron Medical Ltd., et al.*, 2:02–cv–08269–ABC–PLA, C.D. CA.—Plaintiffs' Disclosures Persuant to Fed.R.Civ.P.26 (Jan. 14, 2003).

*Lumenis Ltd., et al. v. Syneron Medical Ltd., et al.*, 2:02–cv–08269–ABC–PLA, C.D. CA.—Plaintiffs' Response to Synerons' First Set of Interrogatories (Jan. 13, 2003).

*Lumenis Ltd., et al. v. Alma Ltd. et al.*, 07:CV3622, N.D.III—Videotaped Deposition of Richard R. Anderson, M.D. (Dec. 13, 2007).

Aculight HR, *Operator Manual*, PB 3581110 Revision B (Jul. 2001).

AestiLight™ Millenium, *Operator Manual*, PB 3381110 Revision A (Aug. 2003).

AestiLight™ Photo Epilation System, *AestiLight Service Manual*, PB 3380120 Revision B (Mar. 2003).

AestiLight™ Photo Epilation System, *Operator Manual*, PB 3380110 Revision A (May 1999).

EpiLight™ Hair Removal System, *Operator Manual*, PB 400–9001 Revision 9 (Aug. 2000).

EpiLight™ Hair Removal System, *Operator Manual*, PB 400–9001 Revision 2 (Jul. 1996).

EpiLight™ Hair Removal System, Operator Manual, PB 400–9001 Revision 5 (Aug. 1997).

EpiLight™ Hair Removal System, Operator Manual, PB 400–9001 Revision 2 (Jul. 1996).

EpiLight™ Hair Removal System, Operator Manual, PB 400–9001 Revision 4 (Jul. 1997).

EpiLight™ Hair Removal System, Operator Manual, PB 400–9001 Revision 1 (Jun. 1996).

EpiLight™ Hair Removal System, Operator's Manual, PB 400–9001 Revision 7 (Jan. 1998).

EpiLight™ Hair Removal System, Operator's Manual, PB 400–9001 Revision 6 (Dec. 1997).

EpiLight™ Hair Removal System, Operator Manual, PB 400–9001 Revision 3 (Feb. 1997).

IPL Quantum HR, Operator's Manual, PB 3580110 Revision B (Jun. 2001).

IPL Quantum SR, Operator's Manual, PB 3680110 Revision A (Sep. 2000).

IPL™ Quantum DL, Operator's Manual, PB 3780110 Revision B (Jul. 2002).

IPL™ Quantum HR, Operator's Manual, PB 3580110 Revision D, (Jul. 2002).

IPL™ Quantum HR, Operator's Manual, PB 3580110 Revision C (Dec. 2001).

IPL™ Quantum SR, Operator Manual, PB 3680110 Revision D (Oct. 2002).

Lumenis IPL™ Quantum, *Service Manual*, (Mar. 2002).

PhotoDerm®, *Operator Manual*, PB 200–9001 Revision 1 (Jun. 1996).

PhotoDerm PL, *Operator Manual*, PB 200–9012 Revision A (May 1997).

PhotoDerm VL, *Operator Manual*, PB 100–9033 Revision A (May 1997).

PhotoDerm® VL, *Operator Manual*, (Jul. 1997).

PhotoDerm® VL, *Operator Manual*, PB 100–9001 Revision 2B (Oct. 1995).

PhotoDerm® VL, *Operator Manual*, PB 100–9001–1 Revision 1 (Apr. 1995).

PhotoDerm® VL/PL, *Operator's Manual*, PB 2180150 Revision B (May 1998).

PhotoDerm® VL/PL, *Service Manual*, PB 100–9022 Revision 2 (Nov. 1996).

PhotoDerm® VL/PL/HR, *Operator Manual*, PB 2280150 Revision B (May 1998).

TowHead PhotoDerm®, *Service Manual*, (Apr. 2000).

VascuLight EPI Mode, *Operating Instructions*, PB 2300410 Revision C (Dec. 2001).

VascuLight™ Elite, *Operator's Manual*, PB 2780110 Revision A (Oct. 2002).

VascuLight™, *Operator Manual*, PB 2380150 Revision B (2001).

EpiLight® Hair Removal System, *Service Manual*, PB4009007 Revision B (Jan. 1999).

AcuLight™ *Operator's Manual*, PB 3581110 Revision 0 (Feb. 2001).

IPL Quantum HR, *Operator Manual*, PB3580110 Revision A (Jun. 2000).

EpiLight® Hair Removal System, *Operator Manual*, PB4009001Revision (Nov. 1998).

ESC Medical, "New Photo–Epilation Technique for Hair Removal", *Medco Forum*, 4(13) (Sep. 1997).

Reliant Technologies, Inc. Product News,Accu–Scan, Multi–Wavelength Laser Scanning System for CO2, Jan. 25, 1995, 3 pages.

Sharplan Swiftlase Flashscan, Jun. 1993.

UNILASE A new CO2 Laser for Microsurgery, I.L. Med. Newsletter, vol. 1, No. 3, Spring 1991.

I. L. Med. Unilase System Brochure (1993).

Achauer et al., "Argon Laser Treatment of Telangiectasia of the Face and Neck: 5 Years' Experience", *Lasers Surg. Med.*, 7:495–498 (1987).

Alora et al., "Recent Developments in Cutaneous Lasers", *Lasers Surg. Med.*, 26:108–118 (2000).

Alster et al., "Treatment of Port–Wine Stains with the Flashlamp–pumped Pulsed Dye Laser: Extended Clinical Experience in Children and Adults",*Ann. Plast. Surg.*, 32(5):478–484 (1994).

Altshuler et al., "Extended Theory of Selective Photothermolysis", *Lasers Surg. Med.*, 29:416–432 (2001).

Ambrose et al., "Prospective randomized comparison of photocoagulation and rubber band ligation in treatment of haemorrhoids", *Br. Med. J.*, 286:1389–1391 (1983).

Anderson et al., "Mechanisms of Selective Vascular Changes Caused by Dye Lasers",*Lasers Surg. Med.*, 3:211–215 (1983).

Anderson et al., "Microvasculature Can Be Selectively Damaged Using Dye Lasers: A Basic Theory and Experimental Evidence in Human Skin",*Lasers Surg. Med.*, 1:263–276 (1981).

Anderson et al., "Selective Photothermolysis: Precise Microsurgery by Selective Absorption of Pulsed Radiation", *Science*, 220–524–527 (1983).

Anderson, T.F., "Light Sources in Photomedicine", in *Clinical Photomedicine*, Chapter 3, pp. 37–58, Marcel Dekker, Inc., New York (1993).

Angermeier, M.C., "Treatment of facial vascular lesions with intense pulsed light", *J. Cutan. Laser Ther.*, 1:95–100 (1999).

Anvari et al., "Selective cooling of biological tissues: application for thermally mediated therapeutic procedures", *Phys. Med. Biol.*, 40:241–252 (1995).

Apfelberg et al., "Comparison of Argon and Carbon Dioxide Laser for Treatment of Decorative Tattoos Clinical and Pathological Observations", *Lasers Surg. Med.*, 3:183 (Abstract No. 294) (1983).

Apfelberg et al., Dot or Pointillistic Method for Improvement in Results of Hypertrophic Scarring in the Argon Laser Treatment of Portwine Hemangiomas,*Lasers Surg. Med.*, 6:552–558 (1987).

Apfelberg et al., "Investigation of YAG Laser Uses in Plastic Surgery", *Lasers Surg.*, 6:246 (Abstract No. 77) (1986).

Apfelberg et al., "Preliminary Investigation of KTP/532 Laser Light in the Treatment of Hemangiomas and Tattoos", *Lasers Surg. Med.*, 6:38–42 (1986).

Apfelberg et al., "Progress Report on Extended Clinical Use of the Argon Laser for Cutaneous Lesions", *Lasers Surg. Med.*, 1:71–83 (1980).

Apfelberg et al., "Progress Report on Multicenter Study of Laser–Assisted Liposuction", *Aesth. Plast. Surg.*, 18:259–264 (1994).

Apfelberg et al., "Results of Argon and CO2 Laser Exposure of Telangiectasia of the Lower Extremity: A Preliminary Report", *Lasers Surg. Med.*, 3:149 (Abstract No. 165) (1983).

Apfelberg et al., "Study of Three Laser Systems for Treatment of Superficial Varicosities of the Lower Extremity", *Lasers Surg. Med.*, 7:219–223 (1987).

Apfelberg et al., "Superpulse $CO_2$ Laser Treatment of Facial Syringomata", *Lasers Surg. Med.*, 7:533–537 (1987).

Apfelberg et al., "Update on Laser Usage in Treatment of Decorative Tattoos", *Lasers Surg. Med.*, 2:169–177 (1982).

Apfelberg, D.B., "Intralesional Laser Photocoagulation—Steroids as an Adjunct to Surgery for Massive Hemangiomas and Vascular Malformations", *Ann. Plast. Surg.*, 35:144–148 (1995).

Ara et al., "Irradiation of Pigmented Melanoma Cells with High Intensity Pulsed Radiation Generates Acoustic Waves and Kills Cells", *Lasers Surg. Med.*, 10:52–59 (1990).

Ashinoff et al., "Cappilary Hemangiomas and Treatment with the Flash LampPumped Pulse Dye Laser", *Arch. Dermatol.*, 127:202–205 (1991).

Ashinoff et al., "Flashlamp–pumped pulsed dye laser port–wine stains in infancy: Earlier versus later treatment", *J. Am. Acad. Dermatol.*, 24:467–472 (1991).

Bell et al., "100 μsec pulsed $CO_2$ laser resurfacing of lower eyelids: Erythema and rhytides reduction", *SPIE*, 2970:360–366 (1997).

Broska et al., "Comparison of the Argon Tunable Dye Laser with the Flashlamp Pulsed Dye Laser in Treatment of Facial Telangiectasia", *J. Dermatol. Surg. Oncol.*, 20:749–753 (1994).

Brugmans et al., "Temperature Response of Biological Materials to Pulsed Non–Ablative $CO_2$ Laser Irradiation", *Lasers Surg. Med.*, 11:587–597 (1991).

Burson et al., "Gel de Transmission de Ultrasonidos: Estudio Comparitivo de Distintas Formulaciones", *Farm Hosp.*, pp. 394–399 (1991) (in Spanish, with English Abstract Only).

Cates, M.C., "A long pulse (5μs) e–beam pumped XeF laser", *SPIE*, 1225:34–43 (1990).

Cates, M.C., "Excimer laser produced plasma studies", *SPIE*, 1279:102–111 (1990).

Chess et al., "Cool Laser Optics Treatment of Large Telangiectasia of the Lower Extremeties", *J. Dermatol. Surg. Oncol.*, 19:74–80 (1993).

Chissler et al., "Tanning Beds Are Not Without Drawbacks", *FDA Consumer*, pp. 21–22 (1984).

Cliff et al., "Treatment of mature port wine stains with the PhotoDerm VL", *J. Cutan. Laser Ther.*, 1:101–104 (1999).

Cole–Beuglet et al., "Ultrasound mammography for the Augmented Breast", *Radiology*, 146:737–742 (1983).

Colver et al., "Port Wine Stains", *J. Roy. Soc. Med.*, 80:603 (1987).

Colver et al., "Precise dermal damage with an infrared coagulator", *Br. J. Dermatol.*, 114:603–608 (1986).

Colver et al., "Tattoo removal using infra–red coagulation", *Br. J. Dermatol*, 112:481–485 (1985).

Colver G.B., "The Infrared Coagulator in Dermatology", *Dermatologic Clinics*, 7(1):155–167 (1989).

Daniell et al., "A History of Photodynamic Therapy", *Aust. N. Z. J. Surg.*, 61:340–348 (1991).

Denham et al., "Light Distribution in Laser Irradiated Tissue", *Lasers Surg. Med.*, 5:141 (Abstract No. 21) (1985).

Dzubow et al., "Leg Veins and Stretch Marks", *Am. Soc. Dermatol. Surg.*, 22:321 (1996).

Efthymiopoulos et al., "High–energy Short–pulse Flashlamps: Operating Characteristics", *Applied Optics*, 16:70–75 (1997).

Ell et al., "Laser Lithotripsy of Gallstone by Means of a Pulsed Neodymium YAG Laser—In Vitro and Animal Experments", *Endoscopy*, 18:92–94 (1986).

Englehardt et al., "Spectroscopy During Laser Induced Shock Wave Lithotripsy", *SPIE*, 906:200–204 (1988).

Fitzpatrick et al., "Flashlamp–pumped Pulsed Dye Laser Treatment of Port–Wine Stains", *J. Dermatol. Surg. Oncol.*, 20:743–748 (1994).

Fitzpatrick et al., "Treatment of Leg Veins: A Comparison of Laser Therapy with a Noncoherent, Multiwave Ligth Source", *Proc. Ann. Meeting IEEE Laser & Electro–Optics Soc*, pp. 238–239 (1993).

Flock et al., "Er:YAG Laser–Induced Changes in Skin In Vivo And Transdermal Drug Delivery", *SPIE*, 2970:374–379 (1997).

Flock et al., "Thermal Damage of Blood Vessels in Rat Skin–flap Window Chamber Using Indocyanine Green and a Pulsed Alexandrite Laser: A Feasibility Study", *Lasers Med. Sci.*, 8:185–196 (1993).

Foster et al., "The Successful Use of the PhotoDerm VL in the Treatment of a Cavernous Hemangioma in a Dark–Skinned Infrant", *Minimally Invasive Surgical Nursing*, 10:102–104 (1996).

Garden et al., "Effect of Dye Laser Pulse Duration on Selective Cutaneous Vascular Injury", *J. Invest. Dermatol.*, 87(5):653–657 (1986).

Garden et al., "The Treatment of Port–wine Stains by the Pulsed Dye Laser: Analysis of Pulse Duration and Long–term Therapy", *Arch. Dermatol.*, 124:889–896 (1998).

Geronemus et al., "The Medical Necessity of Evaluation and Treatment of Port–Wine Stains", *J. Dermatol. Surg. Oncol.*, 17:76–79 (1991).

Gijsbers et al., "CW Laser Ablation Velocities as a Function of Absorption in an Experimental One–Dimensional Tissue Model", *Lasers Surg. Med.*, 11:287–296 (1991).

Gijsbers et al., "Effect of Force on Ablation Depth for a XeCl Excimer Laser Beam Delivered by an Optical Fiber in Contact with Arterial Tissue Under Saline", *Lasers Surg. Med.*, 12:576–584 (1992).

Gilbert, D.J., "Incorporating Photodynamic Therapy Into a Medical and Cosmetic Dermatology Practice", *Dermatol. Clin.*, 25:111–118 (2007).

Gold et al., "5–Aminolevulinic Acid Photodynamic Therapy: Where We Have Been and Where We Are Going", *Dermatol. Surg.*, 30:1077–1084 (2004).

Gold et al., "One–Year Follow–Up Using an Intense Pulsed Light Source for Long–Term Hair Removal", *J. Cutan. Laser Ther.*, 1:167–171 (1999).

Gold et al., "Treatment of Wrinkles and Skin Tightening Using Aluma™ Skin Renewal System with FACES™ (Functional Aspiration Controlled Electrothermal Stimulation) Technology", *Aesthetic Buyers Guide*, pp. 1–6 (2005).

Gold, M.H., "Aminolevulinic Acid Photodynamic Therapy: Medical Evidence for Its Expanded Use", *Expert Rev. Med. Devices*, 3:357–371 (2006).

Gold, M.H., "Introduction to Photodynamic Therapy: Early Experience", *Dermatol. Clin.*, 25:1–4 (2007).

Goldberg et al., "Nonablative Treatment of Rhytids With Intense Pulsed Light", *Lasers Surg. Med.*, 26:196–200 (2000).

Goldberg et al., "Q-switched Nd:YAG Laser: Rhytid Improvement by Non-Ablative Dermal Remodeling", *J. Cutan. Laser Ther.*, 2:157–160 (2000).

Goldberg, D.J., "Effect of Temperature-Controlled Cooling on Light-Based Skin Treatments", *J. Cos. Laser Ther.*, 8:155–156 (2006).

Goldberg, D.J., "Erbium: YAG Laser Resurfacing: What Is Its Role?",*Aesth. Surg. J.*, 18(4):255–260 (1998).

Goldberg, D.J., "New Collagen Formation After Dermal Remodeling with an Intense Pulsed Light Source", *J. Cutan. Laser Ther.*, 2:59–61 (2000).

Goldman et al., "600 nm Flash Pumped Dye Laser for Fragile Telangiectasia of the Elderly",*Lasers Surg. Med.*, 13:227–233 (1993).

Goldman et al., "Photodermal Sclerosis of Leg Veins", *Dermatol. Surg.*, 22:323–330 (1996).

Goldman et al., "Pulsed dye laser treatment of telangiectases with and without subtherapeutic sclerotherapy", *J. Am. Acad. Dermatol.*, 23(1):23–30 (1990).

Goldman et al., "Treatment of Cutaneous Vascular Lesions", in *Cutaneous Laser Surgery*, Chapter 2, pp. 19–105 (1994).

Goldman et al., "Treatment of port-wine stains (capillary malformation) with the flashlamp pumped pulsed dye laser", *J. Pediatrics*, 122(1):71–77 (1993).

Goldman, M.P., "Laser and Noncoherent Pulsed Light Treatment of Leg Telangiectasia and Venules", *Cos. Dermatol.*, 8(10):43–44 (1995).

Goldman, M.P., "Sclerotherapy Treatment for Varicose and Telangiectatic Leg Veins", in *Vascular and Pigmented Abnormalities*, Chapter 17, pp. 256–271 (1997).

Gomer, H., "Military laser burns away skin flaws", *The London Sunday Times*, No. 8929 (Oct. 15, 1995).

Gonzalez et al., "Treatment of telangiectases and other benign vascular lesions with the 577 nm pulsed dye laser", *J. Am. Acad. Dermatol.*, 27(2):220–226 (1992).

Gregory et al., "Effect of Blood Upon the Selective Ablation of Atherosclerotic Plaque with a Pulsed Dye Laser", *Lasers Surg. Med.*, 10:533–543 (1990).

Grevelink et al., "Update on the Treatment of Benign Pigmented Lesions with the Q-Switched Ruby Laser", *Lasers Surg. Med.*, 4:73–74 (Abstract No. 326) (1992).

Groot et al., "Comparison of the infrared coagulator and the carbon dioxide laser in the removal of decorative tattoos", *J. Am. Acad. Dermatol.*, 15:518–522 (1986).

Gustafsson et al., "A Variable Pulsewidth Vascular System for Dermatology",*SPIE*, 2128:188–196 (1994).

Guttman, C., "Novel radiofrequency-based treatment archieves skin tightening with minimal discomfort", http://www.modernmedicine.com, pp. 1–3 (2005).

Harris et al., "Facial skin resurfacing with a very short pulsed $CO_2$ laser: Beam characterization and initial histological results", *SPIE*, 2671:211–218 (1996).

Henderson, B. W., "Photodynamic therapy—coming of age", *Photodermatology*, 6:200–211 (1989).

Henning et al., "Clinical and Histological Evaluation of Portwine Stain Treatment with a Microsecond pulsed Dye-laser at 577 NM", *Lasers Surg. Med.*, 4:375–380 (1984).

Henning et al., "Port Wine Stain Coagulation Experiments with a 540-nm Continuous Wave Dye-laser", *Lasers Surg. Med.*, 2:205–210 (1983).

Henning et al., "Rhinophyma Treated by Argon Laser",*Lasers Surg. Med.*, 2:211–215 (1983).

Henning et al., "Treatment of Keloids and Hypertrofic Scars with an Argon Laser", *Lasers Surg. Med.*, 6:72–75 (1986).

Hilsenrath, J.E., "Investing it; Unsightly Veins? Zap. Wall St. Woes? Zap.",*New York Times*, http://www.nytimes.com, pp. 1–3 (Jun. 23, 1996).

Hruza et al., "Laser Skin Resurfacing", *Arch. Dermatol.*, 132:451–455 (1996).

Hughes, P.S.H., "Multiple Miliary Osteomas of the Face Ablated With Erbium: YAG Laser",*Arch. Dermatol*, 135:378–380 (1999).

"Infrared-Coagulator", Lumatec product leaflet, pp. 1–4.

Ishimaru, A., "Diffusion of light in turbid material",*Applied Optics*, 28(12):2210–2215 (1989).

Jacques, S.L., "The Role of Skin Optics in Diagnostic and Therapeutic Uses of Lasers", *Lasers Dermatol.*, pp. 1–21 (1992).

Jaitley et al., "1 MV Long Pulse Generator with Low Ripple and Low Droop", $8^{th}$ *IEEE Int'l Pulsed Power Conf.*, pp. 161–165 (1991).

Jaitley et al., "Design and Testing of Multi-output 300kV Prototype Induction Cell Pulsed Power Supply for Darht", $10^{th}$ *IEEE Int'l Pulsed Power Conf.*, pp. 1412–1421 (1995).

Jay, H.H., "Victory Over Veins", http://www.nytimes.com, pp. 1–2 (Jul. 21, 1996).

Johannigmann et al., "Ein Neues Ultraschall-Kontaktgel", *Gebursth. U. Frauenheilk*, p. 34 (1974) (in German, with English Abstract Only).

Kalka et al., "Photodynamic Therapy in Dermatology",*J. Am. Acad. Dermatol.*, 42:389–413 (2000).

Kaminester, L.H., "Suntanning Centers", *JAMA*, 244(11):1258–1259 (1980).

Kaufmann et al., "Pulsed 2.94µm erbium-YAG laser skin ablation—experimental results and first clinical application", *Clin. Exp. Dermatol.*, 15:389–393 (1990).

Keijzer et al., "Laser Beam Diameter for Port Wine Stain Treatment", *Lasers Surg. Med.*, 11:601–605 (1991).

Kennedy et al., "Photodynamic Therapy with Endogenous Protoporphyrin, IX: Basic Principles and Present Clinical Experience", *J. of Photochem. Photobio.*, 6:143–148 (1990).

Kilmer et al., "Pulse Dye Laser Treatment of Rhytids", *Lasers Surg. Med.*, p. 44 (Abstract No. 194) (1997).

Koechner, W., in *Solid State Laser Engineering*, Springer Series in Optical Sciences—vol. 1, Chapters 1–2, pp. 1–620, Springer-Verlag, New York (1976).

Lakmaker et al., "Modeling the Color Perception of Port Wine Stains and its Relation to the Depth of Laser Coagulated Blood vessels", *Lasers Surg. Med.*, 13:219–226 (1993).

Lash et al., "How We Got Here", *Lasers Surg. Med.*, 3:113 (Abstract No. 29) (1983).

Lask et al., "Laser Skin Resurfacing with the Sik Touch Flashscanner for Facial Rhytides", *Dermatol. Surg.*, 21:1021–1024 (1995).

Lask et al., "Nonablative laser treatment of facial rhytides", *SPIE*, 2970:338–349 (1997).

Levins et al., "Q-Switched Ruby Laser Treatment of Tattoos",*Lasers Surg Med.*, Suppl. 3:63–64 (Abstract No. 255) (1991).

Lowe et al., "Skin Resurfacing with the Ultrapulse Carbon Dioxide Laser",*Dermatol. Surg.*, 21:1025–1029 (1995).

Magee et al., "Vein Marketing Through Ultrasound Coupling Gel", *Eur. J. Vasc. Surg.*, 4:491–492 (1990).

Majaron et al., "Deep Coagulation of Dermal Collagen with Repetitive Er:YAG Laser Irradiation", *Lasers Surg. Med.*, 26:215–222 (2000).

Majaron et al., "Er:YAG Laser Skin Resurfacing Using Repetitive Long–Pulse Exposure and Cryogen Spray Cooling: I. Histological Study", *Lasers Surg. Med.*, 28:121–130 (2001).

Majaron et al., "Er:YAG Laser Skin Resurfacing Using Repetitive Long–Pulse Exposure and Cryogen Spray Cooling: II. Theoretical Analysis", *Lasers Surg. Med.*, 28:131–137 (2001).

Margolis et al., "Visible Action Spectrum for Melanin–Specific Selective Photothermolysis", *Lasers Surg. Med.*, 9:389–397 (1989).

Marchic et al., "White–Light Flashlamp–pumped dye laser for photography through endoscopes", *Optics Communications*, 45(1):21–25 (1983).

McCaughan et al., "Photodynamic Therapy for Cutaneous and Subcutaneous Malignant Neoplasms", *Arch. Surg.*, 124:211–216 (1989).

McCaughan et al., "Photodynamic Therapy: An Eight–Year Experience", in *Photodynamic Therapy: Basic Principles and Clinical Applications*, pp. 323–331 (1992).

Meijering et al., "Limits of Radial Time Constants to Approximate Thermal Response to Tissue", *Lasers Surg. Med.*, 13:685–687 (1993).

Miller et al., "Optical Modelling of Light Distributions in Skin Tissue Following Laser Irradiation", *Laser Surg. Med.*, 13:565–571 (1993).

Milner et al., "Analysis of nonablative skin resurfacing", *SPIE*, 2970:367–373 (1997).

Mordon et al., "Rationale for Automatic Scanners in Laser Treatment of Port wine Stains", *Lasers Surg. Med.*, 13:113–123 (1993).

Morelli et al., "Tunable Dye Laser (577 nm) Treatment of Port Wine Stains", *Lasers Surg. Med.*, 6:94–99 (1986).

Motamedi et al., "Thermal Response of Tissue During Laser Angioplasty", *Lasers Surg. Med.*, 5:172 (Abstract No. 114) (1985).

Mutzhas et al., "A New Apparatus with High Radiation Energy Between 320460 nm: Physical Description and Dermatological Applications", *J. Invest. Dermatol.*, 76:42–47 (1981).

Nakagawa et al., "Ultrastuctural Changes in Human Skin After Exposure to a Pulsed Laser", *J. Invest. Dermatol.*, 84(5):396–400 (1985).

Nestor et al., "New Perspectives on Photorejuvenation", *Skin & Aging*, 11:68–74 (2003).

Newman et al., "Variable Pulse Erbium: YAG Laser Skin Resurfacing of Perioral Rhytides and Side–by–side Comparison with Carbon Dioxide Laser", *Lasers Surg. Med.*, 26:208–214 (2000).

Parrish et al., "Exploring Mechanisms of Specificity in Laser–Tissue Interactions", *Lasers Surg. Med.*, 3:175 (Abstract No. 260) (1983).

Parrish et al., "Spatial Confinement of Thermal Effects of Pulsed Laser Irradiation of Tissue", *Lasers Surg. Med.*, 3:157 (Abstract No. 195) (1973).

Paul et al., "The Effect of Temperature and Other Factors on Selective Microvascular Damage Caused by Pulsed Dye Laser", *J. Invest. Dermatol.*, 81(4):333–336 (1983).

Pfefer et al., "Mechanisms of Laser–Induced Thermal Coagulation of Whole Blood in vitro", *SPIE*, 3590:20–31 (1999).

Philipp et al., "Treatment of Congenital Vascular Disorders: Classification, Step Programme and Therapeutical Procedures", *SPIE*, 2086:228–238 (1993).

Pickering et al., "585 nm for the Laser Treatment of Port Wine Stains: A Possible Mechanism", *Lasers Surg. Med.*, 11:616–618 (1991).

Plewig et al., "A new apparatus for the delivery of high intensity UVA and UVA + UVB irradiation, and some dermatological applications", *Br. J. Dermatol.*, 98:15–24 (1978).

Polla et al., "Tunable Pulsed Dye Laser for the Treatment of Benign Cutaneous Vascular Ectasia", *Dermatologica*, 174:11–17 (1987).

Pottier et al., "Assessment of Non–Coherent Light Sources for Photodynamic Therapy", *SPIE*, 2371:364–368 (1995).

Pratesi, R., "Potential Use of Incoherent and Coherent Light–Emitting–Diodes (LEDs) in Photomedicine", in *Photomedicine, Laser Photobiol. Photomed.*, 22:293–308 (1983).

Ramrus et al., "A Compact One–Half MV Rep–Rate Pulser", $20^{th}$ *IEEE Power Modulator Symposium*, pp. 68–71 (1992).

Ramrus et al., "Design and Performance of a One–Half MV Rep–Rate Pulser", Proc. Of the $8^{th}$ IEEE International Pulsed Power Conference, pp. 982–985 (1991).

Ranganathan et al., "Promises for Ultrasonic Waves on Activity of Silica Gel and Some Supported Catalytes", *Ind. Eng. Chem. Prod. Res. Develop.*, 12:155–158 (1973).

Rassing et al., "Measurement of Ultrasonic Absorption in a Gel by Light Diffraction and Resonator Methods", *J. Mol. Liq.*, 26;97–108 (1983).

Rastegar et al., "Technique for Measurement of One–Dimensional Instantaneous Ablation Velocity", *Lasers Surg. Med.*, 8:533–535 (1988).

Raulin et al., "Treatment of a Nonresponding Port–Wine Stain With a New Pulsed Light Source (PhotoDerm® VL)", *Lasers Surg. Med.*, 21:203–208 (1997).

Raulin et al., "Treatment of Adult Port–Wine Stains Using Intense Pulsed Light Theraphy (PhotoDerm VL): Brief Initial Clinical Report", *Dermatol. Surg.*, 23:594–601 (1997).

Raulin et al., "Treatment of benign venous malformations with an intense pulsed light source (PhotoDerm VL)", *Eur. J. Dermatol.*, 7:279–282 (1997).

Raulin et al., "Treatment of Essential Telangiectasias with an Intense Pulsed Light Source (PhotoDerm VL)", *Dermatol. Surg.*, 23:941–946 (1997).

Raulin et al., "Treatment of Port–wine Stains With a Noncoherent Pulsed Light Source", *Arch. Dermatol.*, 135:679–683 (1999).

Reyes et al., "Treatment of port–wine stains during childhood with the flashlamp–pumped pulsed dye laser", *J. Am. Acad. Dermatol.*, 23:1142–1148 (1990).

Ross et al., "Effects of $CO_2$ Laser Pulse Duration in Ablation and Residual Thermal Damage: Implications for Skin Resurfacing", *Lasers Surg. Med.*, 19:123–129 (1996).

Rowe, P.M., "Photodynamic therapy benigns to shine", *Lancet*, 351:1496 (1998).

Sadick et al., "Photorejuvenation with Intense Pulsed Light: Results of a Multi–Center Study", *J. Drugs Dermatol.*, 3(1):41–49 (2004).

Sadick, N.S., "A Structural Approach to Nonablative Rejuvenation", *Cosmetic Dermatol.*, 15(12):39–43 (2002).

Sadick, N.S., "Update on Non–Ablative Light Therapy for Rejuvenation: A Review", *Lasers Surg. Med.*, 32:120–128 (2003).

Schmiloglu et al., "Modern Pulsed Power: Charlie Martin and Beyond", *Proceedings of the IEEE,* 92(7):1014–1020 (2004).

Schroeter et al., "An Intense Light Source: The Photoderm VL–Flashlaml as a New Treatment Possibility for Vascular Skin Lesions", *Dermatol. Surg.,* 24:743–748 (1998).

Schroeter et al., "Clinical significance of an intense, pulsed light source on leg telangiectasias of up to 1 mm diameter", *Eur. J. Dermatol.,* 7:38–42 (1997).

Schroeter et al., "Photoderm VL treatment of leg teleangiectasia",*JEADV,* 5(Suppl. 1):S49 (Abstract No. W76) (1995).

Schwimer et al., "The Effect of Ultrasound Coupling Gels on Sperm Motility In Vitro",*Fertil. Steril.,* 42:946–947 (1984).

Sheean et al., "Arrest of Embryo Development by Ultrasound Coupling Gels",*Fertil. Steril.,* 45:568–571 (1986).

Smith et al., "532–Nanometer Green Laser Beam Treatment of Superficial Varicosities of the Lower Extremities", *Lasers Surg. Med.,* 8:130–134 (1988).

Steiger et al., "Comparison of Different Pulsed and Q–switched Solid–state Laser Systems for Endoscopic Laser Induced Shock Wave Lithotripsy: Performance and Laser/Stone Interactions", *SPIE,* 2300:94–101 (1990).

Strickland et al., "A 5kV, 250 kA Rep–Rated Pulser Using Parallel Ignitrons", *7$^{th}$ IEEE Int'l Pulsed Conf.,* pp. 729–731 (1989).

Sunde et al., "Traumatic Tattoo Removal: Comparison of Four Treatment Methods in an Animal Model with Correlation to Clinical Experience", *Lasers Surg. Med.,* 10:158–164 (1990).

Svaasand et al., "Light and Drug Distribution with Topically Administered Photosensitizers",*Lasers Surg. Med.,* 11:261–265 (1996).

Szeimies et al., "A Possible New Incoherent Lamp for Photodynamic Treatment of Superficial Skin Lessions", *Acta Derm. Venereal (Stockh).,* 74:117–119 (1994).

Tan et al., "Action Spectrum of Vascular Specific Injury Using Pulsed Irradiation", *J. Invest. Dermatol.,* 92(6):868–871 (1989).

Tan et al., "EMLA for Laser Treatment of Portwine Stains in Children",*Lasers Surg. Med.,* 12:543–548 (1992).

Tan et al., "Histologic Responses of Port–wine Stains Treated by Argon, Carbon Dioxide, and Tunable Dye Lasers", *Arch. Dermatol.,* 122:1016–1022 (1986).

Tan et al., "Pulsed Dye Laser Treatment of Recalcitrant Verrucae: A Preliminary Report",*Lasers Surg. Med.,* 13:127–137 (1993).

Tan et al., "Treatment of Children with Port–Wine Stains Using the Flashlamp–Pulsed Tunable Dye Laser", *N. Engl. J. Med.,* 320(7):416–421 (1989).

Taub, A.F., "Photodynamic Therapy: Other Uses",*Dermtol. Clin.,* 25:101–109 (2007).

Taylor et al., "Q–Switched Ruby Laser (QSRL) Irradiation of Benign Pigmented Lesions: Dermal vs. Epidermal", *Lasers Surg. Med.,* 3:65 (Abstract No. 262) (1991).

Templeton et al., "Comparison of infrared coagulation and rubber band ligation for first and second degree haemorrhoids: a randomized prospective clinical trial", *Br. Med. J.,* 286:1387–1389 (1983).

Troccoli et al., "Multiple–Pulse Photocoagulation of Blood Vessels With A 585 Nm Tunable Laser", *Lasers Surg. Med.,* 4:3 (Abstract No. 2) (1992).

van Gemert et al., "Can Physical Modeling Lead to an Optimal Laser Treatment Strategy for Port–Wine Stains", in *Laser Applications in Medicine and Biology,* Chapter 5, pp. 199–247, Plenum Press, New York (1991).

van Germert et al., "Instantaneous Ablation Behavior of In–Vitro Rods During Laser Irradiation", *Lasers Surg. Med.,* 5:136 (Abstract No. 4) (1985).

van Germert et al., "Is There an Optical Laser Treatment for Port Wine Stains?", *Lasers Surg. Med.,* 6:76–83 (1986).

van Germert et al., "Wavelengths for Laser Treatment of Port Wine Stains and Telangiectasia", *Lasers Surg. Med.,* 16:147–155 (1995).

"Varicose Vein Device Producer comes to U.S. Market", *Clinica,* 687:9 (Jan. 8, 1996).

Venning et al., "Tattoo removal using infra–red coagulation: a dose comparison", *Br. J. Dermatol.,* 117:99–105 (1987).

Wagner et al., "Percutalgine–Gel et Ultrasonotherapie en Pathologie du Sport", *La Revue de Medecine,* 32:1681–1683 (1982) (in French, with English Abstract Only).

Waldorf et al., "Skin Resurfacing of Fine to Deep Rhytides Using a Char–free Carbon Dioxide Laser in 47 Patients", *Dermatol. Surg.,* 21:940–946 (1995).

Walsh et al., "Er:YAG Laser Ablation of Tissue: Measurement of Ablation Rates", *Lasers Surg. Med.,* 9:327–337 (1989).

Walsh et al., "Pulsed $CO_2$ Laser Tissue Ablation: Effect of Tisse Type and Pulse Duration On Thermal Damage", *Lasers Surg. Med.,* 8:108–118 (1988).

Walsh, J.T., "Er:YAG Laser Ablation of Tissue: Effect of Pulse Duration and Tissue Type on Thermal Damage",*Lasers Surg. Med.,* 9:314–326 (1989).

Walsh, J.T., "Pulsed Laser Ablation of Tissue: Analysis of the Removal Process and Tissue Healing", *Unpublished Ph.D. dissertation Massachusetts Institute of Technology, on file with Institute Archives and Hayden Library, Massachusetts Institute of Technology,* pp. 1–312 (1988).

Weiss et al., "Rejuvenation of Photoaged Skin: 5 Years Results with Intense Pulsed Light of the Face, Neck, and Chest", *Dermatol. Surg.,* 28:1115–1119 (2002).

Welch et al., "Practical Models for Light Distribution in Laser–Irradiated Tissue", *Lasers Surg. Med.,* 6:488–493 (1987).

Werner et al., "Die Hamangiombehandlung mit dem Neodym: Yttrium Aluminium–Granat Laser (Nd:YAG–Laser)", *Laryngo–Rhino–Otol.,* 71:388–395 (1992), (in German, with English Abstract Only).

West, T., "How Laser Surgery Can Help Your Rosacea Patients", *Skin & Aging,* pp. 43–46 (1998).

Wilder, D., "Pulsed 1064–nm Nd:YAG Laser Therapy for Noninvasive Treatment of a Massive Hemagioma: Case Report", *J. Clin. Laser Med. Surg.,* 17(6):245–247 (1999).

Wilson et al., "The physics of photodynamic therapy", *Phys. Med. Biol.,* 31(4):327–360 (1986).

Gros, et al, Diaphanologie Mammaire, Memoires Originaux, *J. Radiol. Electrol.,* 53(4):297–306 (1972), in French, with English translation.

Brochure for an Infrared Coagulator by Redfield Corporation (1968).

*Groot & Johnson,* "Lasers and Advanced Dermatological Instrumentation", *Australas J. Dermatol.,* 28:77–85 (1987).

Kaufmann et al., "Pulsed Er: YAG—and 308 nm UV–Excimer Laser: An In Vitro and In Vivo Study of Skin–Ablative Effects", Laser Surg. Med., 9:132–140 (1989).

Goldman, *Biomedical Aspects of the Laser—An Introduction of Laser Applications Into Biology and Medicine,* chapters 1, 2, 23 and index (1967).

Gossman et al., "Experimental Comparison of Laser and Cryosurgical Cilia Destruction", *Ophthalmic Surgery,* 23(3):179–182 (Mar. 1992).

Gossman et al., "Prospective Evaluation of the Argon Laser in the Treatment of Trichiasis", *Ophthalmic Surgery,* 23(3):183–187 (Mar. 1992).

"The Spectrum RD–1200 Q–Switched Ruby Laser", (Not Dated).

ESC Medical Systems, "Control Pulse Duration Duration and Pulse Secuence Delays for Effective Photo–Epilation", *EpiLight Hair Removal System Application Notes,* 3(2) (1997).

Geronemus, "Laser and Pulsed Light Source Treatment of Leg Vessels", (Sep. 1995).

Goldman, "Effects of New Laser System on the Skin", *Arch Dermatol,* 108(3):385–90 (Sep. 1973).

Goldman, "Treating Varicose and Telangiectatic Leg Veins", *Federal Practitioner* (Mar. 1997).

Kincade, "New Procedures push tissue studies beneath the surface", *Laser Focus World,* pp. 57–63, (Aug. 1995).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7 and 11 is confirmed.

Claims 1–6 and 8–10 were previously cancelled.

Claims 12, 28, 33, 37 and 38 are determined to be patentable as amended.

Claims 13–27, 29–32, 34–36 and 39–41, dependent on an amended claim, are determined to be patentable.

New claims 42–56 are added and determined to be patentable.

12. A therapeutic treatment device for coagulating blood in blood vessels underlying an epidermal layer, the device comprising:
 a hand-held unit configured to be disposed in contact with a skin treatment area, including a flashlamp, at least one filter, and a light guide operable to provide a pulsed light output *of* at least 3 square centimeters in size; and
 a control box operably connected to the hand-held unit, including a power supply, at least one microprocessor, and a driver circuit, the control box being configured to switch the flashlamp between an on and off state and to control a pulse width and a delay between pulses, *wherein the pulsed light output is configured to coagulate blood in blood vessels underlying the epidermal layer*;
 wherein the pulsed light output has a wavelength of about 500–1000 nm, a pulse width of about 5 to 50 msec, and an energy density of about 6 to 30 Joules per square centimeter.

28. A therapeutic medical device for applying light to skin to coagulate blood in blood vessels underlying an epidermal layer, the device comprising:
 a housing means for disposing a flashlamp proximate to the skin;
 a filtering means for limiting the wavelength of light which impinges the skin to values within a range of 520–1000 nm;
 a light guide means for contacting the skin and directing light to at least a 4 square centimeter area of skin;
 a control means for controlling the flashlamp to provide at least one pulse of light *configured to coagulate blood in blood vessels underlying the epidermal layer, the at least one pulse of light being* characterized by a pulse width within the range of 10–50 msec, and an energy density on the skin within the range of 6–20 Joules per square centimeter, wherein the control means includes a driver circuit and is configured to switch the flashlamp between an on and off state and to control a pulse width and a delay between pulses; and
 a connection means for flexibly coupling the housing means to the control means.

33. A method of applying light to skin to coagulate blood in blood vessels underlying an epidermal layer, the method comprising:
 selecting at least one treatment parameter on a user interface, wherein the treatment parameters include a pulse width and a fluence;
 positioning a hand-held unit on area of the skin, wherein the hand-held unit includes a flashlamp, a filter, and a light guide which is placed in contact with at least a 4 square centimeter area of the skin;
 controlling the flashlamp *to coagulate blood in blood vessels underlying the epidermal layer*, including controlling the pulse width and a delay between pulses, using a switch based on the at least one treatment parameter, wherein the controlling includes switching the flashlamp between an on and an off state; and
 triggering the flashlamp to transmit a pulse of light corresponding to the at least one treatment parameter, wherein the pulse of light is capable of coagulating blood in the blood vessels underlying the epidermal layer.

37. A system for applying light to skin to coagulate blood in blood vessels underlying an epidermal layer, the system comprising:
 a control system, including:
  a user interface configured to receive a fluence parameter and a pulse width parameter;
  a microprocessor programmed to calculate a trigger signal based on the fluence parameter and the pulse width parameter;
  a driver circuit including an IGBT switch operably coupled to the microprocessor and configured to generate at least one electrical pulse based on the trigger signal;
  a plurality of capacitors operably connected to the IGBT switch;
  a charging power supply operably connected to the plurality of capacitors;
 a hand-held unit including:
  a light guide having a cross section of at least 4 square centimeters configured to contact the skin;
  a flashlamp operably connected to the driver circuit and configured to emit light to coagulate blood based on the electrical pulse;
  at least one filter disposed between the light guide and the flashlamp and configured to transmit light having wavelengths between about 520–1000 nm,
 wherein the control system is configured to switch the flashlamp such that at least a first interval of light is transmitted to the blood vessels underlying the epidermal layer, *and wherein the light is configured to coagulate blood in blood vessels*.

38. A therapeutic treatment device for coagulating blood in blood vessels underlying an epidermal layer comprising:
 a hand-held configured to be disposed in contact with a skin treatment area including an incoherent light source operable to provide a pulsed light output for coagulation of blood, wherein the incoherent light source is a flashlamp;
 a driver circuit including a switch capable of being electrically turned on and being electrically turned off to thereby provide intervals of light, *the driver circuit being configured such that the intervals of light are configured to coagulate blood in blood vessels underlying the epidermal layer,* wherein the driver circuit is connected to the light source to control the pulse width and delay between intervals of light, wherein the driver circuit is configured to cause the flashlamp to generate intervals of light having a duration of about 5–50 msec, and an energy density of about 6–20 Joules per square centimeter, and a filter configured transmit light having wavelengths of about 500–1000 nm; and a light guide configured to transmit light from the flashlamp to an area of skin that is at least 3 square centimeters in size.

42. The therapeutic treatment device of any one of claims 7 or 11 further comprising gel disposed between the light guide and the epidermal layer.

43. The therapeutic treatment device of any one of claims 13–26 further comprising a gel disposed between the skin and the hand-held unit.

44. The therapeutic medical device of any one of claims 30–32 further comprising a gel means for contacting the skin, wherein the light guide means contacts the gel means.

45. The method of any one of claims 35–36 further comprising applying gel to the skin, wherein the light guide makes contact with the gel.

46. The system of claim 37 further comprising gel disposed between the light guide and the epidermal layer.

47. The therapeutic treatment device of any one of claims 39–40 further comprising a gel disposed between the skin treatment area and the hand-held unit.

48. A therapeutic treatment device for coagulating blood in blood vessels underlying an epidermal layer, the device comprising:

a hand-held unit configured to be disposed in contact with a skin treatment area, including a flashlamp, at least one filter, and a light guide operable to provide a pulsed light output of at least 3 square centimeters in size;

a control box operably connected to the hand-held unit, including a power supply, at least one microprocessor, and a driver circuit, the control box being configured to switch the flashlamp between an on and off state and to control a pulse width and a delay between pulses; and a gel disposed between the skin and the hand-held unit;

wherein the pulsed light output has a wavelength of about 500–1000 nm, a pulse width of about 5 to 50 msec, and an energy density of about 6 to 30 Joules per square centimeter.

49. A therapeutic medical device for applying light to skin to coagulate blood in blood vessels underlying an epidermal layer, the device comprising:

a housing means for disposing a flashlamp proximate to the skin;

a filtering means for limiting the wavelength of light which impinges the skin to values within a range of 520–1000 nm;

a light guide means for contacting the skin and directing light to at least a 4 square centimeter area of skin;

a control means for controlling the flashlamp to provide at least one pulse of light characterized by a pulse width within the range of 10–50 msec, and an energy density on the skin within the range of 6–20 Joules per square centimeter, wherein the control means includes a driver circuit and is configured to switch the flashlamp between an on and off state and to control a pulse width and a delay between pulses; and a connection means for flexibly coupling the housing means to the control means; and a gel means for contacting the skin, wherein the light guide means contacts the gel means.

50. A method of applying light to skin to coagulate blood in blood vessels underlying an epidermal layer, the method comprising:

selecting at least one treatment parameter on a user interface, wherein the treatment parameters include a pulse width and a fluence;

positioning a hand-held unit on an area of the skin, wherein the hand-held unit includes a flashlamp, a filter, and a light guide which is placed in contact with at least a 4 square centimeter area of the skin;

controlling the flashlamp, including controlling the pulse width and a delay between pulses, using a switch based on the at least one treatment parameter, wherein the controlling includes switching the flashlamp between an on and an off state; and triggering the flashlamp to transmit at least one pulse of light corresponding to the at least one treatment parameter, wherein the pulse of light is capable of coagulating blood in the blood vessels underlying the epidermal layer, and applying gel to the skin, wherein the light guide makes contact with the gel.

51. The therapeutic treatment device of claim 7 or 11 wherein the light guide is solid.

52. The therapeutic treatment device of any one of claims 12–27 wherein the light guide is solid.

53. The therapeutic medical device of any one of claims 28–32 wherein the light guide means is solid.

54. The method of any one of claims 33–36 further comprising guiding the pulse of light using a solid light guide.

55. The system of claim 37 wherein the light guide is solid.

56. The system of any one of claims 38–41 wherein the light guide is solid.

* * * * *